(12) United States Patent
Faller et al.

(10) Patent No.: US 9,901,358 B2
(45) Date of Patent: *Feb. 27, 2018

(54) ULTRASONIC SURGICAL INSTRUMENT WITH INTEGRAL BLADE CLEANING FEATURE

(71) Applicant: Ethicon Endo-Surgery, Inc., Cincinnati, OH (US)

(72) Inventors: Craig N. Faller, Milford, OH (US); JoAnn M. Stegeman, Cincinnati, OH (US); Patrick A. Weizman, Liberty Township, OH (US); Cory G. Kimball, Cincinnati, OH (US); Tamara S. Vetro Widenhouse, Clarksville, OH (US); Tylor C. Muhlenkamp, Cincinnati, OH (US); William D. Kelly, Los Altos, CA (US); Brian D. Bertke, Fort Thomas, KY (US); Karalyn R. Tellio, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 678 days.

This patent is subject to a terminal disclaimer.

(21) Appl. No.: 14/081,561

(22) Filed: Nov. 15, 2013

(65) Prior Publication Data

US 2015/0142031 A1 May 21, 2015

(51) Int. Cl.
 A61B 17/32 (2006.01)
 A61B 90/70 (2016.01)
 A61B 18/00 (2006.01)

(52) U.S. Cl.
 CPC .......... *A61B 17/320092* (2013.01); *A61B 17/320068* (2013.01); *A61B 90/70* (2016.02);
 (Continued)

(58) Field of Classification Search
 CPC ......... A61B 2017/320072; A61B 2017/32008; A61B 17/320068; A61B 17/320092; A61B 90/70; A61B 2018/0097
 See application file for complete search history.

(56) References Cited

U.S. PATENT DOCUMENTS

| 3,955,859 | A | 5/1976 | Stella et al. |
|---|---|---|---|
| 5,085,657 | A | 2/1992 | Ben-Simhon |

(Continued)

FOREIGN PATENT DOCUMENTS

| EP | 0 908 155 A1 | 4/1999 |
|---|---|---|
| EP | 1 199 040 A2 | 4/2002 |

(Continued)

OTHER PUBLICATIONS

U.S. Appl. No. 13/657,553, filed Oct. 22, 2012.
(Continued)

*Primary Examiner* — Alexander Orkin
(74) *Attorney, Agent, or Firm* — Frost Brown Todd LLC

(57) ABSTRACT

An ultrasonic instrument comprises a body, a shaft assembly, an ultrasonic blade, and a pivoting member. The shaft assembly extends distally from the body. The ultrasonic blade is positioned distal to the shaft assembly. The pivoting member is pivotable with respect to the blade from an open position to a closed position to thereby clamp tissue between the pivoting member and the blade. The shaft assembly comprises a feature to provide for the removal of surgical debris (e.g. tissue, coagulated blood, etc.), body fluid, etc. from the shaft assembly. The feature may remove the surgical debris, body fluid, etc. from a cavity within the shaft assembly. The feature may also prevent the collection of surgical debris, body fluid, etc. within the shaft assembly.

8 Claims, 47 Drawing Sheets

(52) U.S. Cl.
CPC .............. *A61B 2017/32008* (2013.01); *A61B 2017/320072* (2013.01); *A61B 2017/320084* (2013.01); *A61B 2018/0097* (2013.01); *A61B 2217/005* (2013.01)

(56) References Cited

U.S. PATENT DOCUMENTS

| | | | | |
|---|---|---|---|---|
| 5,251,356 | A | * | 10/1993 | Oaki ..................... A61B 1/122 15/104.095 |
| 5,322,055 | A | | 6/1994 | Davison et al. |
| 5,423,814 | A | * | 6/1995 | Zhu .................... A61B 17/0218 606/41 |
| 5,456,681 | A | * | 10/1995 | Hajjar ................... A61B 18/24 15/104.92 |
| 5,658,273 | A | * | 8/1997 | Long .................. A61B 17/3417 606/1 |
| 5,873,873 | A | | 2/1999 | Smith et al. |
| 5,935,144 | A | * | 8/1999 | Estabrook ........ A61B 17/32006 604/22 |
| 5,980,510 | A | | 11/1999 | Tsonton et al. |
| 6,193,709 | B1 | | 2/2001 | Miyawaki et al. |
| 6,325,811 | B1 | | 12/2001 | Messerly |
| 6,773,444 | B2 | | 8/2004 | Messerly |
| 6,783,524 | B2 | | 8/2004 | Anderson et al. |
| 8,461,744 | B2 | | 6/2013 | Wiener et al. |
| 8,469,981 | B2 | | 6/2013 | Robertson et al. |
| 8,591,536 | B2 | | 11/2013 | Robertson |
| 8,623,027 | B2 | | 1/2014 | Price et al. |
| 2005/0049546 | A1 | * | 3/2005 | Messerly ........ A61B 17/32009 604/22 |
| 2006/0079874 | A1 | | 4/2006 | Faller et al. |
| 2007/0191713 | A1 | | 8/2007 | Eichmann et al. |
| 2007/0282333 | A1 | | 12/2007 | Fortson et al. |
| 2008/0200940 | A1 | | 8/2008 | Eichmann et al. |
| 2008/0235888 | A1 | * | 10/2008 | Vaillancourt ........... A61L 2/235 15/104.94 |
| 2008/0255589 | A1 | * | 10/2008 | Blakeney ........... A61B 17/1285 606/142 |
| 2008/0300611 | A1 | * | 12/2008 | Houser ............ A61B 17/32006 606/167 |
| 2009/0143806 | A1 | | 6/2009 | Witt et al. |
| 2009/0264703 | A1 | * | 10/2009 | Pribanic ................ A61B 1/0008 600/121 |
| 2010/0069940 | A1 | | 3/2010 | Miller et al. |
| 2011/0087212 | A1 | | 4/2011 | Aldridge et al. |
| 2012/0112687 | A1 | | 5/2012 | Houser et al. |
| 2012/0116265 | A1 | | 5/2012 | Houser et al. |
| 2014/0005701 | A1 | | 1/2014 | Olson et al. |
| 2014/0165309 | A1 | * | 6/2014 | Frey ..................... A61B 10/025 15/21.1 |
| 2015/0148835 | A1 | * | 5/2015 | Faller ............... A61B 17/32006 606/169 |

FOREIGN PATENT DOCUMENTS

| | | |
|---|---|---|
| EP | 2 484 301 A1 | 8/2012 |
| WO | WO 97/03618 A1 | 2/1997 |
| WO | WO 2014/078548 | 4/1999 |

OTHER PUBLICATIONS

U.S. Appl. No. 14/031,665, filed Sep. 19, 2013.
U.S. Appl. No. 61/410,603, filed Nov. 5, 2010.
International Search Report and Written Opinion dated Apr. 10, 2015 for Application No. PCT/US2014/065002, 19 pgs.

* cited by examiner

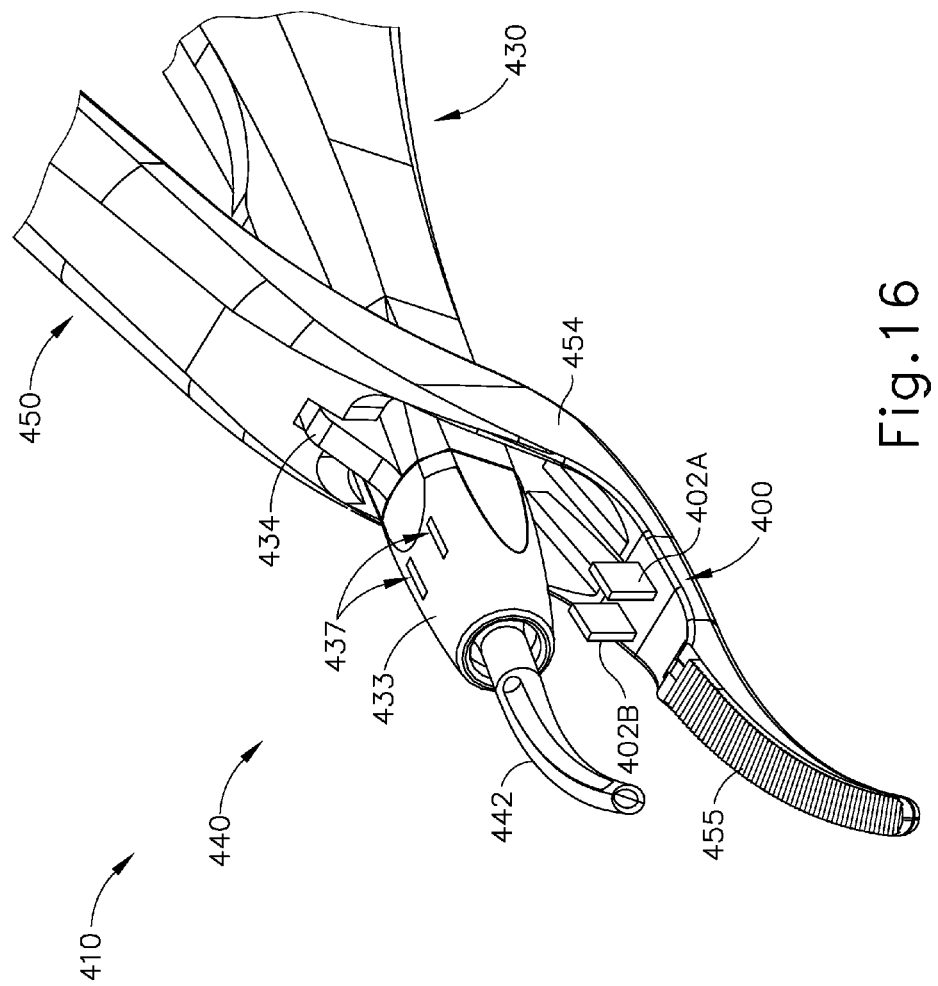

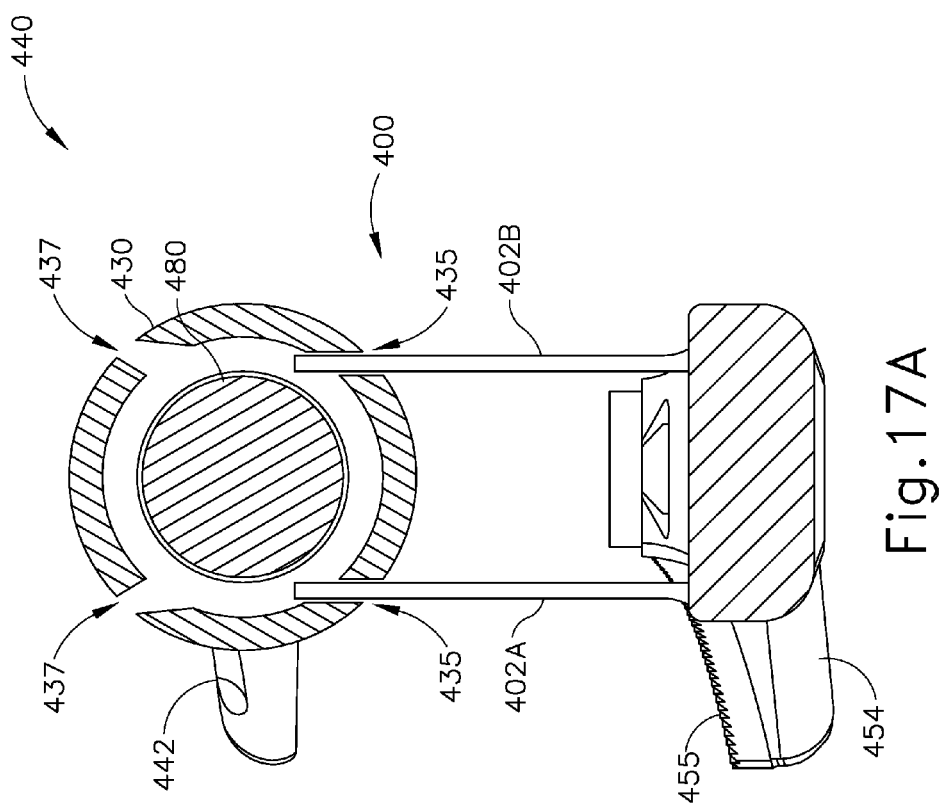

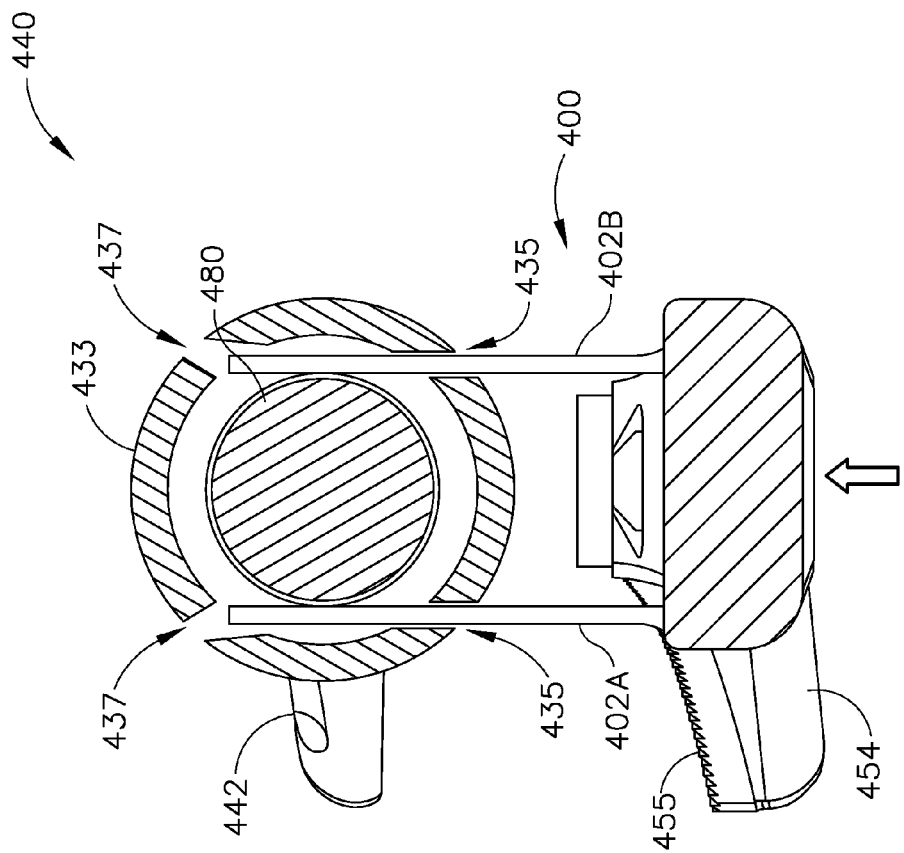

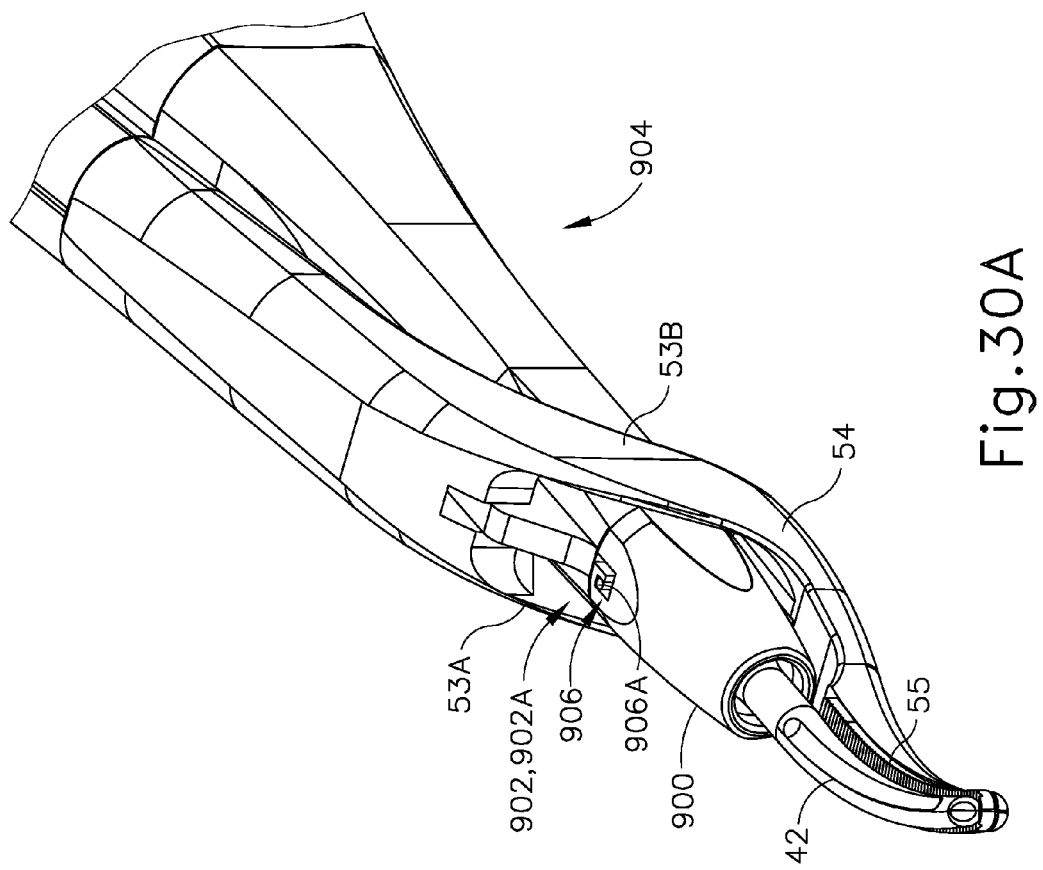

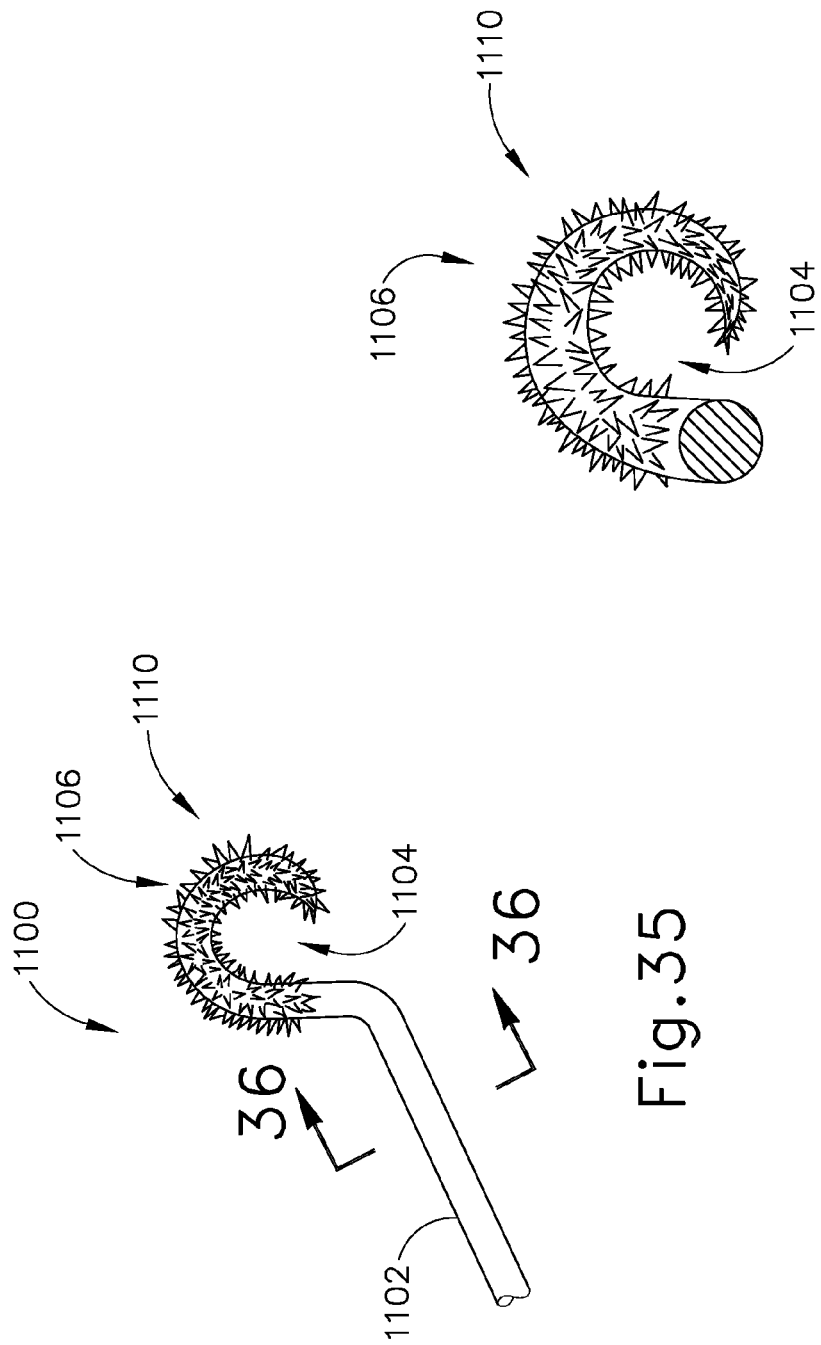

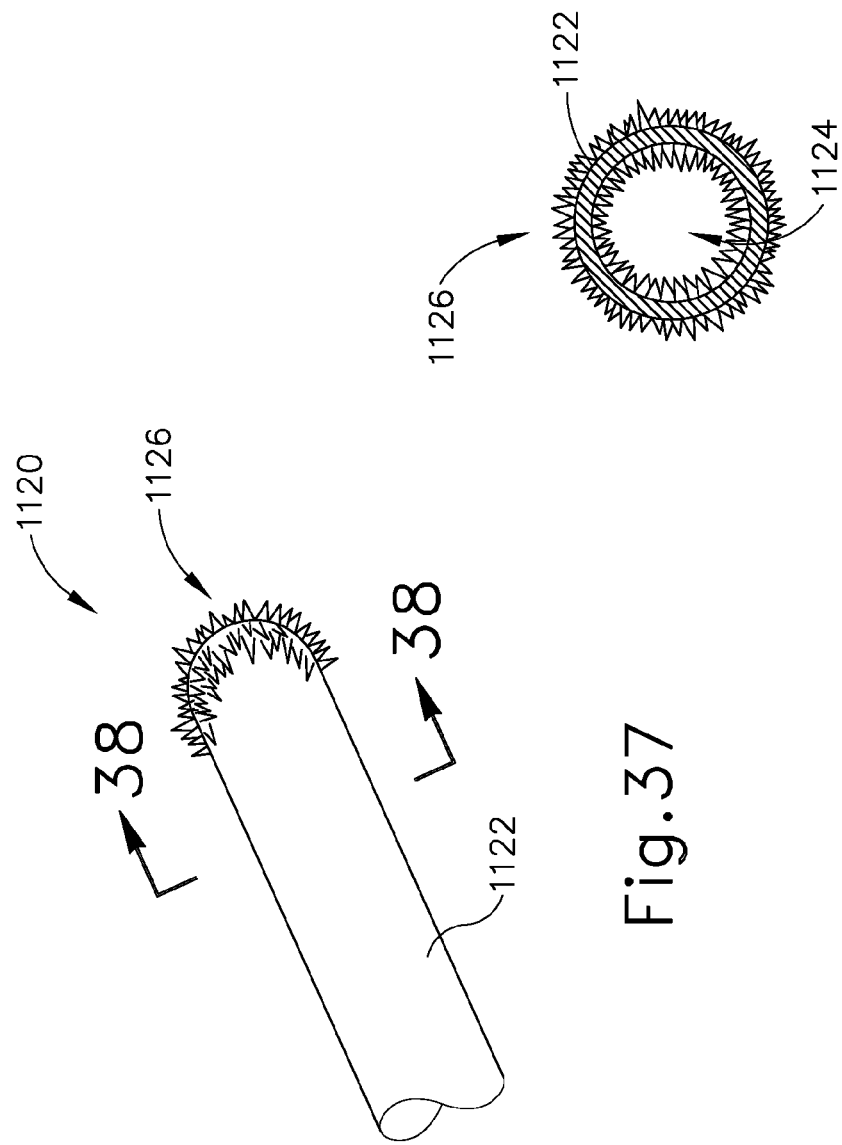

ULTRASONIC SURGICAL INSTRUMENT WITH INTEGRAL BLADE CLEANING FEATURE

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the surgeon's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein; and U.S. patent application Ser. No. 14/031,665, entitled "Alignment Features for Ultrasonic Surgical Instrument," filed Sep. 19, 2013, published as U.S. Pub. No. 2015/0080925 on Mar. 19, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued Aug. 4, 2015, the disclosure of which is incorporated by reference herein.

Some ultrasonic surgical instruments may include a clamp feature to press tissue against the ultrasonic blade of the end effector. Examples of such an arrangement (sometimes referred to as a clamp coagulator shears or an ultrasonic transector) is disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; and U.S. Pat. No. 6,325,811, entitled "Blades with Functional Balance Asymmetries for use with Ultrasonic Surgical Instruments," issue Dec. 4, 2001, the disclosure of which is incorporated by reference herein. Some versions of clamp coagulator shears utilize handles that are either of a pistol or scissors grips design. The scissor grip designs may have one thumb or finger grip that is immovable and fixed to the housing; and one movable thumb or finger grip. Some designs have scissor arms that extend from the grips, with one of the arms rotating around a fixed pivot or rotation point that is perpendicular to the longitudinal axis of the working element. The operator may thus squeeze a handgrip or other feature to drive a clamp arm, to thereby press the clamp pad toward the blade.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16 depicts a perspective view of an end effector of yet another exemplary alternative surgical instrument;

FIG. 17A depicts a cross-sectional view of the instrument of FIG. 16 with a clamp arm of the instrument in a first position;

FIG. 17B depicts a cross-sectional view of the instrument of FIG. 16 with the clamp arm of FIG. 17A moved to a second position;

FIG. 30A depicts a perspective view of the end cap of FIG. 29 positioned on the end of yet another exemplary alternative instrument;

FIG. 35 depicts a side elevational view of an exemplary cleaning instrument;

FIG. 36 depicts a cross-sectional view of the cleaning instrument of FIG. 35 taken along line 36-36 of FIG. 35;

FIG. 37 depicts a side elevational view of an exemplary alternative cleaning instrument;

FIG. 38 depicts a cross-sectional view of the cleaning instrument of FIG. 35 taken along line 38-38 of FIG. 37;

Figure 1:
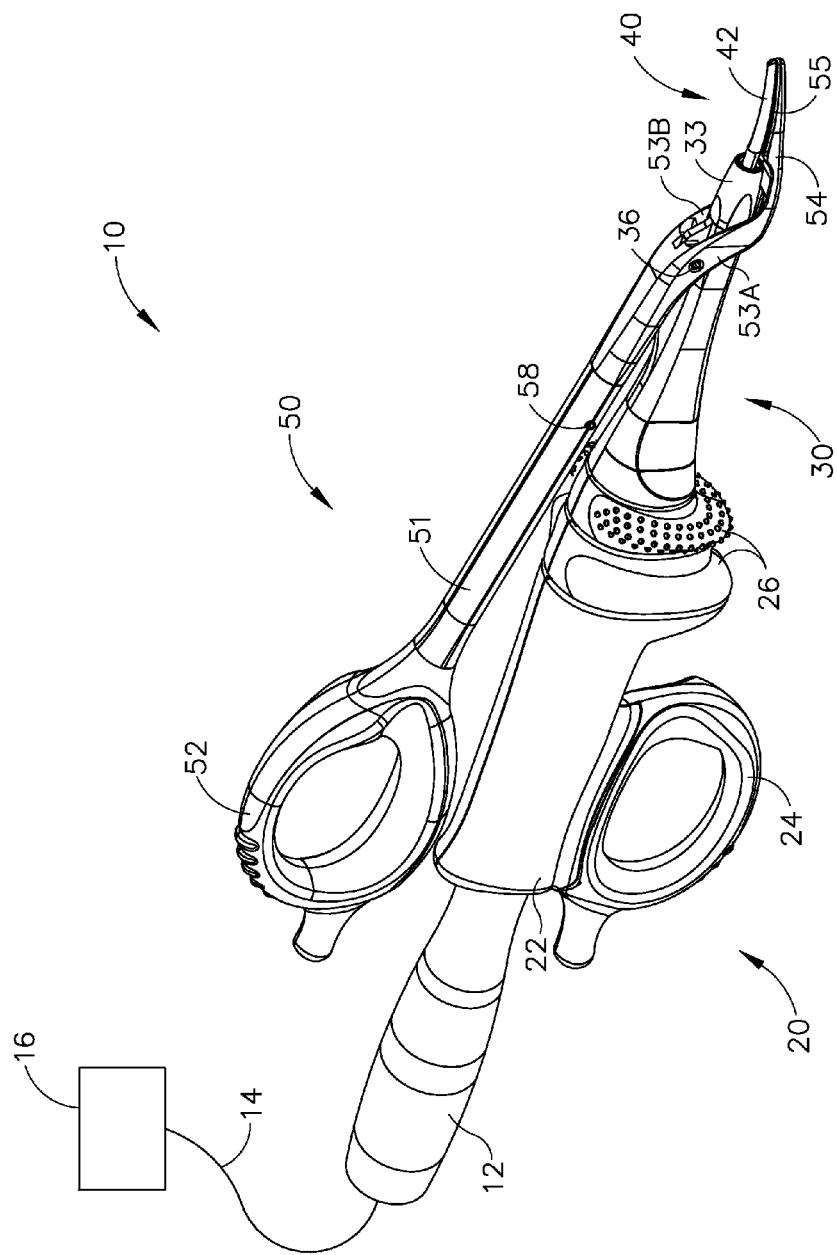
FIG. 1 depicts a perspective view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. patent application Ser. No. 13/538,588, now U.S. Pat. No. 9,393,037; U.S. patent application Ser. No. 13/657,553, now U.S. Pat. No. 9,095,367; U.S. Pat. App. No. 61/410,603; and/or U.S. patent application Ser. No. 14/031,665, published as U.S. Pub. No. 2015/0080925. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously, using a combination of compression and ultrasonic vibrational energy. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 3:
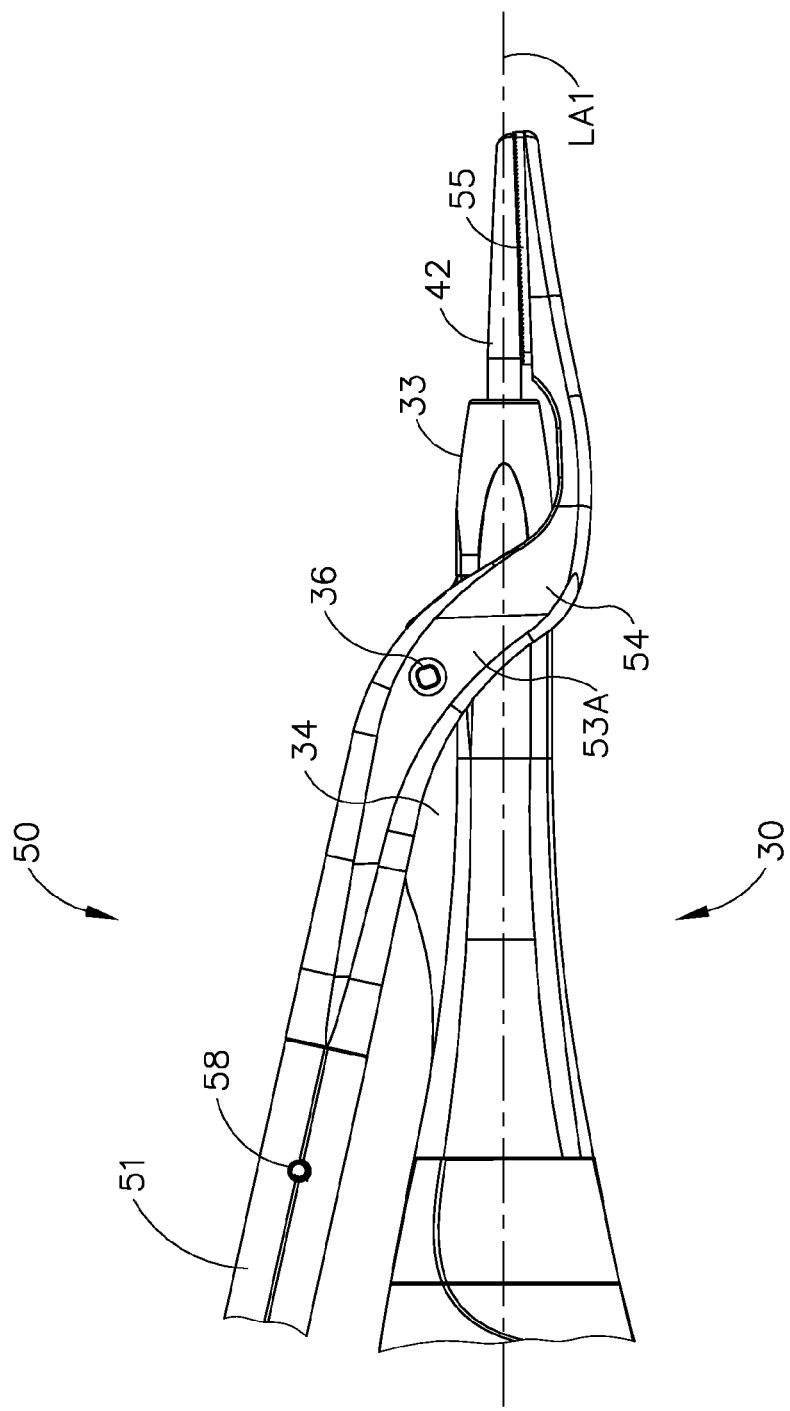
FIG. 3 depicts a side elevational view of the end effector of the instrument of FIG. 1.

Instrument (10) of the present example comprises a handpiece (20), a shaft assembly (30), and an end effector (40). Handpiece (20) comprises a body (22) including a finger grip (24) and a pair of buttons (26). Instrument (10) also includes a clamp arm assembly (50) that is pivotable toward and away from body (22). A proximal portion of clamp arm assembly (50) comprises a thumb grip (52). Thumb grip (52) and finger grip (24) together provide a scissor grip type of configuration. It should be understood, however, that various other suitable configurations may be used, including but not limited to a pistol grip configuration. A cap (33) is secured to a distal end of shaft assembly (30). End effector (40) includes an ultrasonic blade (42) extending distally from cap (33) of shaft assembly (30); and a pivoting clamp arm (54), which is an integral feature of clamp arm assembly (50). Clamp arm assembly (50) is pivotably coupled to a projection (34) extending laterally from shaft assembly (30) via a pivot member (36) (e.g., a pin, bearing, shaft, etc.) such that clamp arm (54) is pivotable toward and away from ultrasonic blade (42) to thereby clamp tissue between a clamp pad (55) of clamp arm (54) and ultrasonic blade (42). As best seen in FIG. 3, clamp arm assembly (50) is pivotably coupled to projection (34) such that clamp arm assembly (50) pivots about an axis offset from a longitudinal axis (LA1). It should be understood that such rotation about an offset axis may allow for a narrower shaft assembly (30) profile. It should be understood that shaft assembly (30) passes through a portion of clamp arm assembly (50) such that as clamp arm assembly (50) rotates, clamp arm (54) rotates about a portion of shaft assembly (30). In particular, a first member (53A) and a second member (53B) of clamp arm assembly (50) are disposed about a distal portion of shaft assembly (30).

Figure 2:
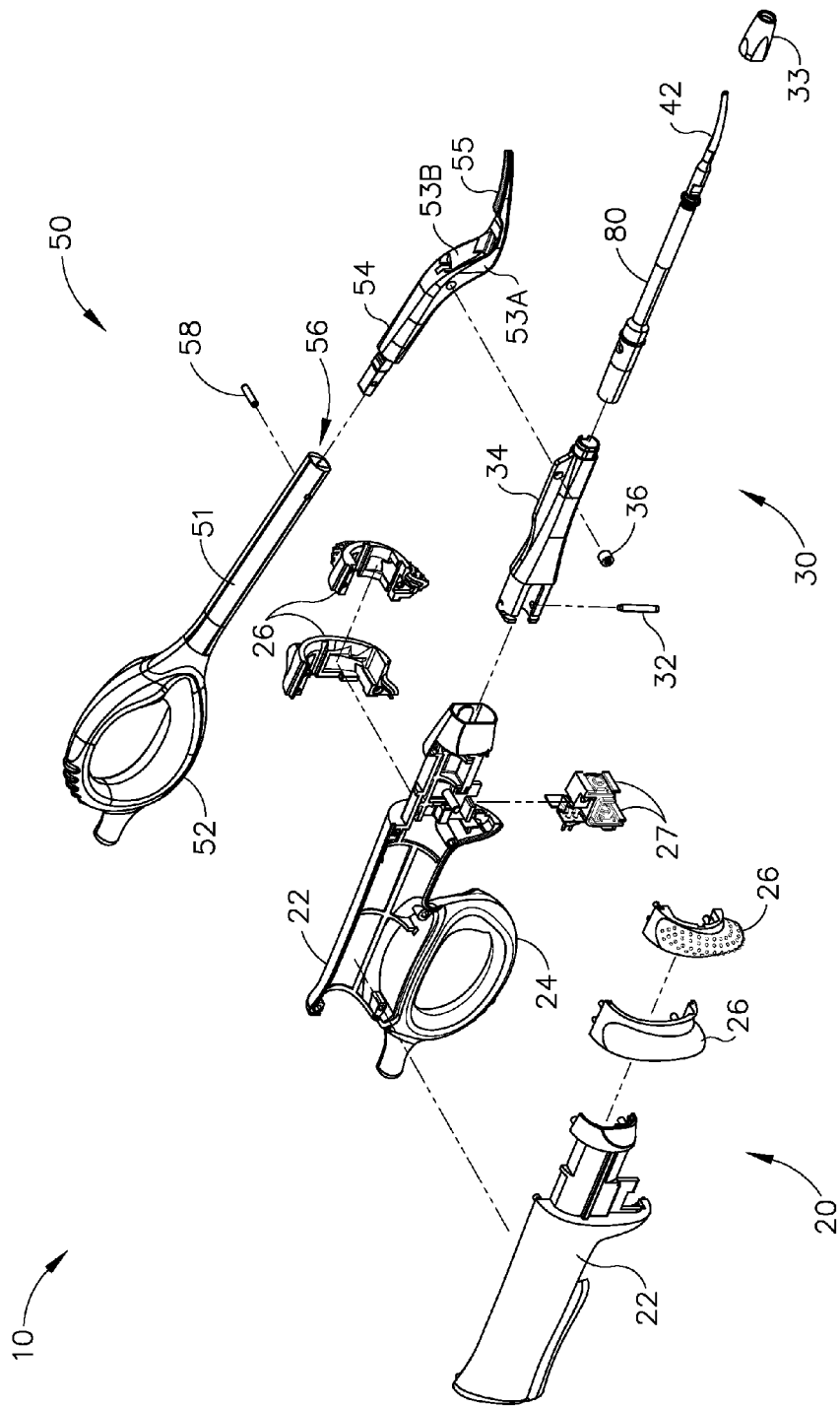
FIG. 2 depicts an exploded perspective view of the instrument of FIG. 1.

Clamp arm assembly (50) is configured such that clamp arm (54) is pivotable toward ultrasonic blade (42) in response to pivoting of thumb grip (52) of clamp arm assembly (50) toward body (22); and such that clamp arm (54) is pivotable away from ultrasonic blade (42) in response to pivoting of thumb grip (52) of clamp arm assembly (50) away from body (22). As best seen in FIG. 2, a proximal end of clamp arm (54) is disposed within a distal recess (56) of a shank portion (51) of clamp arm assembly (50); and is secured therein by a pin (58). Various other suitable ways in which clamp arm (54) may be integrated into clamp arm assembly (50) will be apparent to those of ordinary skill in the art in view of the teachings herein. In some versions, one or more resilient members are used to bias clamp arm (54) and/or trigger (28) to the open position shown in FIG. 1. By way of example only, such a resilient member may comprise a leaf spring, a torsion spring, and/or any other suitable kind of resilient member.

As shown in FIG. 1, an ultrasonic transducer assembly (12) extends proximally from body (22) of handpiece (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handpiece (20), and that handpiece (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (80), which extends through shaft assembly (30) to reach ultrasonic blade (42) as shown in FIG. 2. Waveguide (80) is secured within shaft assembly (30) via a pin (32), which passes through waveguide (80) and shaft assembly (30). Pin (32) is located at a position along the length of waveguide (80) corresponding to a node associated with resonant ultrasonic vibrations communicated through waveguide (80). As noted above, when ultrasonic blade (42) is in an activated state (i.e., vibrating ultrasonically), ultrasonic blade (42) is operable to effectively cut through and seal tissue, particularly when the tissue is being clamped between clamp arm (54) and ultrasonic blade (42). It should be understood that waveguide (80) may be configured to amplify mechanical vibrations transmitted through waveguide (80). Furthermore, waveguide (80) may include features operable to control the gain of the longitudinal vibrations along waveguide (80) and/or features to tune waveguide (80) to the resonant frequency of the system.

In the present example, the distal end of ultrasonic blade (42) is located at a position corresponding to an anti-node associated with resonant ultrasonic vibrations communicated through waveguide (80), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (42), thereby providing oscillation of ultrasonic blade (42) at the resonant ultrasonic frequency. Thus, when tissue is secured between ultrasonic blade (42) and clamp arm (54), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and clamp arm (54) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

An operator may activate buttons (26) to selectively close switches (27) (see FIG. 2), thereby selectively activating transducer assembly (12) to activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb in the ring formed by thumb grip (52), position their middle or ring finger in the ring formed by finger grip (24), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. patent application Ser. No. 13/538,588, now U.S. Pat. No. 9,393,037; U.S. patent application Ser. No. 13/657,553, now U.S. Pat. No. 9,095,367; and/or U.S. patent application Ser. No. 14/031,665, published as U.S. Pub. No. 2015/0080925. Additional merely illustrative variations for instrument (10) will be described in greater detail below. It should be understood that the below described variations may be readily applied to instrument (10) described above and any of the instruments referred to in any of the references that are cited herein, among others.

II. Exemplary Sealing Elements

Figure 4:
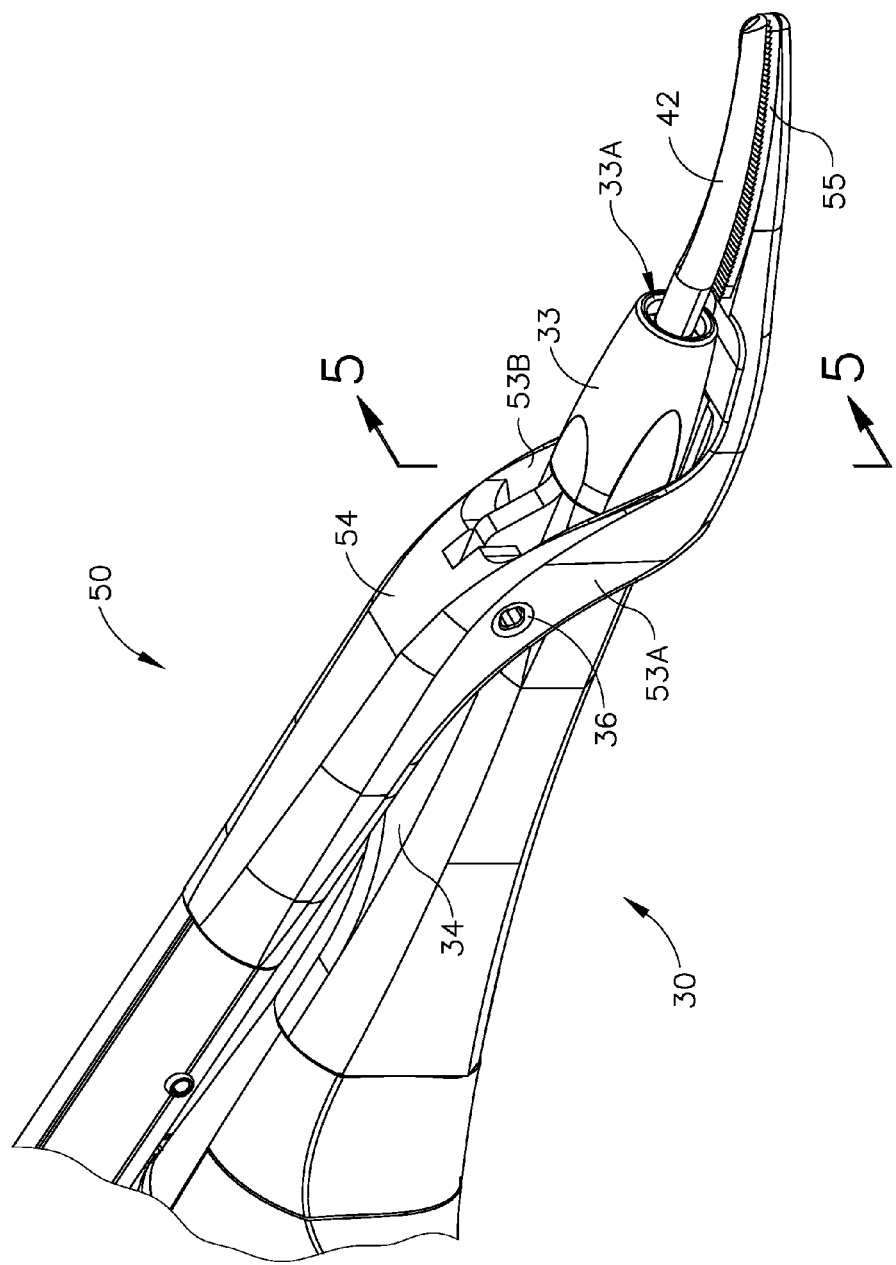
FIG. 4 depicts a perspective view of the end effector of the instrument of FIG. 1.

As shown in FIG. 4, an opening (33A) exists at a distal end of shaft assembly (30) between an exterior surface of ultrasonic blade (42) and an interior surface of cap (33). Opening (33A) provides access to an interior cavity of shaft assembly (30). The interior cavity is defined between an interior surface of shaft assembly (30) (including cap (33)) and exterior surfaces of waveguide (80) and ultrasonic blade (42). It may be desirable to provide features that seal this interior cavity such that surgical debris (e.g. tissue, coagulated blood, etc.), body fluid, etc. is prevented from entering. In particular, it may be desirable to provide a seal that extends between the exterior surface of waveguide (80) and/or ultrasonic blade (42) and the interior surface of cap (33). Although the examples of radial seals discussed below are discussed as contacting one or both of the exterior surfaces of waveguide (80) and/or ultrasonic blade (42), it should be understood that any radial seal discussed below may contact either or both of the exterior surfaces of waveguide (80) and/or ultrasonic blade (42).

A. First Exemplary Sealing Feature

Figure 5:
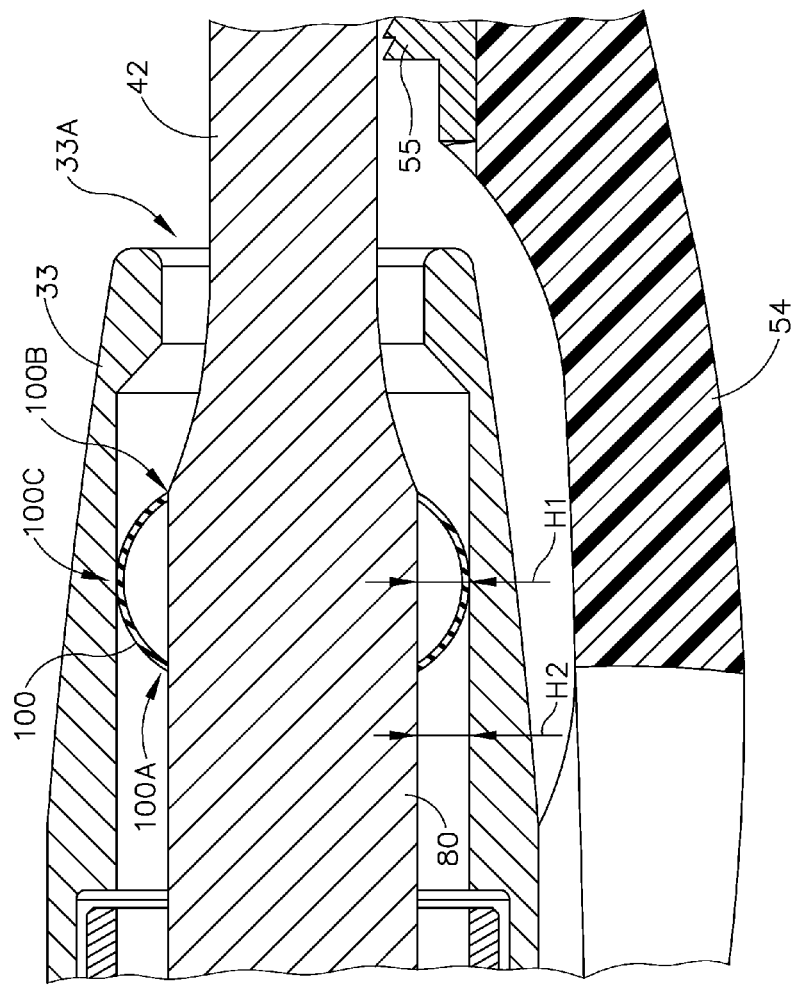
FIG. 5 depicts a partial cross-sectional view of a variation of the instrument of FIG. 1 having an exemplary sealing element.

An example of a radial seal (100) is shown in FIG. 5. Radial seal (100) comprises a circular-resilient member having a semi-circular cross-sectional profile. The semi-circular cross-sectional profile of radial seal (100) presents a concave interior surface and a convex exterior surface. Radial seal (100) contacts the exterior surface of waveguide (80) along a pair of edges (100A, 100B) of radial seal (100). Radial seal (100) contacts the interior surface of cap (33) at an apex (100C) of the exterior convex surface of radial seal (100). It should be understood that these contact points extend completely circumferentially about the exterior surface of waveguide (80) and the interior surface of cap (33).

Radial seal (100) defines a height (H1) between pair of edges (100A, 100B) and apex (100C). The interior cavity of shaft assembly (30) has a height (H2) represented by the distance between the exterior surface of waveguide (80) and the interior surface of cap (33). When placed within opening (33A), radial seal (100) flexes to assume height (H2) of the interior cavity of shaft assembly (30). Radial seal (100) may be configured such that height (H1) of radial seal (100) is greater than height (H2) of the interior cavity of shaft assembly (30). Furthermore, radial seal (100) may be resiliently biased to return to height (H1). It should be understood that this bias would cause radial seal (100) to apply force to the exterior surface of waveguide (80) via pair of edges (100A, 100B) and to the interior surface of cap (33) via apex (100C). It should further be understood that the resilient bias of radial seal (100) may be changed to apply more or less force to the exterior surface of waveguide (80) and/or the interior surface of cap (33). Radial seal (100) may be configured and positioned such that pair of edges (100A, 100B) contacts waveguide (80) at a node associated with resonant ultrasonic vibrations communicated through waveguide (80) and ultrasonic blade (42). Alternatively, radial seal (100) may be configured and positioned such that pair of edges (100A, 100B) contacts waveguide (80) away from a node associated with resonant ultrasonic vibrations communicated through waveguide (80) and ultrasonic blade (42).

As will be appreciated form the discussion below, in some versions of instrument (10), radial seal (100) may be configured to be longitudinally translatable such that pair of edges (100A, 100B) and/or apex (100C) of radial seal (100) may be used as a cleaning element to drive surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)).

Although radial seal (100) of the present example contacts the exterior surface of waveguide (80), it should be understood that radial seal (100) may alternatively contact the exterior surface of ultrasonic blade (42).

B. Second Exemplary Sealing Feature

Figure 6:
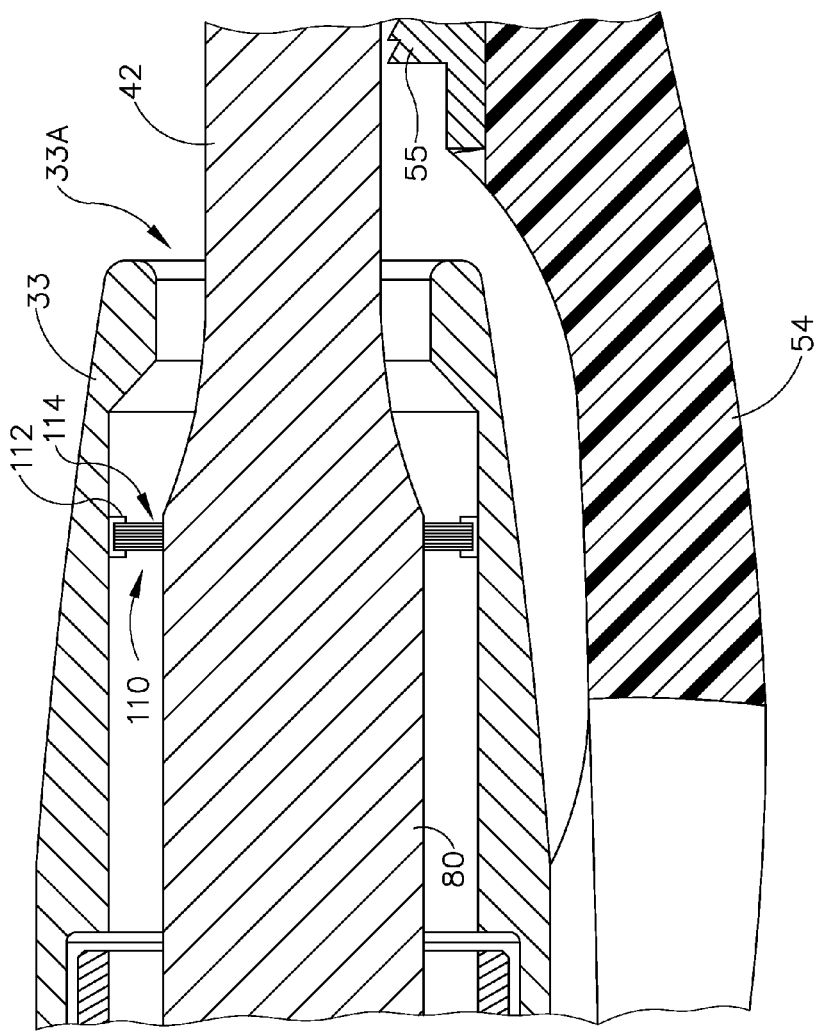
FIG. 6 depicts a partial cross-sectional view of a variation of the instrument of FIG. 1 having an exemplary alternative sealing element.

FIG. 6 shows an exemplary alternative radial seal (110) that is configured to extend between the exterior surface of waveguide (80) and the interior surface of cap (33) to thereby seal the interior cavity of shaft assembly (30). Radial seal (110) comprises a circular base (112) and a plurality of bristles (114). An exterior surface of circular base (112) is secured to the interior surface of cap (33). Bristles (114) are secured to an interior surface of base (112) and extend inwardly to the exterior surface of waveguide (80). It should be understood, however, that radial seal (110) may be reconfigured such that the exterior surface of circular base (112) may be secured to the exterior surface of waveguide (80), with bristles (114) extending outwardly to the interior surface of cap (33). It should be understood that solid and/or semi-solid surgical debris (e.g. tissue, coagulated blood, etc.) may not pass through bristles (114) while fluid may still pass through bristles (114). Bristles (114) may comprise nylon and/or another other appropriate material. A stiffness of each bristle (114) may be changed to thereby prevent more or less material from passing through. Also, bristles (114) may be arranged in a more or less dense configuration to thereby prevent more or less material from passing through. Radial seal (110) may be positioned such that bristles (114) contact waveguide (80) at a node associated with resonant ultrasonic vibrations communicated through waveguide (80) and ultrasonic blade (42). Alternatively, radial seal (110) may be positioned such that bristles (114) contacts waveguide (80) away from a node associated with resonant ultrasonic vibrations communicated through waveguide (80) and ultrasonic blade (42).

As will be appreciated form the discussion below, in some versions of instrument (10), radial seal (110) may be configured to be longitudinally translatable such that bristles (114) of radial seal (110) may be used as a cleaning element to drive surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)).

Although radial seal (110) of the present example contacts the exterior surface of waveguide (80), it should be understood that radial seal (110) may alternatively contact the exterior surface of ultrasonic blade (42).

C. Third Exemplary Alternative Sealing Feature

Figure 7:
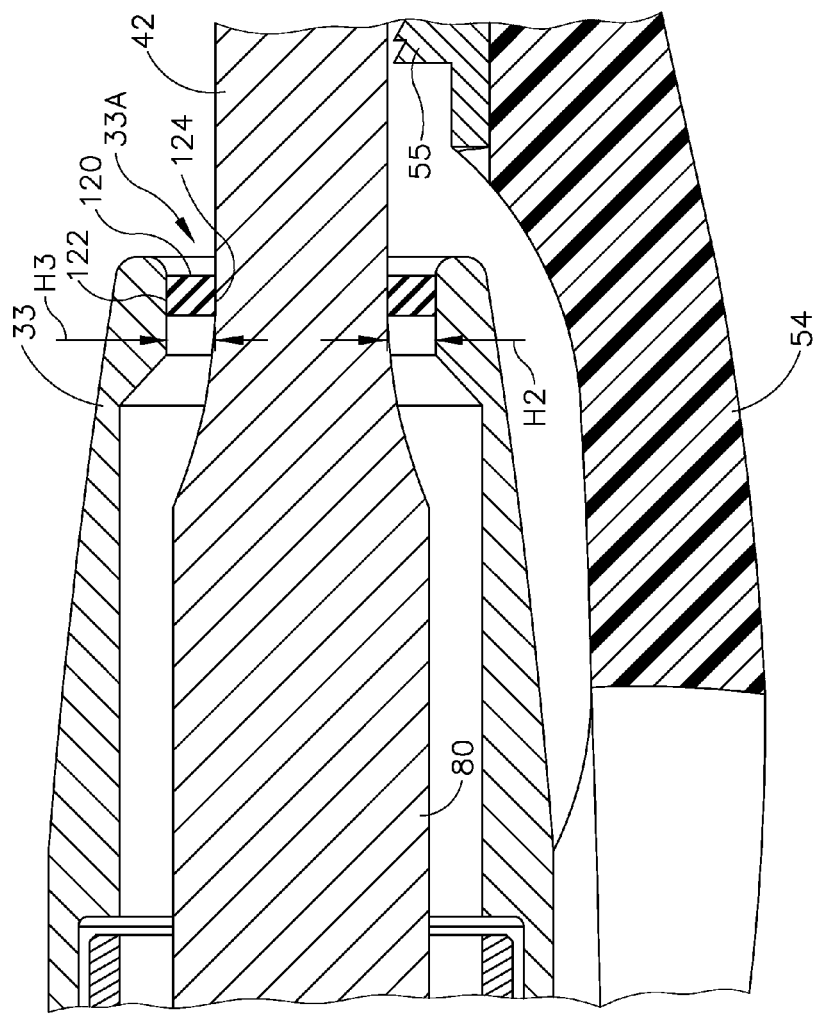
FIG. 7 depicts a partial cross-sectional view of a variation of the instrument of FIG. 1 having another exemplary alternative sealing element.

FIG. 7 shows another exemplary alternative radial seal (120) that is configured to extend between the exterior surface of ultrasonic blade (42) and the interior surface of cap (33) to thereby seal the interior cavity of shaft assembly (30). Radial seal (120) comprises a circular member made of an absorbent material having a rectangular cross-sectional profile. Radial seal (120) is sized such that an exterior surface (122) of radial seal (120) contacts the interior surface of cap (33) and such that an interior surface (124) of radial seal (120) contacts the exterior surface of ultrasonic blade (42). The absorbent material of radial seal (120) may comprise felt and/or any other appropriate material. The absorbent material of radial seal (120) may be porous such that solid and/or semi-solid surgical debris may not pass through radial seal (120) whereas fluid may still pass through radial seal (120). A density of the absorbent material of radial seal (120) may be changed to thereby prevent more or less material from passing through. It should be understood that radial seal (120) may comprise a nonabsorbent/nonporous material to thereby prevent all surgical debris, body fluid, etc. from entering the interior cavity of shaft assembly (30).

Radial seal (120) defines a height (H3) between interior surface (124) and exterior surface (122). As previously discussed, the interior cavity of shaft assembly (30) has a height (H2) represented by the distance between the exterior surface of ultrasonic blade (42) and the interior surface of cap (33). Radial seal (120) of the present example comprises a flexible material. When placed within opening (33A), radial seal (120) flexes to assume height (H2) of the interior cavity of shaft assembly (30). Radial seal (120) may be configured such that height (H3) of radial seal (120) is greater than height (H2) of the interior cavity of shaft assembly (30). Furthermore, the flexible material of radial seal (120) may cause radial seal (120) to be resiliently biased to return to height (H3). It should be understood that this bias would cause radial seal (120) to apply force to the exterior surface of ultrasonic blade (42) via interior surface (124) and to the interior surface of cap (33) via exterior surface (122). It should further be understood that the resilient bias of radial seal (120) may be changed by changing the flexible material to apply more or less force to the exterior surface of ultrasonic blade (42) and/or the interior surface of cap (33). Radial seal (120) may be positioned such that interior surface (124) contacts ultrasonic blade (42) at a node associated with resonant ultrasonic vibrations communicated through waveguide (80) and ultrasonic blade (42). Alternatively, radial seal (120) may be positioned such that interior surface (124) contacts ultrasonic blade (42) away from a node associated with resonant ultrasonic vibrations communicated through waveguide (80) and ultrasonic blade (42).

As will be appreciated form the discussion below, in some versions of instrument (10), radial seal (120) may be configured to be longitudinally translatable such that exterior surface (122) and/or interior surface (124) of radial seal (120) may be used as a cleaning element to drive surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)).

Although radial seal (120) of the present example contacts the exterior surface of ultrasonic blade (42), it should be understood that radial seal (120) may alternatively contact the exterior surface of waveguide (80).

D. Fourth Exemplary Sealing Feature

Figure 8:
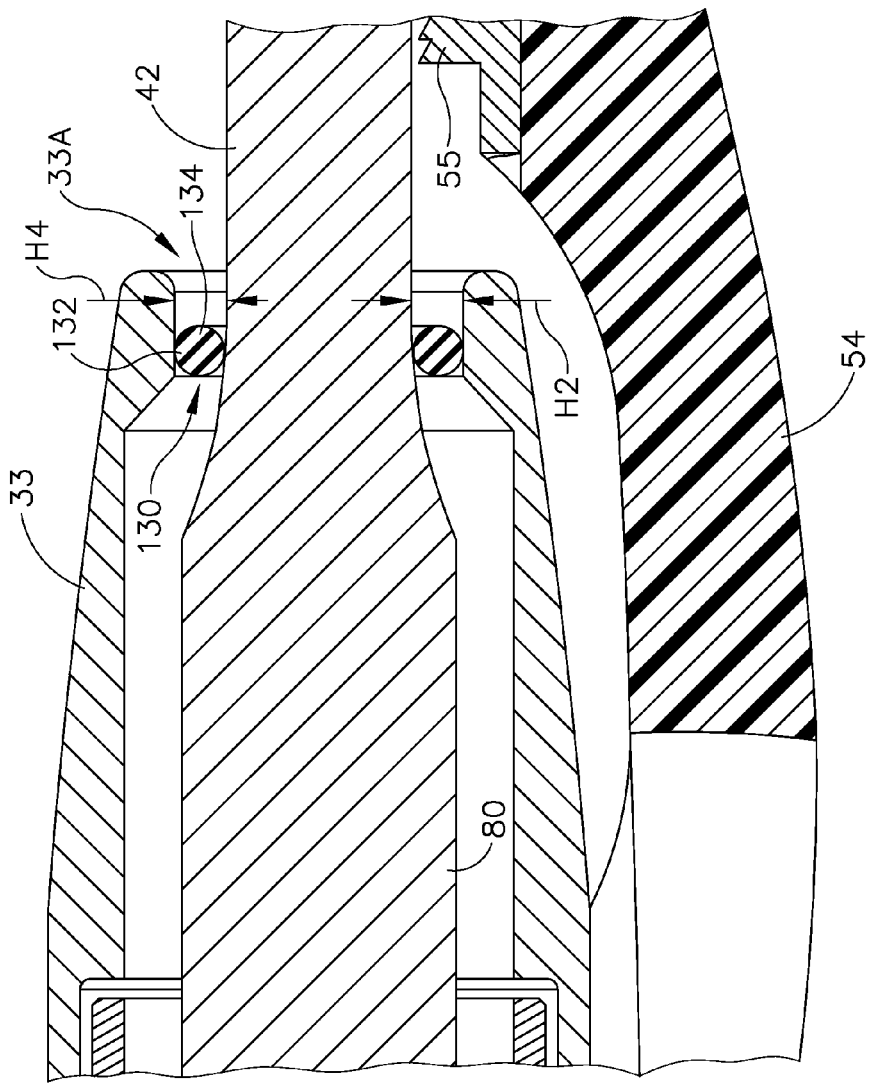
FIG. 8 depicts a partial cross-sectional view of a variation of the instrument of FIG. 1 having yet another exemplary alternative sealing element.

FIG. 8 shows another exemplary alternative radial seal (130) that is configured to extend between the exterior surface of ultrasonic blade (42) and the interior surface of cap (33) to thereby seal the interior cavity of shaft assembly (30). Radial seal (130) comprises a circular member made of a flexible material having a circular cross-sectional profile (e.g. similar to an o-ring). Radial seal (130) is sized such that an exterior surface (132) of radial seal (130) contacts the interior surface of cap (33) and such that an interior surface (134) of radial seal (130) contacts the exterior surface of ultrasonic blade (42). Radial seal (130) defines a height (H4) between an inner most point of interior surface (130) and an outer most point of exterior surface (132). As previously discussed, the interior cavity of shaft assembly (30) has a height (H2) represented by the distance between the exterior surface of ultrasonic blade (42) and the interior surface of cap (33). When placed within opening (33A), radial seal (130) flexes to assume height (H2) of the interior cavity of shaft assembly (30). Radial seal (130) may be configured such that height (H4) of radial seal (130) is greater than height (H2) of the interior cavity of shaft assembly (30). Furthermore, the flexible material of radial seal (130) may cause radial seal (130) to be resiliently biased to return to height (H4). It should be understood that this bias would cause radial seal (130) to apply force to the exterior surface of ultrasonic blade (42) via interior surface (134) and to the interior surface of cap (33) via exterior surface (132). It should further be understood that the resilient bias of radial seal (130) may be changed by changing the flexible material to apply more or less force to the exterior surface of ultrasonic blade (42) and/or the interior surface of cap (33). Radial seal (130) may be positioned such that interior surface (134) contacts ultrasonic blade (42) at a node associated with resonant ultrasonic vibrations communicated through waveguide (80) and ultrasonic blade (42). Alternatively, radial seal (130) may be positioned such that interior surface (134) contacts ultrasonic blade (42) away from a node associated with resonant ultrasonic vibrations communicated through waveguide (80) and ultrasonic blade (42).

As will be appreciated form the discussion below, in some versions of instrument (10), radial seal (130) may be configured to be longitudinally translatable such that exterior surface (132) and/or interior surface (134) of radial seal (130) may be used as a cleaning element to drive surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)).

Although radial seal (130) of the present example contacts the exterior surface of ultrasonic blade (42), it should be understood that radial seal (130) may alternatively contact the exterior surface of waveguide (80).

E. Fifth Exemplary Sealing Feature

Figure 9:
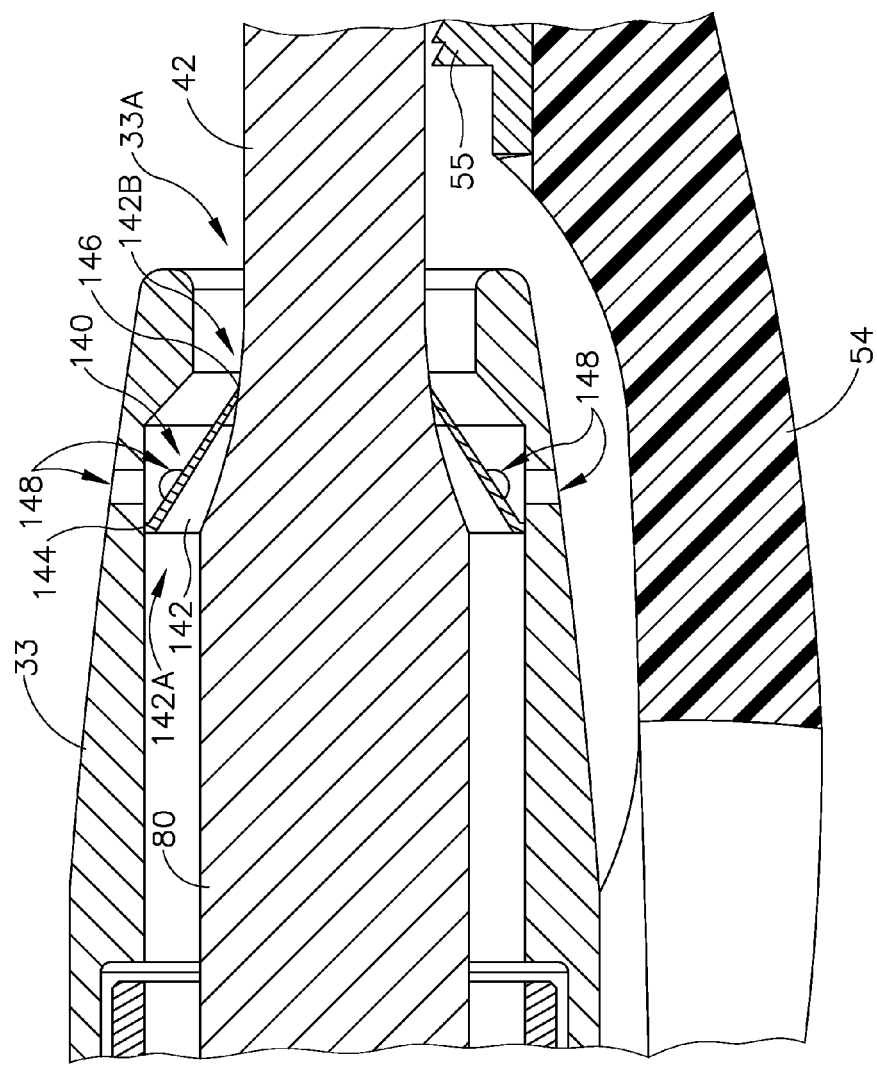
FIG. 9 depicts a partial cross-sectional view of a variation of the instrument of FIG. 1 having yet another exemplary alternative sealing element.

FIG. 9 shows another exemplary alternative radial seal (140) that is configured to extend between the exterior surface of ultrasonic blade (42) and the interior surface of cap (33) to thereby seal the interior cavity of shaft assembly (30). Radial seal (140) comprises a conical member (142). A first end (142A) of conical member (142) comprises a first radial circumference. A second end (142B) of conical member (142) comprises a second radial circumference. The first radial circumference of first end (142A) is greater than the second radial circumference of second end (142B). Conical member (142) is oriented within the interior cavity of shaft assembly (30) such that first end (142A) of conical member (142) is proximal of second end (142B) of conical member (142). A lip (144) projects from an exterior surface of first end (142A) of conical member (142). Conical member (142) is sized such that lip (144) of conical member (142) contacts the interior surface of cap (33) and such that an edge (146) of second end (142B) of conical member (142) contacts the exterior surface of ultrasonic blade (42). Conical member (142) may be biased to apply force upon to the exterior surface of ultrasonic blade (42) via edge (146) and to the interior surface of cap (33) via lip (144), such that conical member (142) substantially seals the region of the interior cavity of shaft assembly (30) proximal of conical member (142).

Cap (33) of the present example comprises a plurality of openings (148). Openings (148) pass completely through cap (33). Openings (148) may comprise discrete circular openings and/or slots that extend along the circumference of cap (33) to any suitable extent. Openings (148) are formed in cap (33) distally of lip (144) such that the interior cavity of shaft assembly (30) remains sealed. As surgical debris, body fluid, etc. enters the interior cavity of shaft assembly (30) via opening (33A), the exterior surface of conical member (142) guides surgical debris, body fluid, etc. toward openings (148). Openings (148) allow for fluid to pass through into a distal portion of the interior cavity of cap (33) to thereby drive surgical debris, body fluid, etc. from the interior cavity of cap (33).

Conical member (142) may be positioned such that edge (146) contacts ultrasonic blade (42) at a node associated with resonant ultrasonic vibrations communicated through waveguide (80) and ultrasonic blade (42). Alternatively, conical member (142) may be positioned such that edge (146) contacts ultrasonic blade (42) away from a node associated with resonant ultrasonic vibrations communicated through waveguide (80) and ultrasonic blade (42).

As will be appreciated form the discussion below, in some versions of instrument (10), radial seal (140) may be configured to be longitudinally translatable such that lip (144) and/or edge (146) of conical member (142) may be used as a cleaning element to drive surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)).

Although conical member (142) of the present example contacts the exterior surface of ultrasonic blade (42), it should be understood that conical member (142) may alternatively contact the exterior surface of waveguide (80).

F. Sixth Exemplary Sealing Feature

Figure 10:
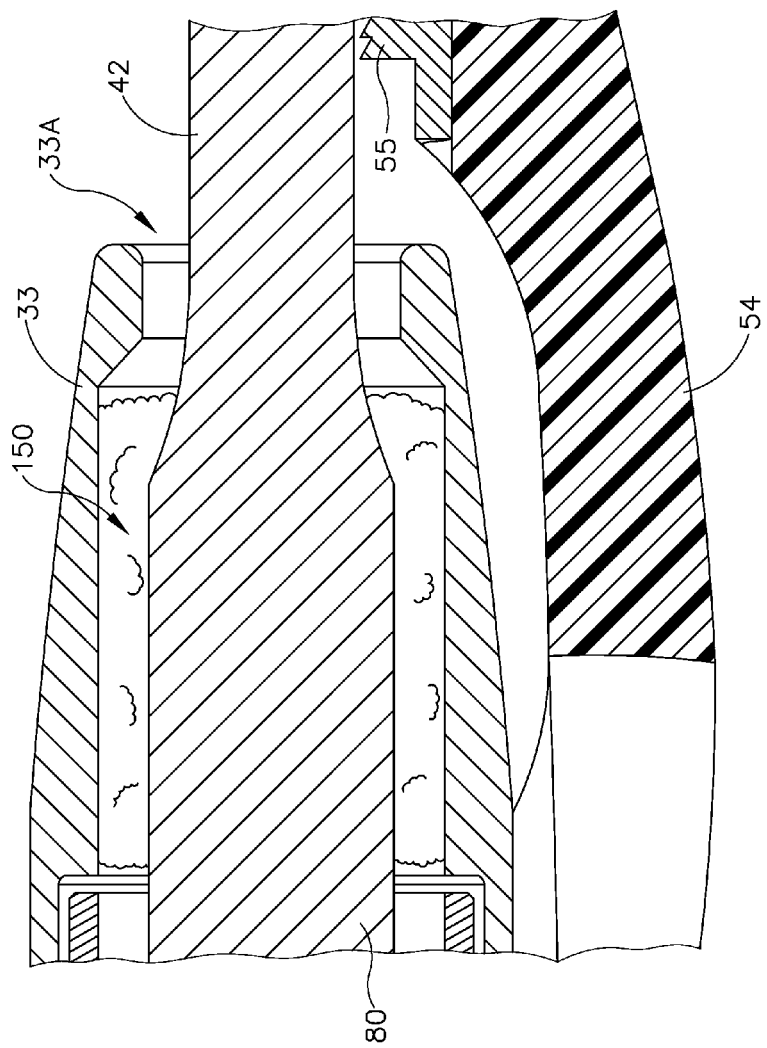
FIG. 10 depicts a partial cross-sectional view of a variation of the instrument of FIG. 1 having yet another exemplary alternative sealing element.

FIG. 10 shows another exemplary alternative radial seal (150) that is configured to extend between the exterior surfaces of waveguide (80) and ultrasonic blade (42) and the interior surface of cap (33) to thereby seal the interior cavity of shaft assembly (30). Radial seal (150) comprises a soft material disposed within the interior cavity of shaft assembly (30). The soft material of radial seal (140) may be configured to not interrupt or significantly dampen the ultrasonic vibrations communicated through waveguide (80). The soft material of radial seal (150) prevents surgical debris, body fluid, etc. from passing into the interior cavity of shaft assembly (30) and from contacting waveguide (80) and ultrasonic blade (42) along the portions of waveguide (80) and ultrasonic blade (42) covered by the soft material of radial seal (150). The soft material of radial seal (150) may comprise liquid repellant material to discourage accumulation of liquid within the interior cavity of shaft assembly (30). The soft material of radial seal (150) may be porous such that solid and/or semi-solid surgical debris may not pass through radial seal (150) whereas fluid may still pass through radial seal (150). A density of the soft material of radial seal (150) may be changed to thereby prevent more or less material from passing through.

Radial seal (150) may be removed from the interior cavity of shaft assembly (30) after use such that surgical debris, body fluid, etc. caught within the soft material of radial seal (150) may be removed from the interior cavity of shaft assembly (30). Thus, it should be understood that radial seal (150) may be used as a cleaning element to remove surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)).

III. Exemplary Cleaning Elements

As previously discussed, opening (33A) provides access to an interior cavity of shaft assembly (30). In addition to or in lieu of sealing off such a cavity, it may be desirable to provide cleaning elements that allow a user to drive surgical debris, body fluid, etc. from the interior cavity of shaft assembly (30) (including cap (33)) and/or clean the exterior surface of waveguide (80), ultrasonic blade (42), and/or the interior surface of shaft assembly (30) (including cap (33)). Various examples of features that may be used to clean surgical debris, body fluid, etc. from the interior cavity of shaft assembly (30) will be described in greater detail below, while other examples will be apparent to those of ordinary skill in the art in view of the teachings herein.

A. First Exemplary Cleaning Element

Figure 11:
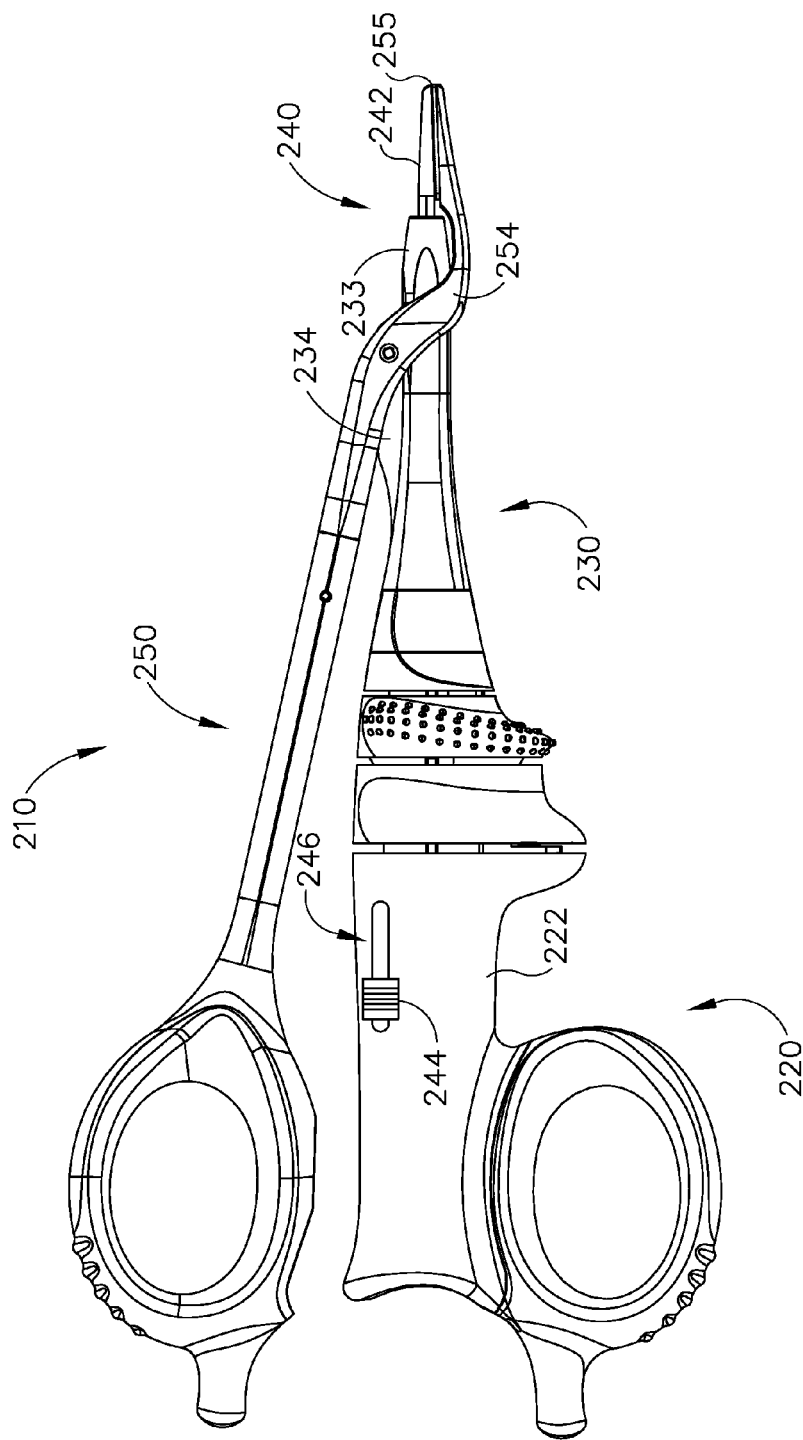
FIG. 11 depicts a side elevational view of an exemplary alternative surgical instrument.
Figure 12A:
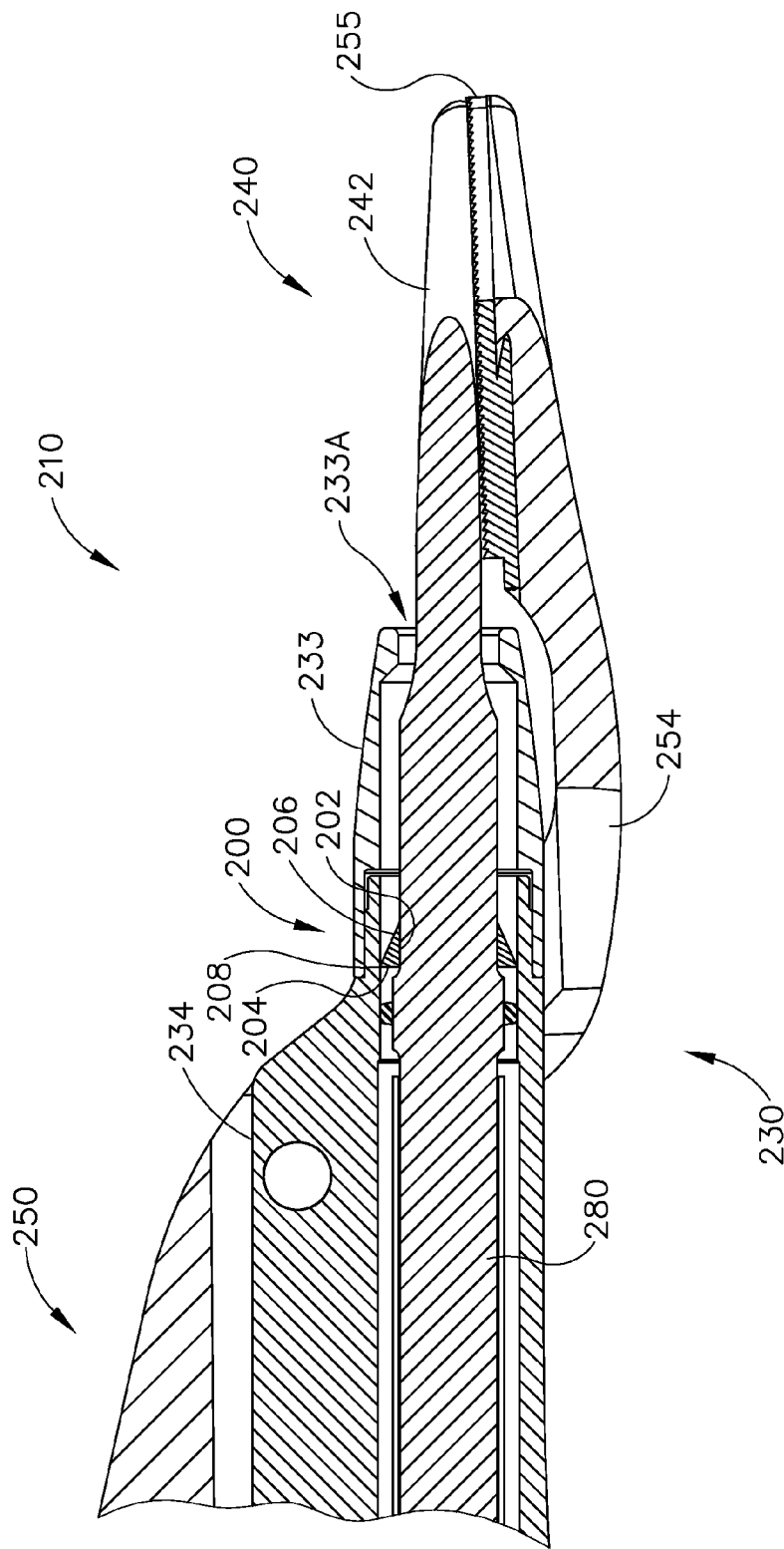
FIG. 12A depicts a cross-sectional view of the instrument of FIG. 11 with a cleaning element in a first longitudinal position.
Figure 12B:
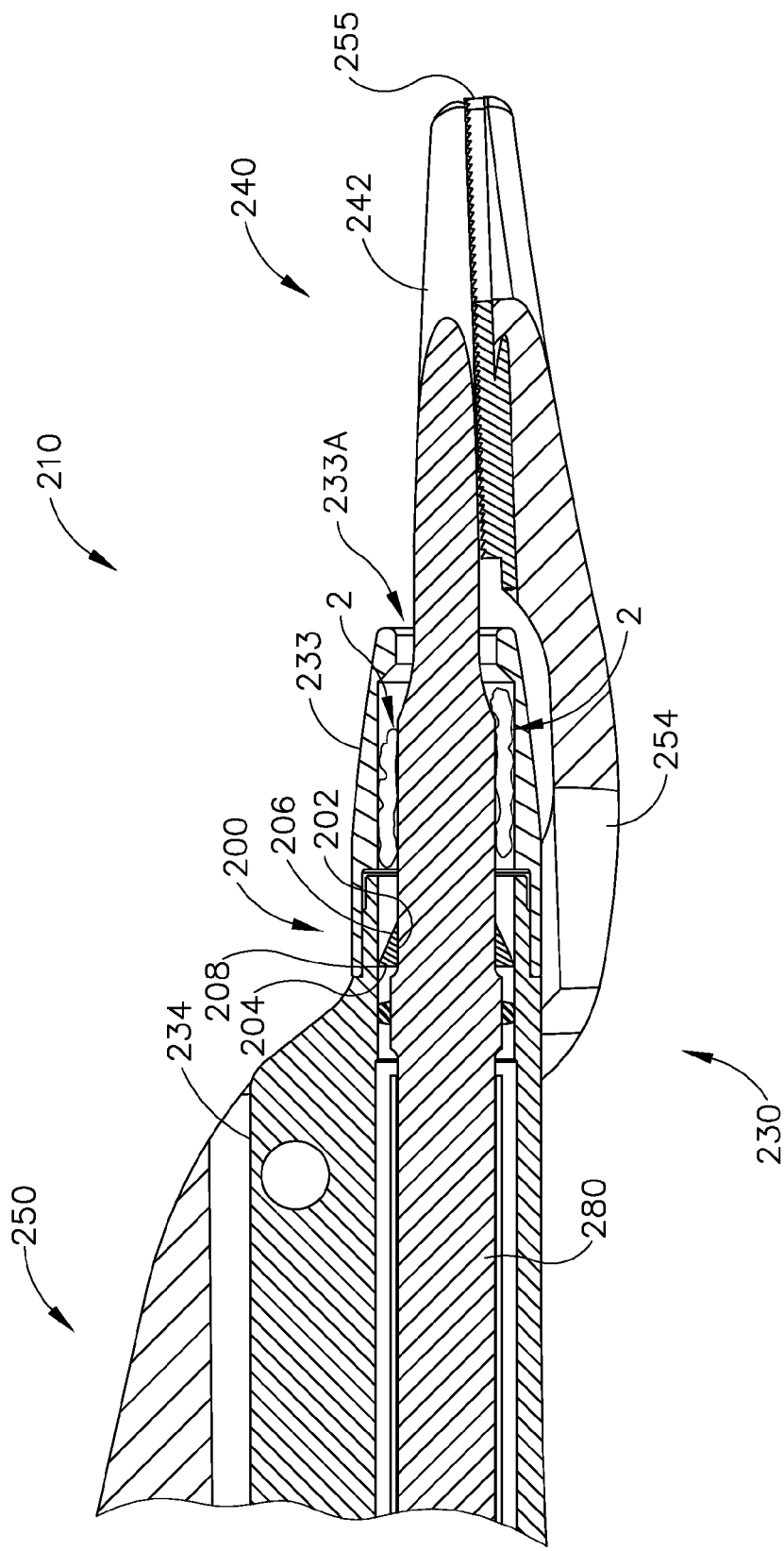
FIG. 12B depicts a cross-sectional view of the instrument of FIG. 11 with the cleaning element of FIG. 12A still in the first longitudinal position, and with tissue disposed within an end effector of the instrument.
Figure 12C:
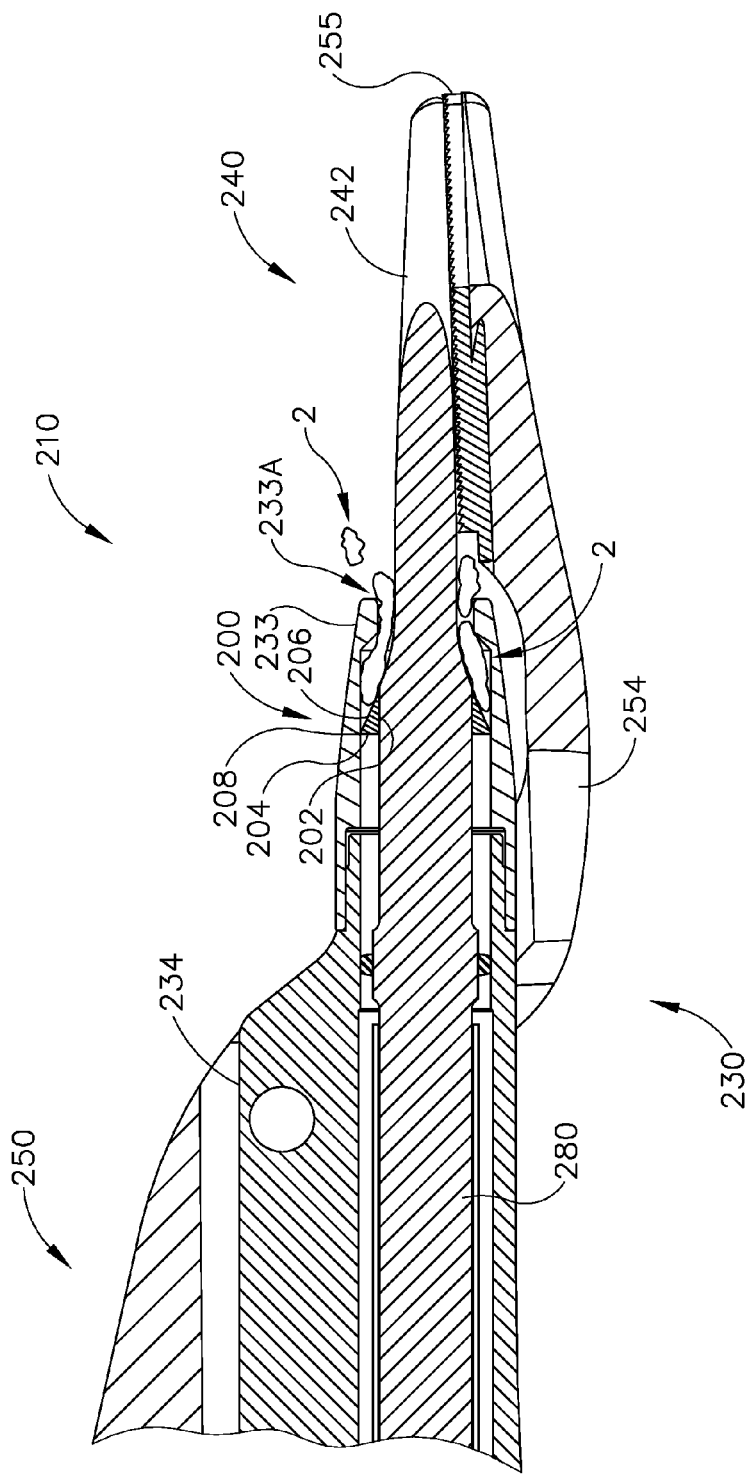
FIG. 12C depicts a cross-sectional view of the instrument of FIG. 11 with the cleaning element of FIG. 12A moved to a second longitudinal position, and with the tissue being forced from the end effector of the instrument.
Figure 12D:
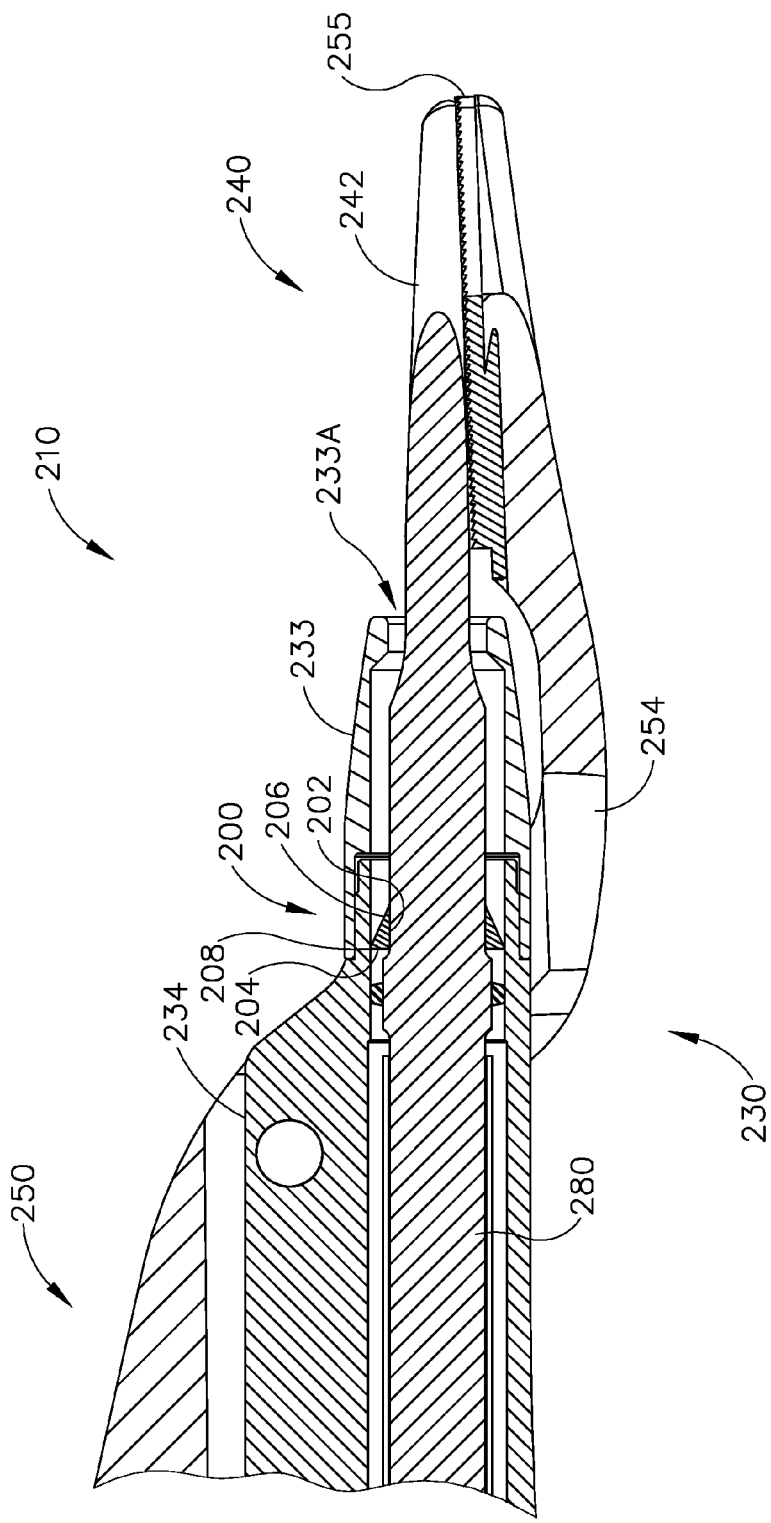
FIG. 12D depicts a cross-sectional view of the instrument of FIG. 11 with the cleaning element of FIG. 12A moved back to the first longitudinal position.

FIGS. 11-12D show one merely illustrative example of an instrument (210) with a cavity cleaning element (200). Instrument (210) of the present example is configured to operate substantially similar to instrument (10) discussed above except for the differences discussed below.

As shown in FIG. 11, instrument (210) of the present example comprises a handpiece (220), a shaft assembly (230), and an end effector (240). Handpiece (220) comprises a body (222). Instrument (210) also includes a clamp arm assembly (250) that is pivotable toward and away from body (222). A cap (233) is secured to a distal end of shaft assembly (230). End effector (240) includes an ultrasonic blade (242) extending distally from cap (233) of shaft assembly (230); and a pivoting clamp arm (254), which is an integral feature of clamp arm assembly (250). Clamp arm assembly (250) is pivotably coupled to a projection (234) extending laterally from shaft assembly (230) such that clamp arm (254) is pivotable toward and away from ultrasonic blade (242) to thereby clamp tissue between a clamp pad (255) of clamp arm (254) and ultrasonic blade (242). Ultrasonic vibrations that are generated by a transducer assembly (not shown) are communicated along an acoustic waveguide (280), which extends through shaft assembly (230) to reach ultrasonic blade (242). Ultrasonic blade (242) vibrates at ultrasonic frequencies to cut and/or seal tissue.

As shown in FIGS. 12A-12D, cleaning element (200) comprises a circular member having a triangular cross-sectional profile. An interior surface (202) of cleaning element (200) contacts an exterior surface of waveguide (280). A proximal surface (204) of cleaning element (200) extends perpendicularly from a proximal end of interior surface (202) to an interior surface of cap (233). A distal surface (206) of cleaning element (200) extends angularly from a proximal end of interior surface (202) to the interior surface of cap (233). Proximal surface (204) and distal surface (206) come together and form an edge (208) that contacts the interior surface of cap (233). It should be understood that the contact between interior surface (202) of cleaning element (200) and the contact between edge (208) of cleaning element (200) extend completely circumferentially about the exterior surface of waveguide (280) and the interior surface of cap (233). It should further be understood that edge (208) may resiliently bear against the interior surface of cap (233) and/or that interior surface (202) may resiliently bear against the exterior surface of waveguide (280). Furthermore, cleaning element (200) need not be limited to a circular shape. Any other suitable shapes/configurations may be used.

Returning to FIG. 11, instrument (210) comprises a sliding trigger (244). Sliding trigger (244) is longitudinally translatable between a proximal position and a distal position within a longitudinal slot (246) formed in body (222). Cleaning element (200) is mechanically connected with sliding trigger (244) such that longitudinal translation of sliding trigger (244) causes concurrent longitudinal translation of cleaning element (200). Thus, it should be understood that interior surface (202) and edge (208) of cleaning element (200) act as wipers to clean the exterior surface of waveguide (280) and/or the interior surface of cap (233). Furthermore, as will be discussed in more detail below, longitudinal translation of cleaning element (200) drives surgical debris, body fluid, etc. from an interior cavity of shaft assembly (230). Various suitable ways in which sliding trigger (244) may be coupled within cleaning element (200) will be apparent to those of ordinary skill in the art in view of the teachings herein.

FIG. 12A shows cleaning element (200) in a proximal position. In the proximal position, surgical debris (e.g. tissue, coagulated blood, etc.) and/or body fluid (2) may enter into the interior cavity of shaft assembly (230) via an opening (233A) at a distal end of cap (233) as shown in FIG. 12B. When surgical debris and/or body fluid (2) becomes disposed within the interior cavity of shaft assembly (230), the user may translate cleaning element (200) longitudinally distally by translating sliding trigger (244) longitudinally distally. As shown in FIG. 12C, longitudinal distal translation of cleaning element (200) to a distal position drives surgical debris and/or body fluid (2) distally from the interior cavity of shaft assembly (230), out through opening (233A), and thereby cleans the interior surface of cap (233) and/or the exterior surface of waveguide (280). Once surgical debris and/or body fluid (2) has been driven from the interior cavity of shaft assembly (230), cleaning element (200) may be moved back to the proximal position as shown in FIG. 12D by translating sliding trigger (244) longitudinally proximally.

Instrument (210) may be configured such that cleaning element (200) contacts waveguide (280) at a node associated with resonant ultrasonic vibrations communicated through waveguide (280) and ultrasonic blade (242) when cleaning element (200) is in the proximal position. Alternatively, instrument (210) may be configured such that cleaning element (200) contacts waveguide (280) away from a node associated with resonant ultrasonic vibrations communicated through waveguide (280) and ultrasonic blade (242) when cleaning element (200) is in the proximal position. Although cleaning element (200) of the present example contacts the exterior surface of waveguide (280), it should be understood that cleaning element (200) may alternatively contact the exterior surface of ultrasonic blade (242).

B. Second Exemplary Cleaning Element

Figure 13:
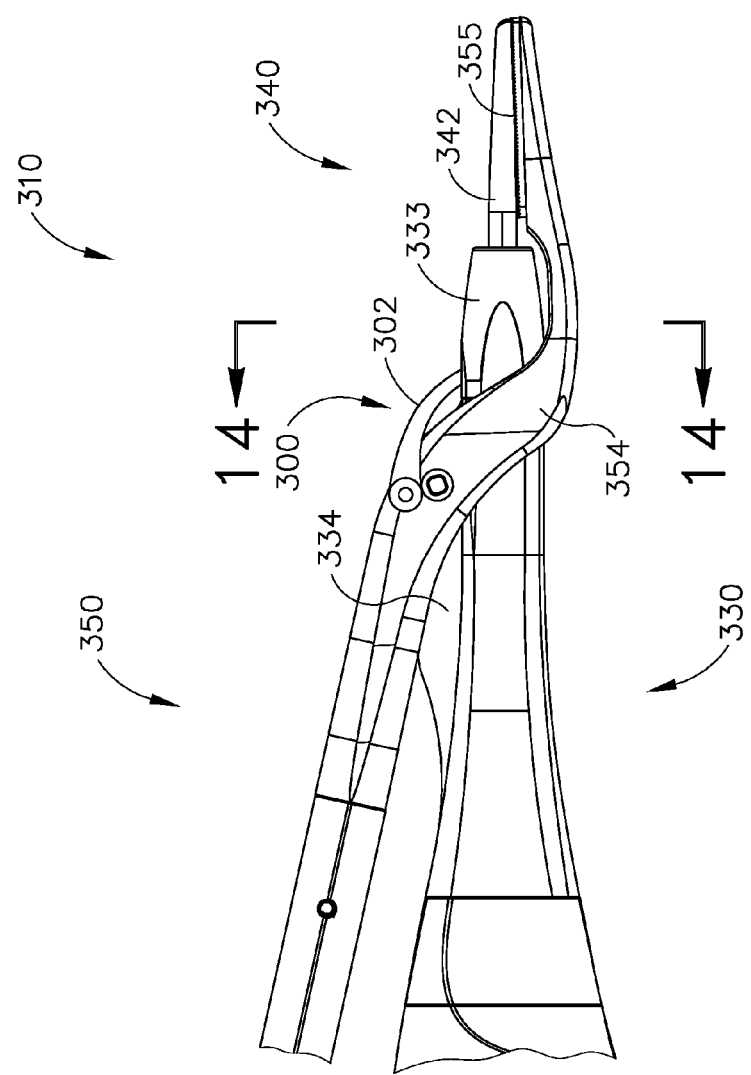
FIG. 13 depicts a perspective view of an end effector of another exemplary alternative surgical instrument.

FIGS. 13-15B show an exemplary alternative instrument (310) with a cleaning element (300) configured to clean and/or drive surgical debris, body fluid, etc. from the interior cavity of a shaft assembly (330). Instrument (310) of the present example is configured to operate substantially similar to instruments (10, 210) discussed above except for the differences discussed below. As shown in FIG. 13, instrument (310) of the present example comprises a shaft assembly (330) and an end effector (340). Instrument (310) also includes a clamp arm assembly (350) that is pivotable toward and away from shaft assembly (330). A cap (333) is secured to a distal end of shaft assembly (330). End effector (340) includes an ultrasonic blade (342) extending distally from cap (333) of shaft assembly (330); and a pivoting clamp arm (354), which is an integral feature of clamp arm assembly (350). Clamp arm assembly (350) is pivotably coupled to a projection (334) extending laterally from shaft assembly (330) such that clamp arm (354) is pivotable toward and away from ultrasonic blade (342) to thereby clamp tissue between a clamp pad (355) of clamp arm (354) and ultrasonic blade (342). Ultrasonic vibrations that are generated by a transducer assembly (not shown) are communicated along an acoustic waveguide (380), which extends through shaft assembly (330) to reach ultrasonic blade (342). Ultrasonic blade (342) vibrates at ultrasonic frequencies to cut and/or seal tissue.

Figure 14:
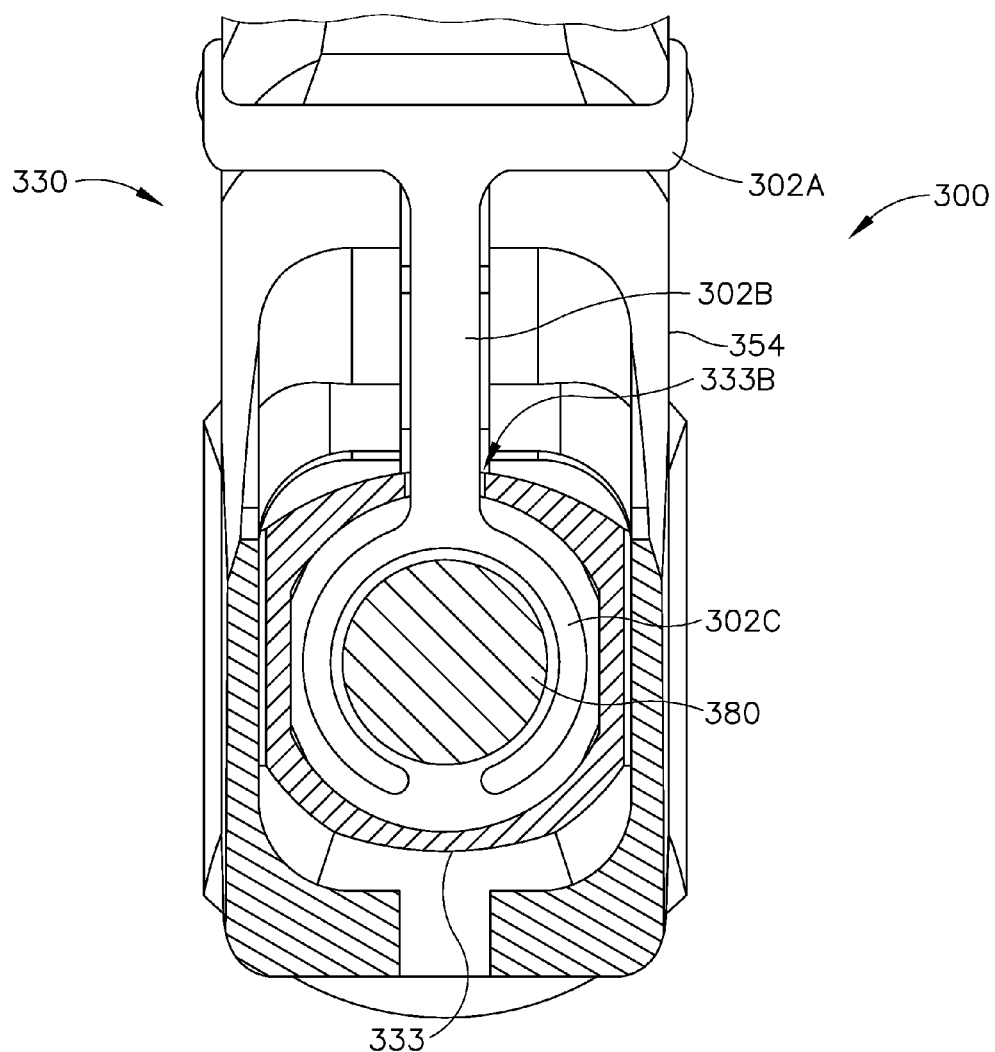
FIG. 14 depicts a cross-sectional view of the end effector of FIG. 13 taken along line 14-14 of FIG. 13.
Figure 15A:
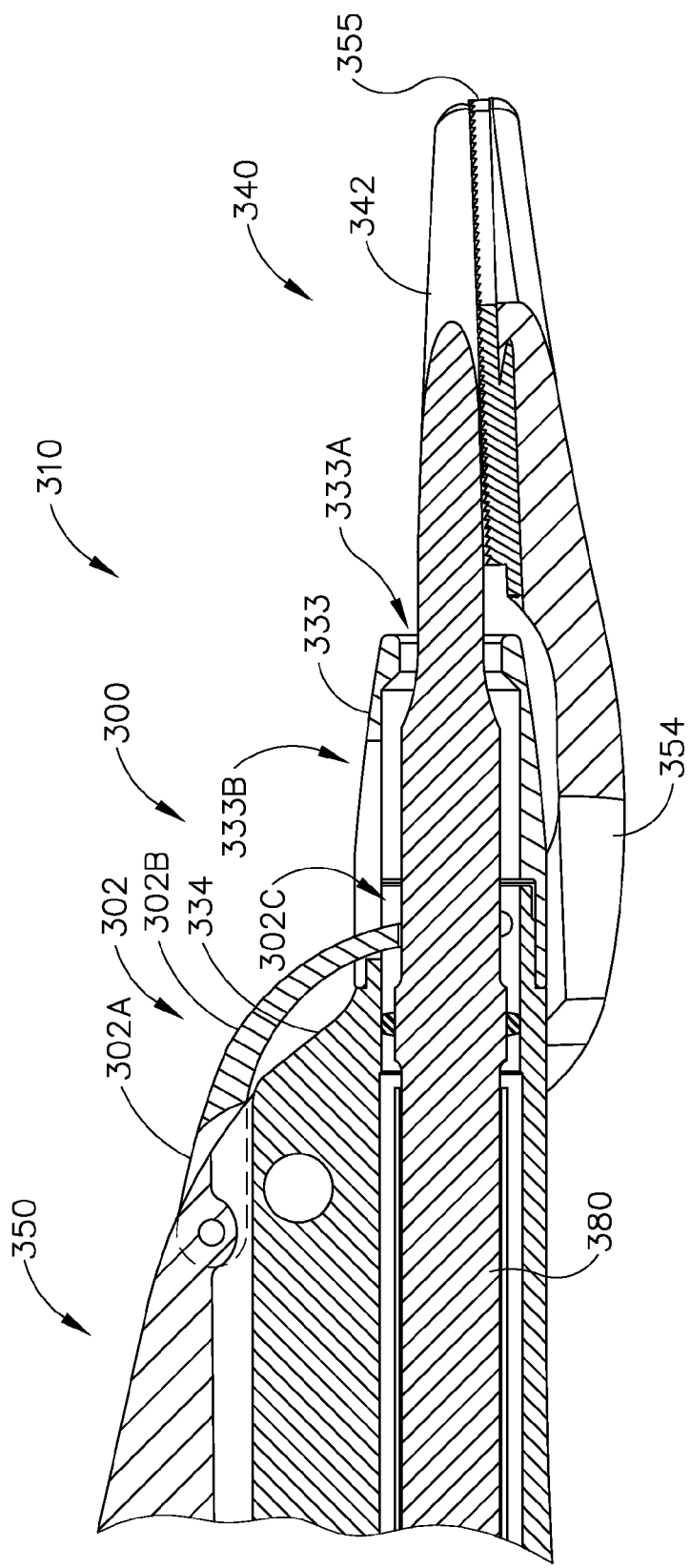
FIG. 15A depicts a cross-sectional view of the instrument of FIG. 13 with an exemplary alternative cleaning element in a first position.
Figure 15B:
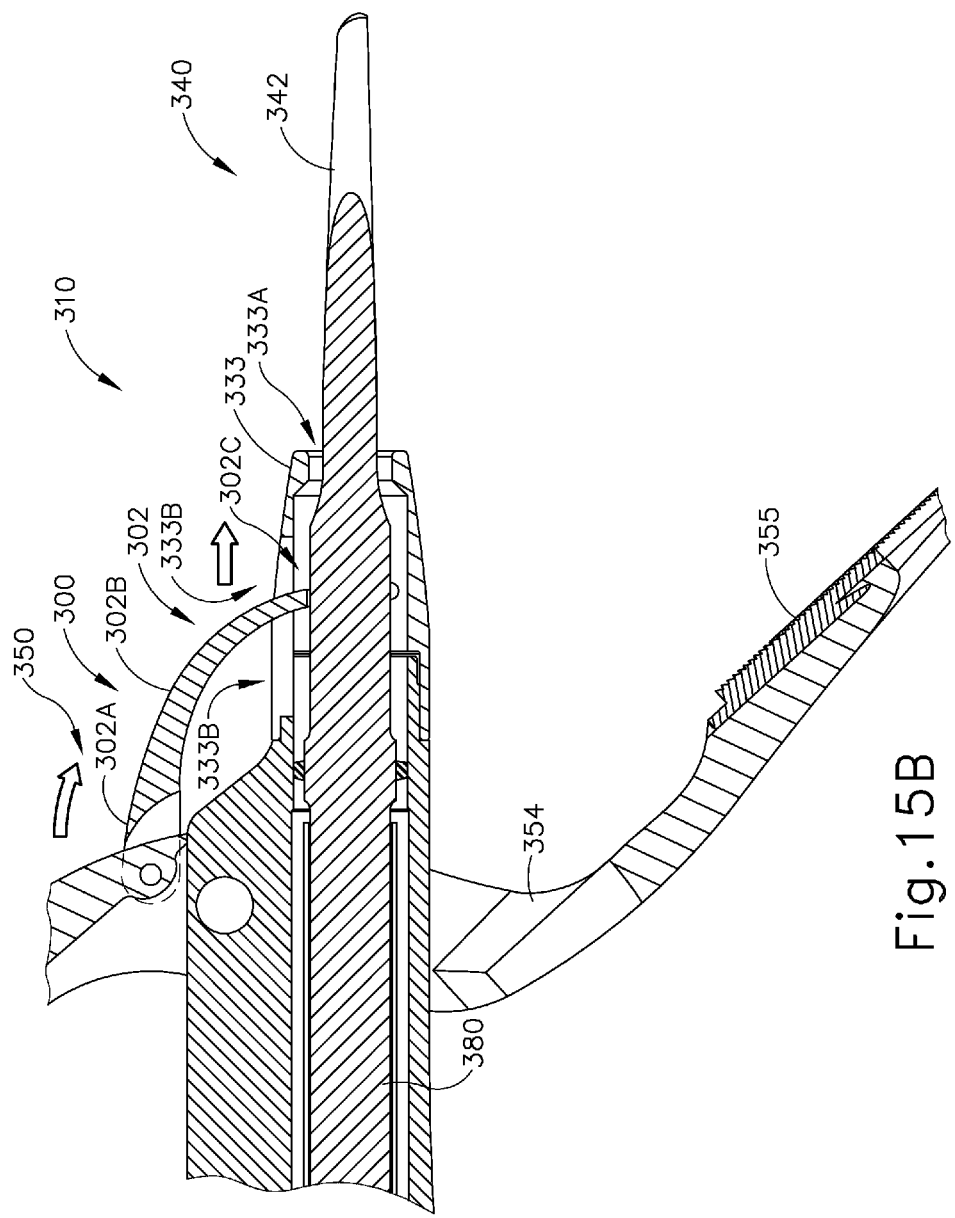
FIG. 15B depicts a cross-sectional view of the instrument of FIG. 13 with the cleaning element of FIG. 15A moved to a second position.

As shown in FIGS. 14-15B, cleaning element (300) comprises a body (302) pivotably coupled to clamp arm (354). Body (302) comprises a first yoke portion (302A), a curved neck (302B), and a second yoke portion (302C). First yoke portion (302A) is pivotably coupled with clamp arm (354). Curved neck (302B) extends proximally and downwardly from first yoke portion (302A). Curved neck (302B) passes through a longitudinal slot (333B) formed in a top surface of cap (333). Second yoke portion (302C) extends downwardly from a portion of curved neck (302B) disposed within an interior cavity of shaft assembly (330). Second yoke portion (302C) is shaped to complement an exterior surface of waveguide (380) and the interior surface of cap (333). In particular, second yoke portion (302C) is a C-shape and is disposed about waveguide (380). As best seen in FIG. 14, second yoke portion (302C) is slidably coupled about waveguide (380).

FIG. 15A shows cleaning element (300) in a proximal position. Cleaning element (300) in the proximal position corresponds to clamp arm (354) being pivoted toward ultrasonic blade (342) such that clamp pad (355) of clamp arm (354) contacts ultrasonic blade (342). With cleaning element (300) in the proximal position, surgical debris, body fluid, etc. may enter into the interior cavity of shaft assembly (330) via an opening (333A) at a distal end of cap (333). As shown in FIG. 15B, as clamp arm (354) is rotated away from ultrasonic blade (342), because second yoke portion (302C) of body (302) of cleaning element (300) is slidably coupled about waveguide (342), cleaning element (300) does not rotate with clamp arm (354). Instead, as clamp arm (354) rotates away from ultrasonic blade (342), cleaning element (300) rotates away from clamp arm (354) and second yoke portion (302C) of body (302) of cleaning element (300) is translated longitudinally distally within the interior cavity of shaft assembly (330). This longitudinal distal translation of second yoke portion (302C) to a distal position drives surgical debris, body fluid, etc. from the interior cavity of shaft assembly (330) and may clean the interior surface of cap (333) and/or the exterior surface of waveguide (380). Once the surgical debris, body fluid, etc. has been driven from the interior cavity of shaft assembly (330), cleaning element (300) may be moved back to the proximal position as shown in FIG. 12A by rotating clamp arm (354) toward ultrasonic blade (342). Thus, the interior cavity of shaft assembly (330) is cleaned of surgical debris, body fluid, etc. each time end effector (340) is opened.

It should be understood that in some versions of instrument (310), second yoke portion (302C) may comprise an elastomeric wiper that extends inwardly from an interior surface of second yoke portion (302C) and contacts the exterior surface of waveguide (380). It should further be understood that in some versions of instrument (310), second yoke portion (302C) may comprise an elastomeric wiper that extends outwardly from an exterior surface of second yoke portion (302C) and contacts the interior surface of cap (333).

Instrument (310) may be configured such that second yoke portion (302C) of body (302) of cleaning element (300) contacts waveguide (380) at a node associated with resonant ultrasonic vibrations communicated through waveguide (380) and ultrasonic blade (342) when cleaning element (300) is in the proximal position. Alternatively, instrument (310) may be configured such that second yoke portion (302C) of body (302) of cleaning element (300) contacts waveguide (380) away from a node associated with resonant ultrasonic vibrations communicated through waveguide (380) and ultrasonic blade (342) when cleaning element (300) is in the proximal position. Although second yoke portion (302C) of cleaning element (300) of the present example contacts the exterior surface of waveguide (380), it should be understood that second yoke portion (302C) of cleaning element (300) may alternatively contact the exterior surface of ultrasonic blade (342).

C. Third Exemplary Cleaning Element

Figure 17C:
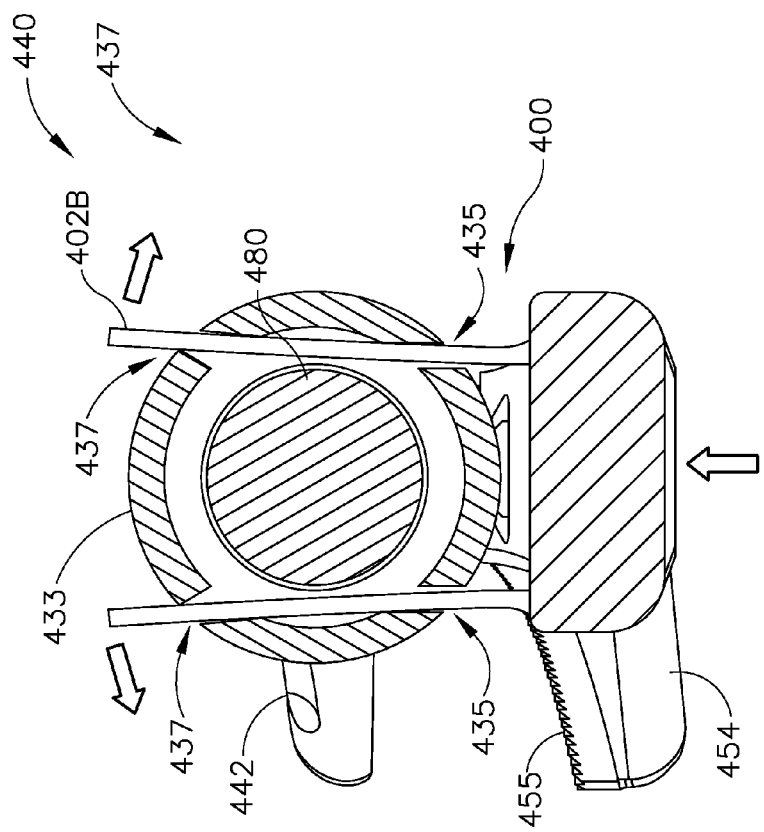
FIG. 17C depicts a cross-sectional view of the instrument of FIG. 16 with the clamp arm of FIG. 17A moved to a third position.

FIGS. 16-17C show another exemplary alternative instrument (410) with a cleaning element (400) configured to clean and/or drive surgical debris, body fluid, etc. from the interior cavity of a shaft assembly (430). Instrument (410) of the present example is configured to operate substantially similar to instruments (10, 210, 310) discussed above except for the differences discussed below. As shown in FIG. 16, instrument (410) of the present example comprises a shaft assembly (430) and an end effector (440). Instrument (410) also includes a clamp arm assembly (450) that is pivotable toward and away from shaft assembly (430). A cap (433) is secured to a distal end of shaft assembly (430). End effector (440) includes an ultrasonic blade (442) extending distally from cap (433) of shaft assembly (430); and a pivoting clamp arm (454), which is an integral feature of clamp arm assembly (450). Clamp arm assembly (450) is pivotably coupled to a projection (434) extending laterally from shaft assembly (430) such that clamp arm (454) is pivotable toward and away from ultrasonic blade (442) to thereby clamp tissue between a clamp pad (455) of clamp arm (454) and ultrasonic blade (442). Ultrasonic vibrations that are generated by a transducer assembly (not shown) are communicated along an acoustic waveguide (480), which extends through shaft assembly (430) to reach ultrasonic blade (442). Ultrasonic blade (442) vibrates at ultrasonic frequencies to cut and/or seal tissue.

As shown in FIGS. 16-17C, cleaning element (400) comprises a pair of flexible members (402A, 402B) projecting from a top surface of clamp arm (454). Flexible members (402A, 402B) are angled inwardly. Cap (433) of the present example includes a pair of slots (435) formed in a bottom surface of cap (433) and a pair of slots (437) formed in a top surface of cap (433). As will be discussed in more detail below, as clamp arm (454) is moved toward and away from ultrasonic blade (442), flexible members (402A, 402B) pass through slots (435, 437) formed in cap (433). As flexible members (402A, 402B) pass through slots (435) formed in cap (433), flexible members (402A, 402B) engage an exterior surface of waveguide (480). Slots (437) are angled outwardly such that as flexible members (402, 402B) pass through slots (437), flexible members (402A, 402B) will be driven outwardly and away from the exterior surface of waveguide (480). The movement of flexible members (402A, 402B) across the exterior surface of waveguide (480) cleans surgical debris, body fluid, etc. from the exterior surface of waveguide (480) and the interior of shaft assembly (430).

As shown in FIG. 16, with clamp arm (454) in an open position, flexible members (402A, 402B) are completely removed from the interior cavity of shaft assembly (430). FIG. 17A shows clamp arm (454) in a partially open position. In this partially open position, flexible members (402A, 402B) are partially disposed within the interior cavity of shaft assembly (430) via slots (435) formed in the bottom surface of cap (433). In this partially open position, flexible members (402A, 402B) have not yet engaged the exterior surface of waveguide (480). As shown in FIG. 17B, as clamp arm (454) is rotated toward ultrasonic blade (442) into a partially closed position, flexible members (402A, 402B) engage and move across the exterior surface of waveguide (480) thereby cleaning the exterior surface of waveguide (480). As shown in FIG. 17C, as clamp arm (454) is further rotated toward ultrasonic blade (442) into a completely closed position, flexible members (402A, 402B) pass through slots (437) formed in the top surface of cap (433). As flexible members (402A, 402B) pass through slots (437), the outwardly angled orientation of slots (437) drive flexible members (402A, 402B) outwardly away from waveguide (480) such that in the completely closed position, flexible members (402A, 402B) are no longer engaged with the exterior surface of waveguide (480). Thus, it should be understood that in the completely closed position, flexible members (402A, 402B) do not interrupt or receive the ultrasonic vibrations communicated through waveguide (480) and ultrasonic blade (442). As clamp arm (454) is rotated away from ultrasonic blade (442) back to the partially closed position, flexible members (402A, 402B) move back across the exterior surface of waveguide (480). Thus, it should be understood that flexible members (402A, 402B) will move across the exterior surface of waveguide (480) as clamp arm (454) is moved toward and away from ultrasonic blade (442). This movement of flexible members (402A, 402B) across the exterior surface of waveguide (480) cleans the exterior surface of waveguide (480) and the interior of shaft assembly (430) of surgical debris, body fluid, etc.

Flexible members (402A, 402B) may be configured and/or positioned such that flexible members (402A, 402B) contact waveguide (480) at a node associated with resonant ultrasonic vibrations communicated through waveguide (480) and ultrasonic blade (442). Alternatively, flexible members (402A, 402B) may be configured and/or positioned such that flexible members (402A, 402B) contact waveguide (480) away from a node associated with resonant ultrasonic vibrations communicated through waveguide (480) and ultrasonic blade (442). Although instrument (410) of the present example is configured such that flexible members (402A, 402B) contact the exterior surface of waveguide (480), it should be understood that instrument (410) may alternatively be configured such that flexible members (402A, 402B) contact the exterior surface of ultrasonic blade (442).

D. Fourth Exemplary Cleaning Element

Figure 18:
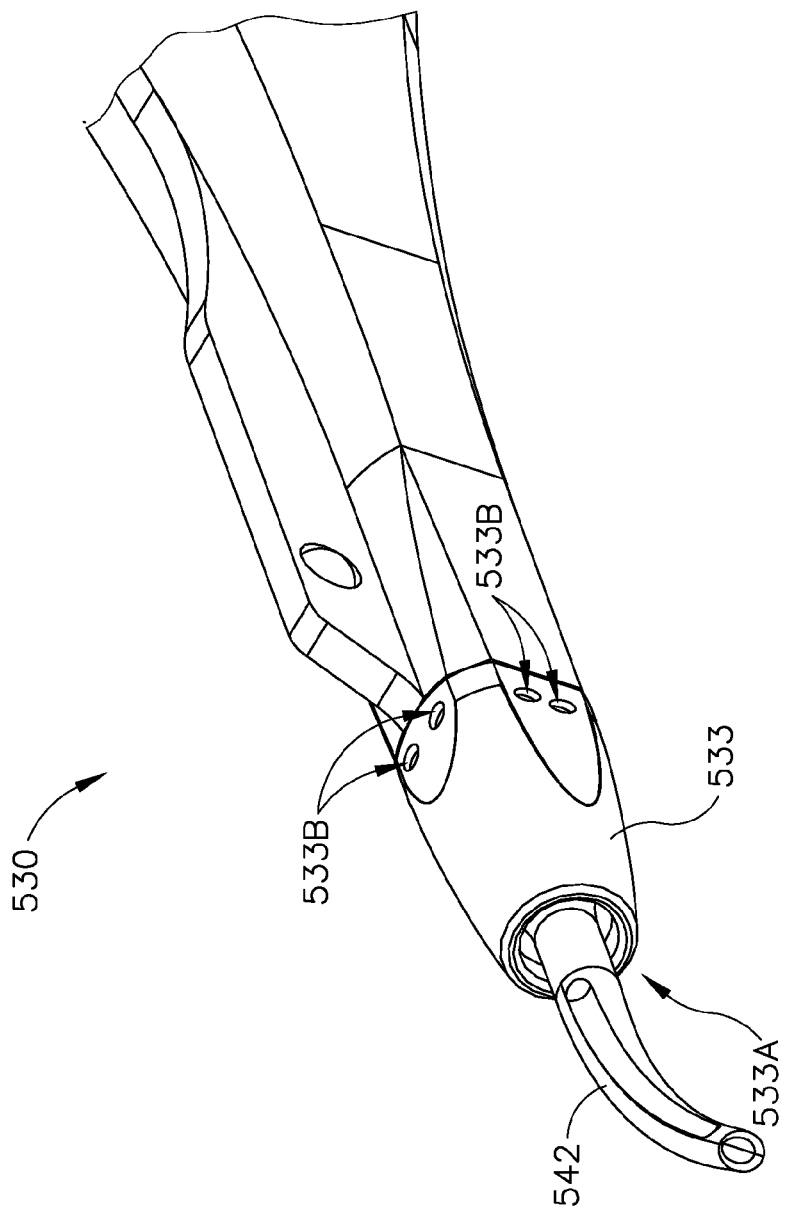
FIG. 18 depicts a perspective view of an exemplary shaft assembly operable to be used with the instrument of FIG. 1.
Figure 19:
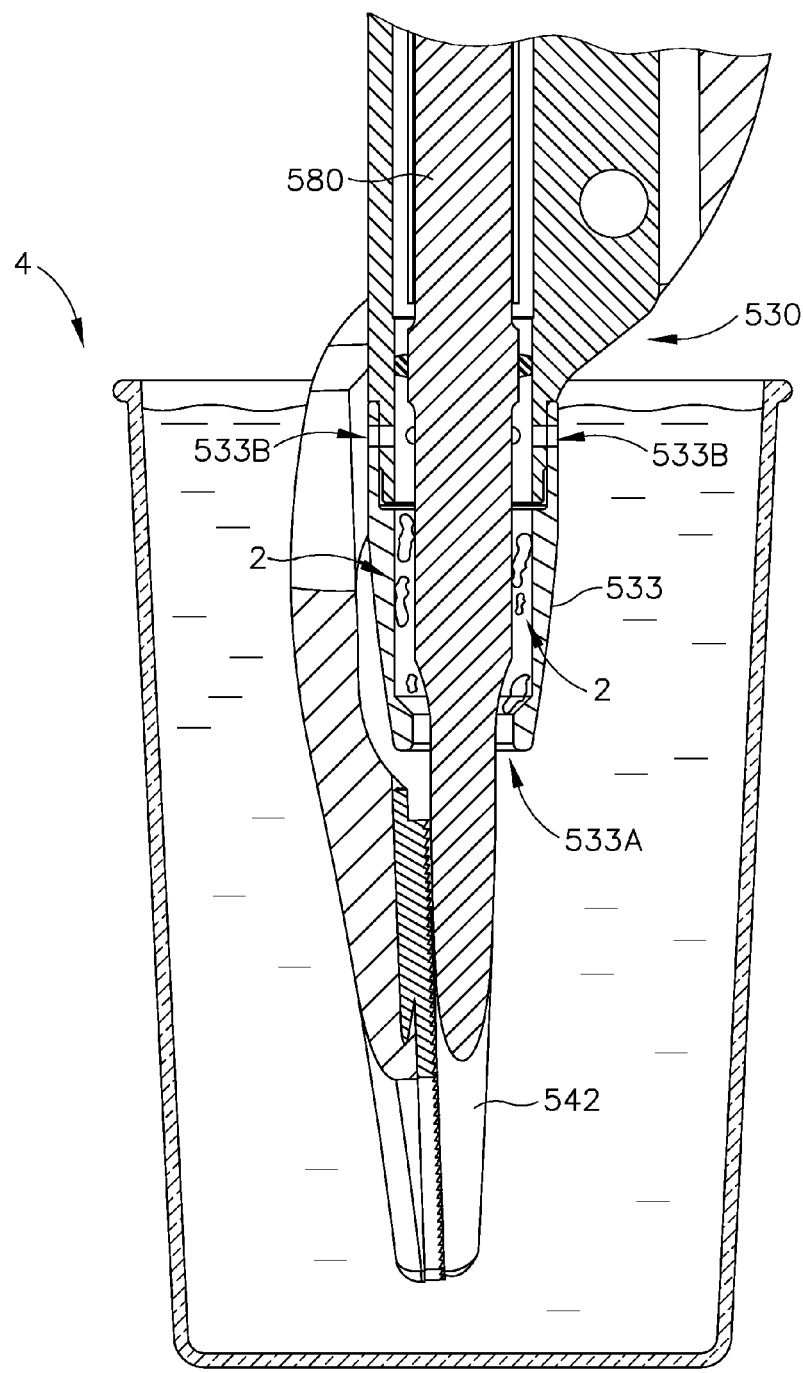
FIG. 19 depicts a cross-sectional view of a variation of the instrument of FIG. 1 having the shaft assembly of FIG. 18 disposed within a container of fluid.

FIGS. 18 and 19 show an exemplary alternative shaft assembly (530) with an exemplary cap (533) configured to allow surgical debris, body fluid, etc. to be driven from the interior cavity of a shaft assembly (530). Cap (533) is secured to a distal end of shaft assembly (530). An ultrasonic blade (542) extends distally from cap (533) of shaft assembly (530). Ultrasonic vibrations that are generated by a transducer assembly (not shown) are communicated along an acoustic waveguide (580), which extends through shaft assembly (530) to reach ultrasonic blade (542). Ultrasonic blade (542) vibrates at ultrasonic frequencies to cut and/or seal tissue. It should be understood that shaft assembly (530) of the present example may be used with any instrument (10, 210, 310, 410) discussed above. Furthermore, cap (533) may comprise any of the features of caps (33, 233, 333, 433) discussed above.

Cap (533) of the present example includes a plurality of openings (533B). Openings (533B) pass completely through cap (533). Openings (533B) are formed in a proximal portion of cap (533). Openings (533B) allow for fluid to pass out of interior cavity of shaft assembly (530) to thereby drive any surgical debris and/or body fluid (2) from the interior cavity of shaft assembly (530). For instance, as shown in FIG. 19, a distal portion of shaft assembly (530) may be dipped into a cup of saline (4) or any other appropriate cleaning liquid. As the distal portion of shaft assembly (530) is dipped into the saline, openings (533B) allow air to escape from the interior cavity of shaft assembly (530) as the saline enters the interior cavity of shaft assembly (530) through an opening (533A) formed in the distal end of cap (533). This saline within the interior cavity of shaft assembly (530) may loosen surgical debris and/or body fluid (2) within the interior cavity of shaft assembly (530). Vibration of ultrasonic blade (542) (e.g., while the distal portion of shaft assembly (530) is still dipped in saline) may improve the ability of the saline to loosen surgical debris and/or body fluid (2). As the distal portion of shaft assembly (530) is removed from the saline, it should be understood that saline will pass out of the interior cavity of shaft assembly (530) via opening (533A) to thereby remove loosened surgical debris and/or body fluid (2) from the interior cavity of shaft assembly (530). As the saline passes out of the interior cavity of shaft assembly (530), it should be understood that openings (533B) will allow air to enter into the interior cavity of shaft assembly (530) such that openings (533B) promote drainage through opening (533A). In addition to or as an alternative to loosened surgical debris and/or body fluid (2) exiting the interior cavity of shaft assembly (530) via opening (533A), activation of ultrasonic blade (542) in the saline may draw the saline into the interior cavity of shaft assembly (530) via opening (533A), such that the loosened surgical debris and/or body fluid (2) exits the interior cavity of shaft assembly (530) via openings (533B).

E. Fifth Exemplary Cleaning Element

Figure 20:
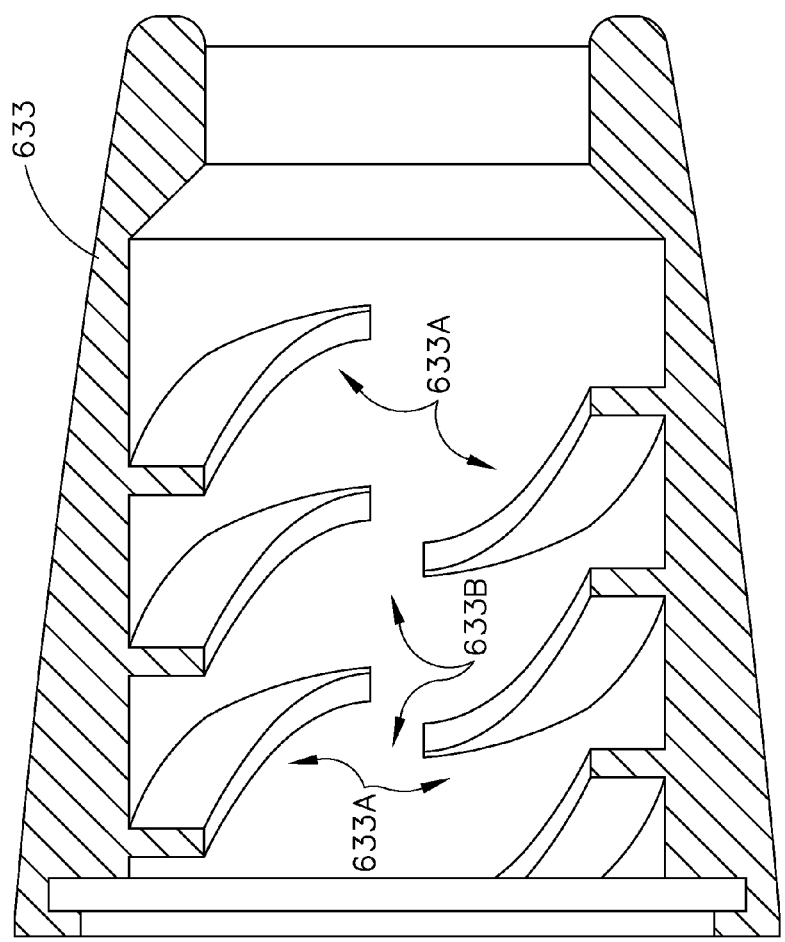
FIG. 20 depicts a cross-sectional view of another exemplary alternative cleaning element.
Figure 21:
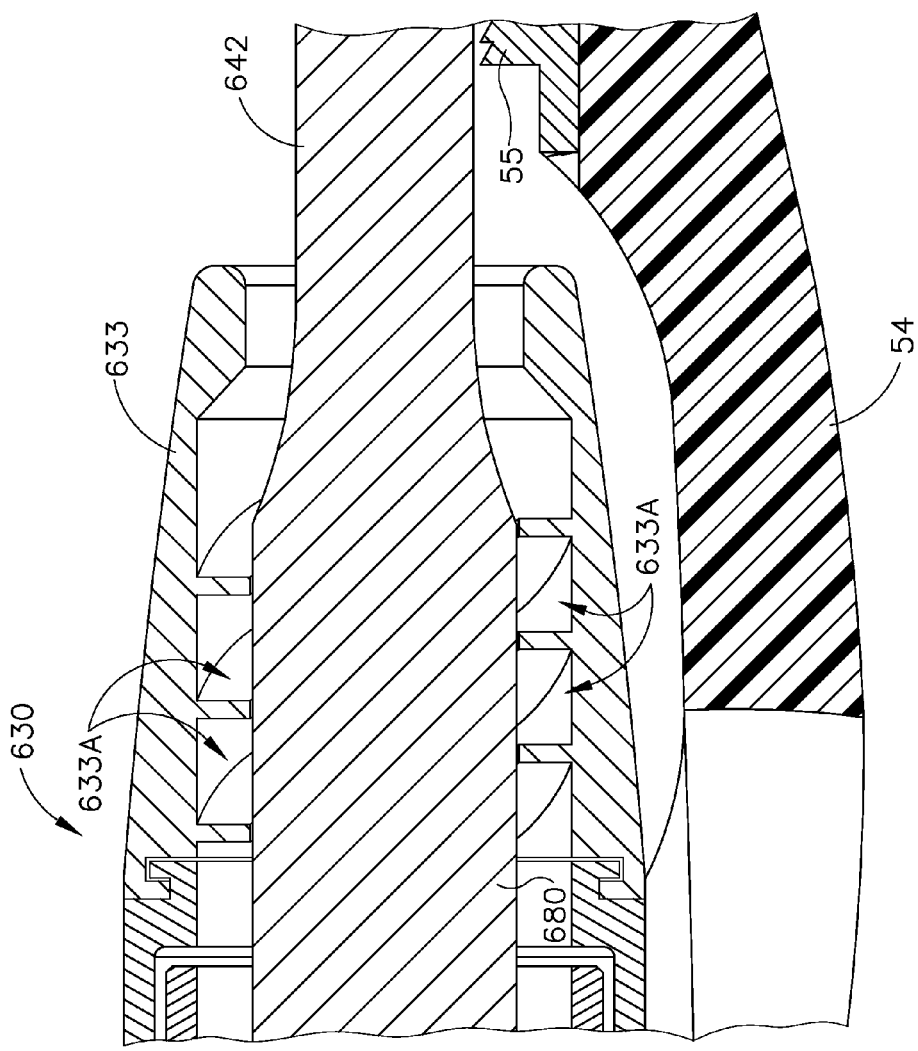
FIG. 21 depicts a cross-sectional view of the cleaning element of FIG. 20.

FIGS. 20 and 21 show an exemplary alternative cap (633) configured to clean and/or drive surgical debris, body fluid, etc. from the interior cavity of a shaft assembly (630). Cap (633) is rotatably coupled to a distal end of shaft assembly (630) such that cap (633) is rotatable about a longitudinal axis defined by shaft assembly (630). An ultrasonic blade (642) extends distally from cap (633) of shaft assembly (630). Ultrasonic vibrations that are generated by a transducer assembly (not shown) are communicated along an acoustic waveguide (680), which extends through shaft assembly (630) to reach ultrasonic blade (642). Ultrasonic blade (642) vibrates at ultrasonic frequencies to cut and/or seal tissue. It should be understood that shaft assembly (630) of the present example may be used with any instrument (10, 210, 310, 410, 510) discussed above. Furthermore, cap (633) may comprise any of the features of caps (33, 233, 333, 433, 533) discussed above.

Cap (633) comprises a plurality of helical projections (633A) extending inwardly from an interior surface of cap (633). As shown in FIG. 21, helical projections (633A) extend from the interior surface of cap (633) and contact an exterior surface of waveguide (680). In some versions of cap (633), helical projections (633A) may comprise an elastomeric wiper that extends inwardly from an interior surface of each helical projection (633A) and contacts the exterior surface of waveguide (680). A plurality of openings (633B) exist between helical projections (633A) such that surgical debris, body fluid, etc. may pass through. Because cap (633) is rotatably coupled with the distal end of shaft assembly (630), cap (633) may be manually rotated by a user. Rotation of cap (633) causes rotation of helical projections (633A) to thereby drive surgical debris, body fluid, etc. from the interior cavity of shaft assembly (630) and clean the exterior surface of ultrasonic blade (642). It should be understood that cap (633) may include features that permit cap (633) to only rotate in a single direction (e.g. such that helical projections (633A) can only drive surgical debris, body fluid, etc. distally). It should also be understood that cap (633) may include any suitable number of helical projections (633A). By way of example only, some versions of cap (633) may have just one helical projection (633A). Other versions of cap (633) may have two or more helical projections (633A).

As will be appreciated from the discussion below, cap (633) may be configured such that movement of a clamp arm toward and/or away from ultrasonic blade (642) causes rotation of cap (633) thereby driving surgical debris, body fluid, etc. from the interior cavity of shaft assembly (630) and cleaning the exterior surface of ultrasonic blade (642) each time the clamp arm is moved.

Helical projections (633A) may be configured and/or positioned such that helical projections (633A) contact waveguide (680) at nodes associated with resonant ultrasonic vibrations communicated through waveguide (680) and ultrasonic blade (642). Alternatively, helical projections (633A) may be configured and/or positioned such that helical projections (633A) contact waveguide (680) away from nodes associated with resonant ultrasonic vibrations communicated through waveguide (680) and ultrasonic blade (642).

F. Sixth Exemplary Cleaning Element

Figure 22:
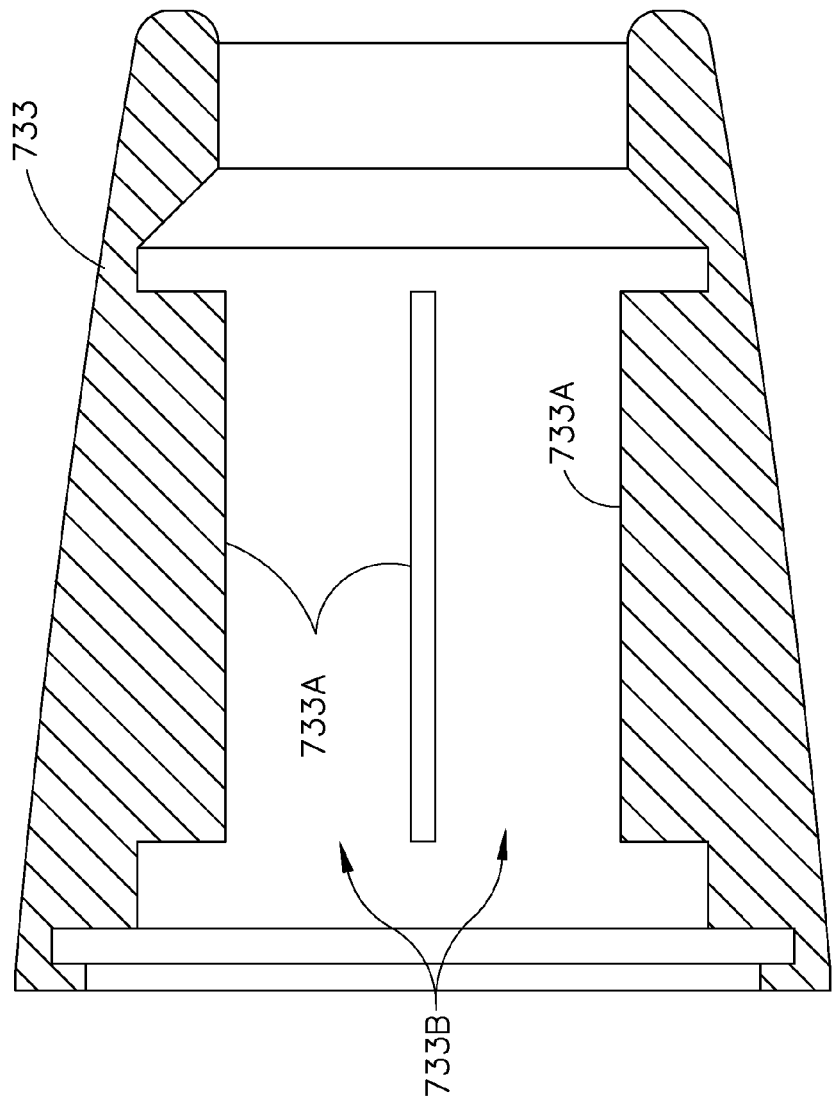
FIG. 22 depicts a cross-sectional view of yet another exemplary alternative cleaning element.
Figure 23A:
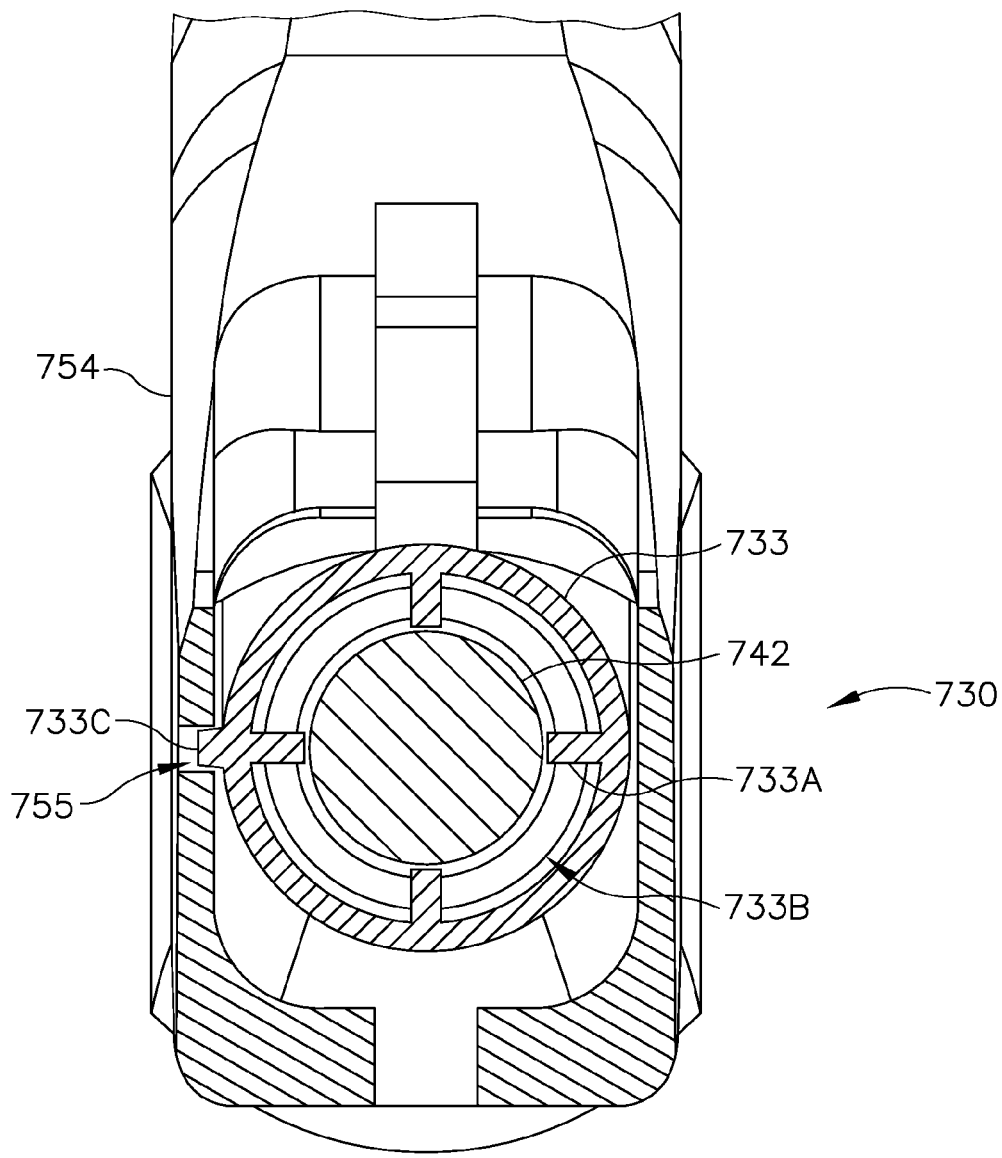
FIG. 23A depicts a cross-sectional view of the cleaning element of FIG. 22 in a first rotational position.
Figure 23B:
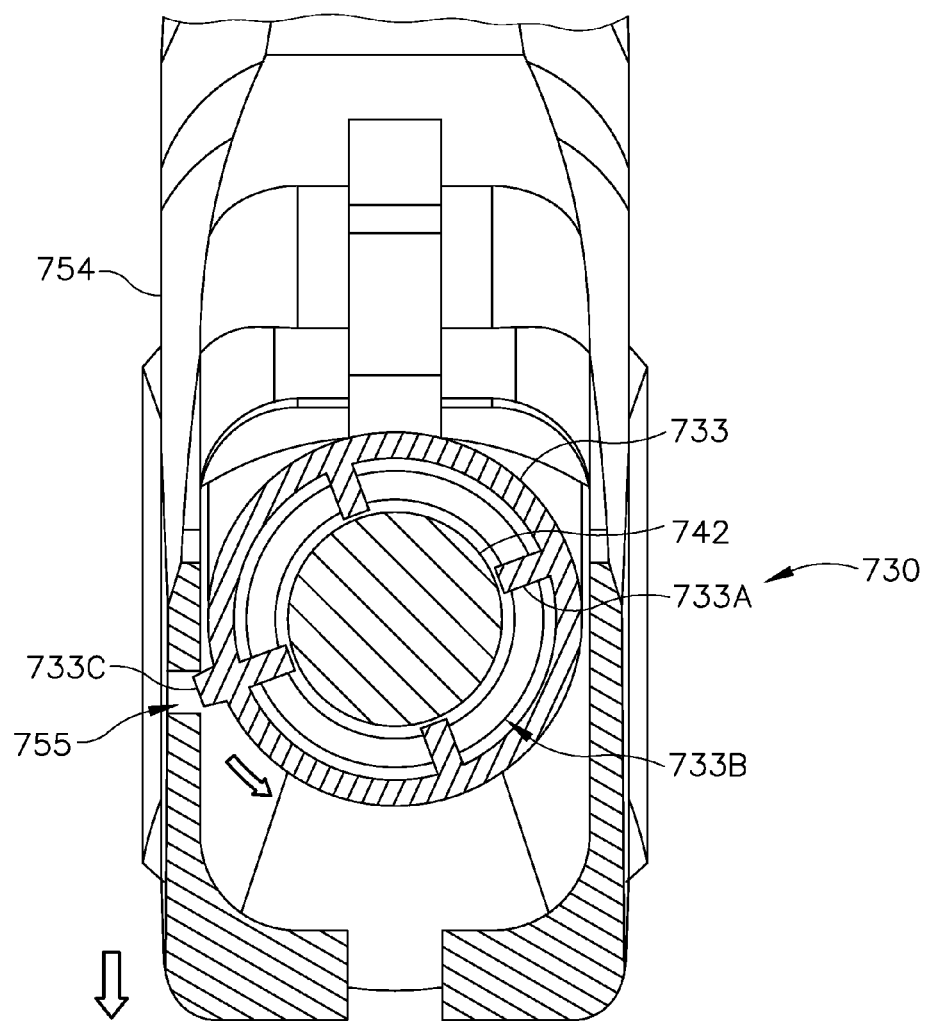
FIG. 23B depicts a cross-sectional view of the cleaning element of FIG. 22 moved to a second rotational position.

FIGS. 22-23B show an exemplary alternative cap (733) configured to clean and/or drive surgical debris, body fluid, etc. from the interior cavity of a shaft assembly (730). Cap (733) is rotatably coupled to a distal end of shaft assembly (730) such that cap (733) is rotatable about a longitudinal axis defined by shaft assembly (730). An ultrasonic blade (742) extends distally from cap (733) of shaft assembly (730). Ultrasonic vibrations that are generated by a transducer assembly (not shown) are communicated along an acoustic waveguide (780), which extends through shaft assembly (730) to reach ultrasonic blade (742). Ultrasonic blade (742) vibrates at ultrasonic frequencies to cut and/or seal tissue. It should be understood that shaft assembly (730) of the present example may be used with any instrument (10, 210, 310, 410, 510) discussed above. Furthermore, cap (733) may comprise any of the features of caps (33, 233, 333, 433, 533,633) discussed above.

Cap (733) comprises a plurality of longitudinal projections (733A) extending inwardly from an interior surface of cap (733). As shown in FIGS. 23A-23B, longitudinal projections (733A) extend from the interior surface of cap (733) and contact an exterior surface of waveguide (780). In some versions of cap (733), longitudinal projections (733A) may comprise an elastomeric wiper that extends inwardly from an interior surface of each longitudinal projection (733A) and contacts the exterior surface of waveguide (780). A plurality of longitudinal openings (733B) exist between longitudinal projections (733A) such that surgical debris, body fluid, etc. may pass through. Because cap (733) is rotatably coupled with the distal end of shaft assembly (730), cap (733) may be rotated. Rotation of cap (733) causes rotation of longitudinal projections (733A) to thereby clean the exterior surface of waveguide (780). While longitudinal projections (733A) are oriented longitudinally in the present example, it should be understood that longitudinal projections (733A) may alternatively be oriented obliquely, helically, or otherwise oriented. It should also be understood that cap (733) may include any suitable number of longitudinal projections (733A). By way of example only, some versions of cap (733) may have just one longitudinal projection (733A). Other versions of cap (733) may have two or more longitudinal projections (733A).

As shown in FIGS. 23A and 23B, cap (733) comprises a tab (733C) projecting outwardly from an exterior surface of cap (733). A clamp arm (754) of the present example comprises an opening (755). Cap (733) is oriented such that tab (733C) is positioned within opening (755) of clamp arm (754). FIG. 23A shows clamp arm (754) in a closed position. With clamp arm (754) in the closed position, cap (733) and longitudinal projections (733A) are in a first rotational position. FIG. 23B shows clamp arm (754) moved away from ultrasonic blade (742) in a partially open position. Movement of clamp arm (754) away from ultrasonic blade (742) causes movement of opening (755). This movement of opening (755) drives concurrent movement of tab (733C) of cap (733) and thereby rotates cap (733) and longitudinal projections (733A) in a first direction. It should be understood that movement of clamp arm (754) toward ultrasonic blade (742) would cause rotation of cap (733) and longitudinal projections (733A) in a second direction. Rotation of longitudinal projections (733A) cleans the exterior surface of waveguide (780) of surgical debris, body fluid, etc. Thus, it should be understood that opening and closing of clamp arm (754) would clean the exterior surface of waveguide (780) by partially rotating cap (733) about waveguide (780) in an oscillatory fashion.

It should be understood that cap (733) may include features that permit cap (733) to only rotate in a single direction. In such a version of cap (733), cap (733) may further include a ratchet and pawl feature that drives cap (733) to rotate incrementally each time clamp arm (754) is moved away from ultrasonic blade (742); and does not drive cap (733) to rotate as clamp arm (754) is moved toward ultrasonic blade (742) or vice versa.

IV. Exemplary Protective Elements

As previously discussed, opening (33A) of cap (33) of instrument (10) provides access to an interior cavity of shaft assembly (30) of instrument (10). It may be desirable to provide protective elements that prevent surgical debris, body fluid, etc. from contacting at least part of the exterior surface of waveguide (80) and/or ultrasonic blade (42) within the interior cavity of shaft assembly (30). Such protective elements need not necessarily seal off the interior cavity. Various merely illustrative examples of such protective elements will be described in greater detail below, while other examples will be apparent to those of ordinary skill in the art in view of the teachings herein.

A. First Exemplary Protective Element

Figure 24:
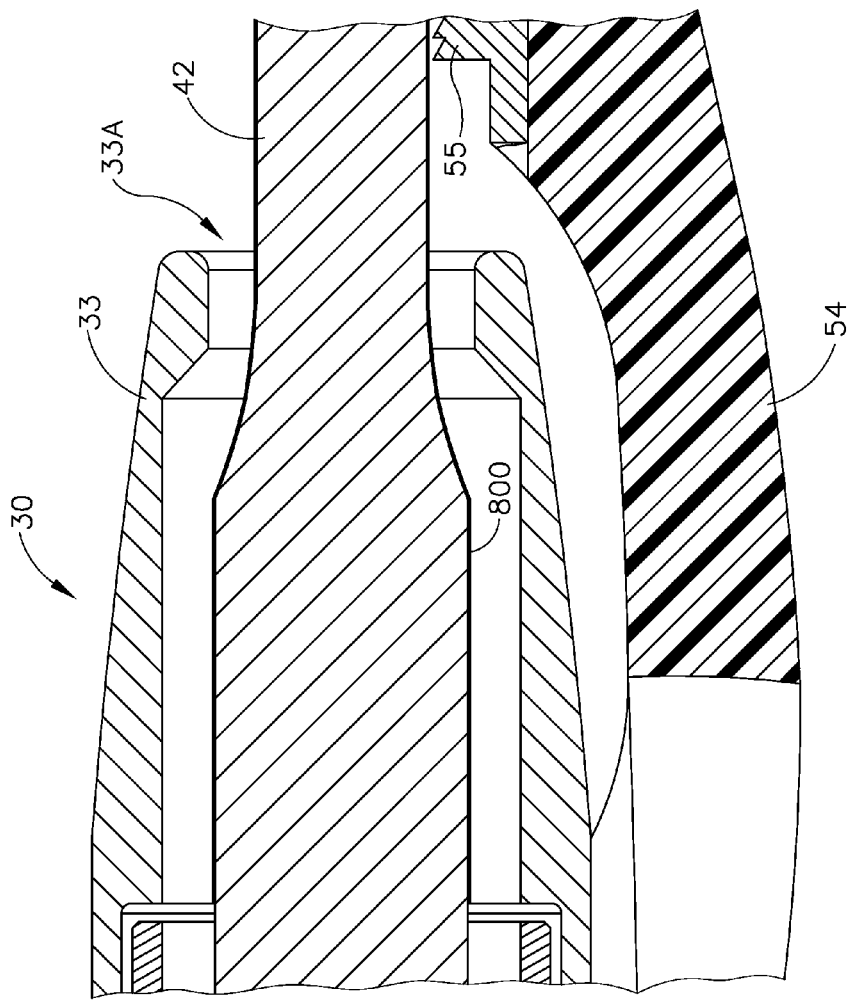
FIG. 24 depicts a cross-sectional view of an exemplary protective element.

FIG. 24 shows one merely illustrative example of a protective element (800). Protective element (800) of this example comprises a protective coating on a distal portion of ultrasonic blade (42). The protective coating may comprise a non-stick coating, including but not limited to polytetrafluoroethylene ("PTFE"), to thereby prevent surgical debris, body fluid, etc. within the interior cavity of shaft assembly (30) from sticking to waveguide (80) and/or ultrasonic blade (42). The protective coating may provide insulation of waveguide (80) and/or ultrasonic blade (42) such that heat is not transferred from waveguide (80) and/or ultrasonic blade (42) to thereby prevent coagulation of surgical debris, body fluid, etc. within the interior cavity of shaft assembly (30). The protective coating may be a lubricous and/or hydrophobic coating (e.g. sodium stearate, etc.) to thereby prevent surgical debris, body fluid, etc. within the interior cavity of shaft assembly (30) from becoming dry.

B. Second Exemplary Protective Element

Figure 25:
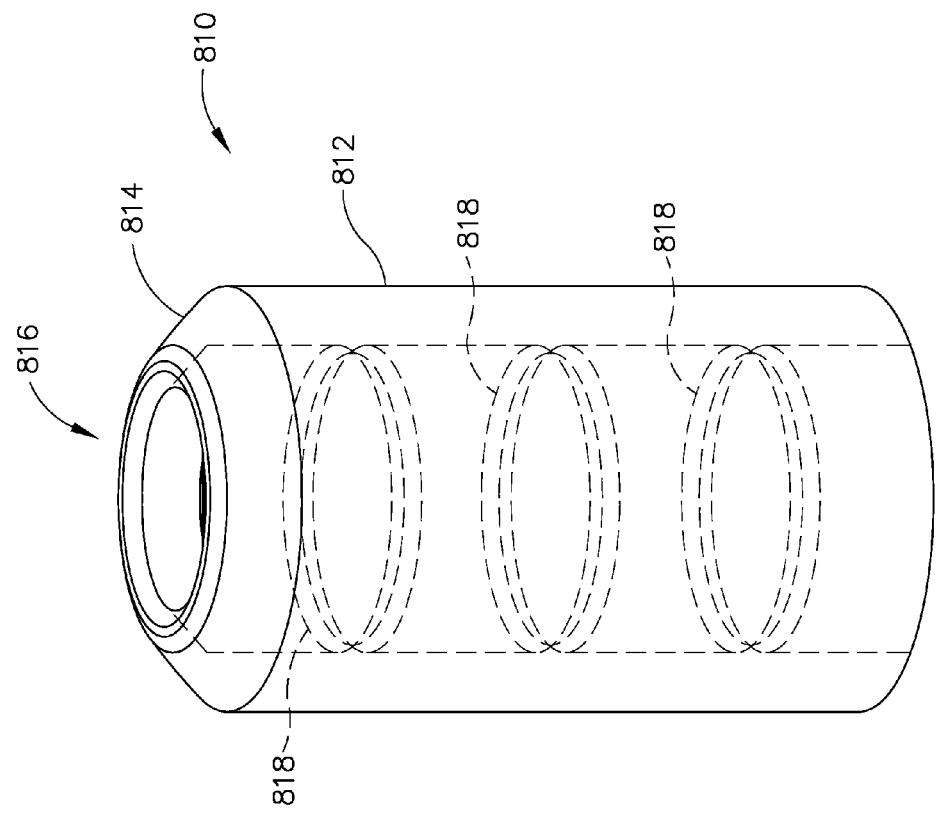
FIG. 25 depicts a perspective view of an exemplary alternative protective element.
Figure 26:
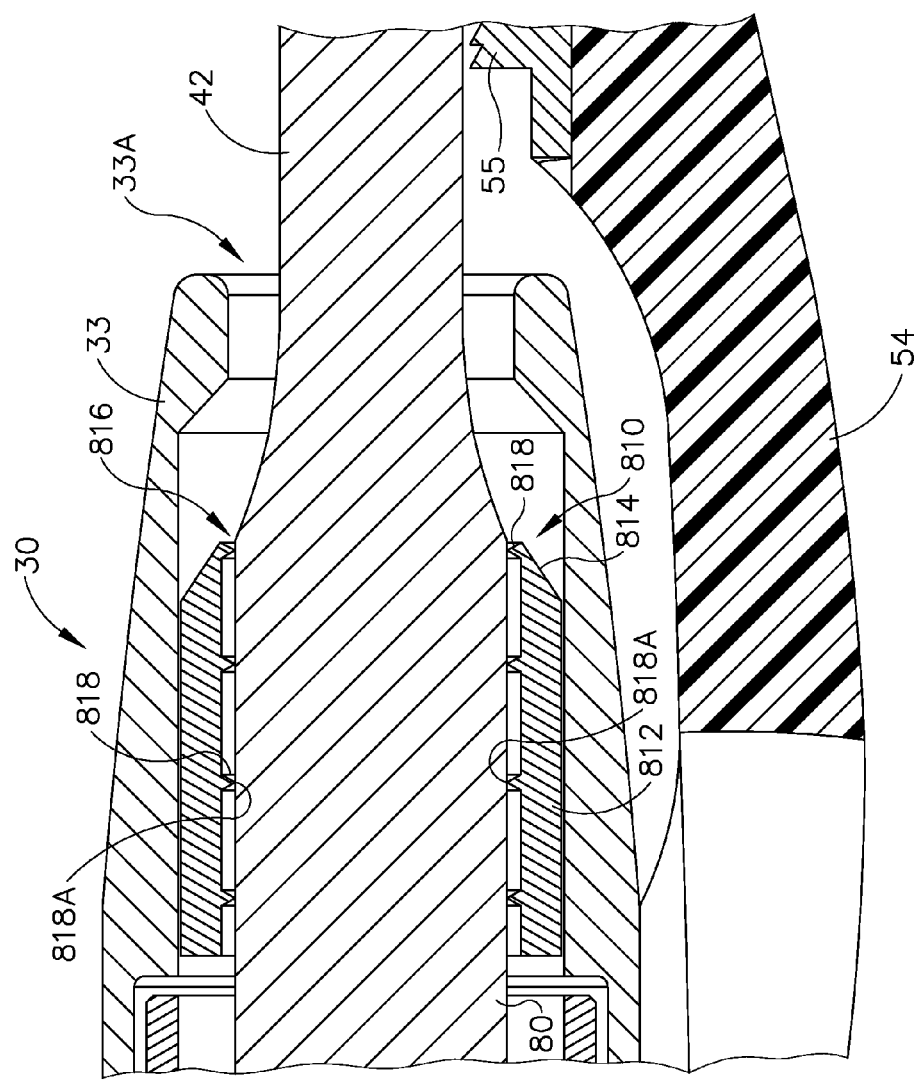
FIG. 26 depicts a cross-sectional view of the protective element of FIG. 25 positioned within the instrument of FIG. 1.

FIGS. 25 and 26 show an exemplary alternative protective element (810) configured to prevent surgical debris, body fluid, etc. from contacting the exterior surface of waveguide (80) within the interior cavity of shaft assembly (30). Protective element (810) comprises a cylindrical body (812) having a tapered end (814). A circular bore (816) passes completely through cylindrical body (812) and tapered end (814) of protective element (810). A plurality of circular projections (818) extend inwardly from an interior surface of circular bore (816). As best seen in FIG. 26, circular projections (818) have a triangular cross-sectional profile. Each circular projection (818) presents an edge (818A). Protective element (810) is disposed within the interior cavity of shaft assembly (30) such that waveguide (80) passes through bore (816) of protective element (810). With waveguide (80) positioned within bore (816), each edge (818A) of each circular projection (818) contacts waveguide (80) thereby preventing cylindrical body (812) and tapered end (814) from contacting waveguide (80). It should be understood that the contact point between edge (818A) of each circular projections (818) and the exterior surface of waveguide (80) extends completely circumferentially about the exterior surface of waveguide (80). This contact may provide a radial seal that prevents contact of solid and/or semi-solid surgical debris from contacting waveguide (80). In addition or in the alternative, protective element (810) may comprise an absorbent material configured to absorb fluid and prevent it from contacting waveguide (80). For instance, circular projections (818) may act as wicks, drawing fluid away from waveguide (80) and toward cylindrical body (812), where it is absorbed and retained. In addition or in the alternative, protective element (810) may comprise a soft material configured to not interrupt or significantly dampen the ultrasonic vibrations communicated through waveguide (80).

C. Third Exemplary Protective Element

Figure 27:
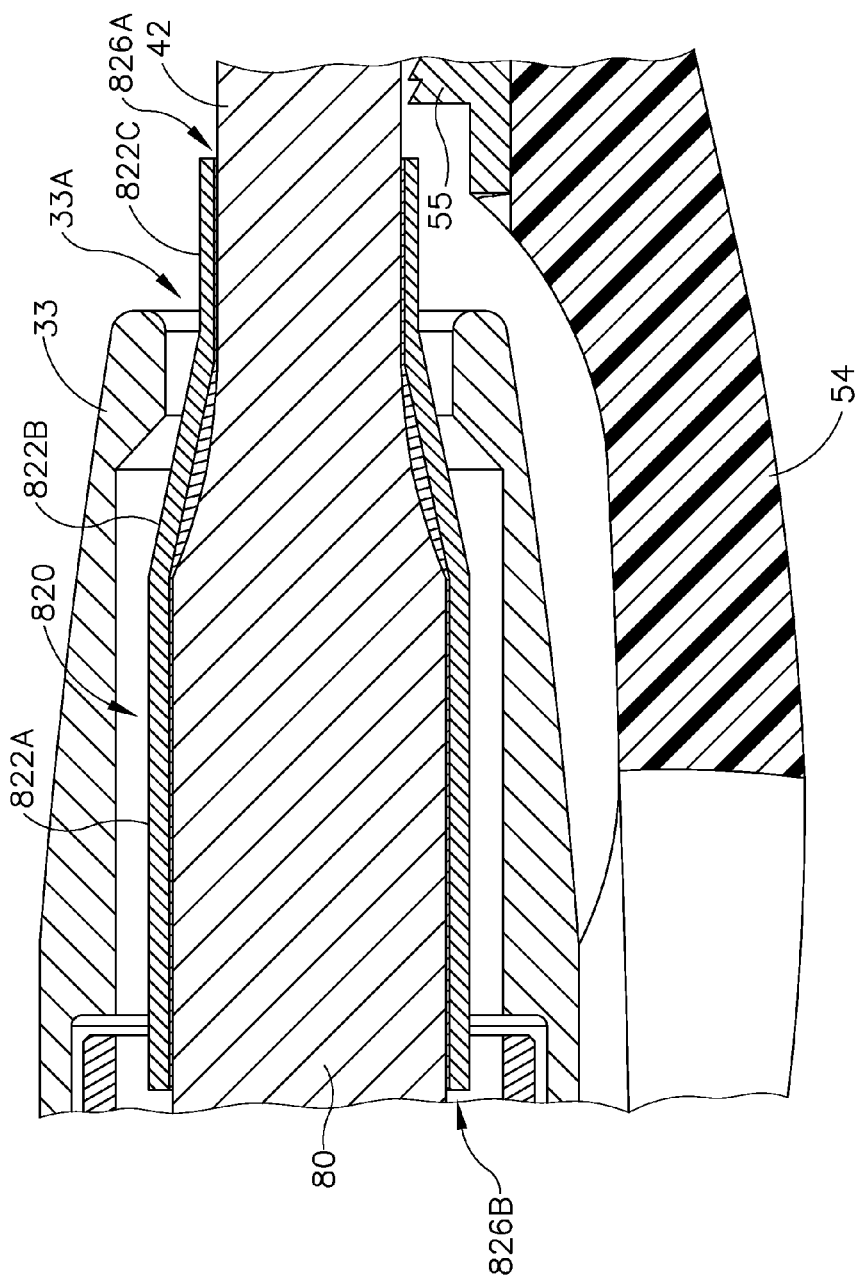
FIG. 27 depicts a perspective view of another exemplary alternative protective element.

FIG. 27 shows another exemplary alternative protective element (820) configured to prevent surgical debris, body fluid, etc. from contacting the exterior surface of waveguide (80) and ultrasonic blade (42) within the interior cavity of shaft assembly (30). Protective element (820) comprises a flexible sleeve having a first cylindrical section (822A), a tapered section (822B), and a second cylindrical section (822C). First cylindrical section (822A), second cylindrical section (822C), and tapered section (822B) are flexible and sized to fit about a distal portion of waveguide (80), a proximal portion of ultrasonic blade (42), and a transitional portion between waveguide (80) and ultrasonic blade (42) respectively. Furthermore, first cylindrical section (822A), tapered section (822B), and second cylindrical section (822C) are sized such that when disposed about ultrasonic blade (42) a small gap exists between the exterior surface of ultrasonic blade (42) and an interior surface of protective element (820). This small gap prevents surgical debris, body fluid, etc. that is larger than the small gap from contacting ultrasonic blade (42). It should be understood that the size and/or flexibly of protective element (820) may be changed to thereby change the size of the small gap existing between protective element (820) and ultrasonic blade (42).

A plurality of flexible scrubbing features (824) extend from the interior surface of protective element (820) and contact the exterior surface of waveguide (80) and ultrasonic blade (42). As waveguide (80) and ultrasonic blade (42) vibrate, scrubbing features (824) scrub surgical debris, body fluid, etc. from the exterior surface of waveguide (80) and ultrasonic blade (42). Openings (826A, 826B) at each end of protective element (820) allow for scrubbed surgical debris, body fluid, etc. to pass through the small gap between protective element (820) and ultrasonic blade (42).

D. Fourth Exemplary Protective Element

Figure 28:
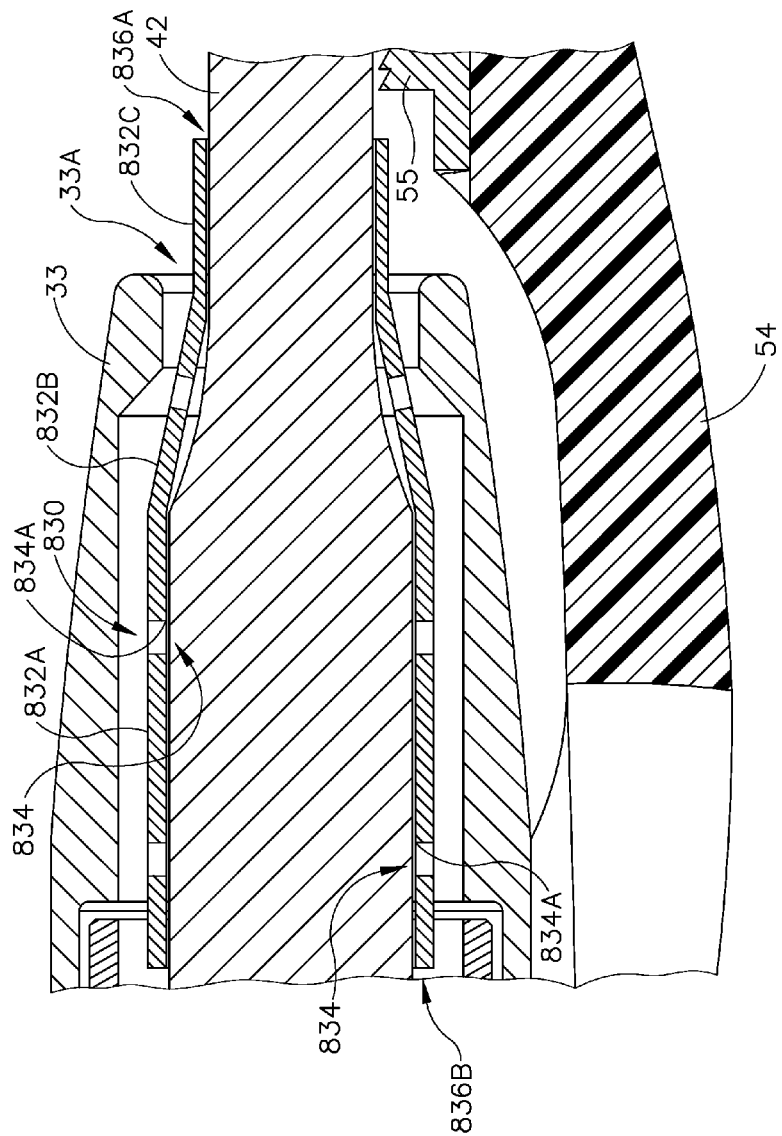
FIG. 28 depicts a perspective view of yet another exemplary alternative protective element.

FIG. 28 shows yet another exemplary alternative protective element (830) configured to prevent surgical debris, body fluid, etc. from contacting the exterior surface of waveguide (80) and ultrasonic blade (42) within the interior cavity of shaft assembly (30). Protective element (830) comprises a flexible sleeve having a first cylindrical section (832A), a tapered section (832B), and a second cylindrical section (832C). First cylindrical section (832A), second cylindrical section (832C), and tapered section (832B) are flexible and sized to fit about a distal portion of waveguide (80), a proximal portion of ultrasonic blade (42), and a transitional portion between waveguide (80) and ultrasonic blade (42) respectively. Furthermore, first cylindrical section (832A), tapered section (832B), and second cylindrical section (832C) are sized such that when disposed about ultrasonic blade (42) a small gap exists between the exterior surface of ultrasonic blade (42) and an interior surface of protective element (830). This small gap prevents surgical debris, body fluid, etc. that is larger than the small gap from contacting ultrasonic blade (42). It should be understood that the size and/or flexibly of protective element (830) may be changed to thereby change the size of the small gap existing between protective element (830) and ultrasonic blade (42).

Protective element (830) comprises a plurality of openings (834). Each opening of plurality of openings (834) present an edge (834A) on an interior surface of protective element (830). As waveguide (80) and ultrasonic blade (42) vibrate, edges (834A) scrape surgical debris, body fluid, etc. from the exterior surface of waveguide (80) and ultrasonic blade (42). Openings (836A, 836B) at each end of protective element (830) allow for scraped surgical debris, body fluid, etc. to pass through the small gap between protective element (830) and ultrasonic blade (42).

V. Exemplary Caps

Figure 29:
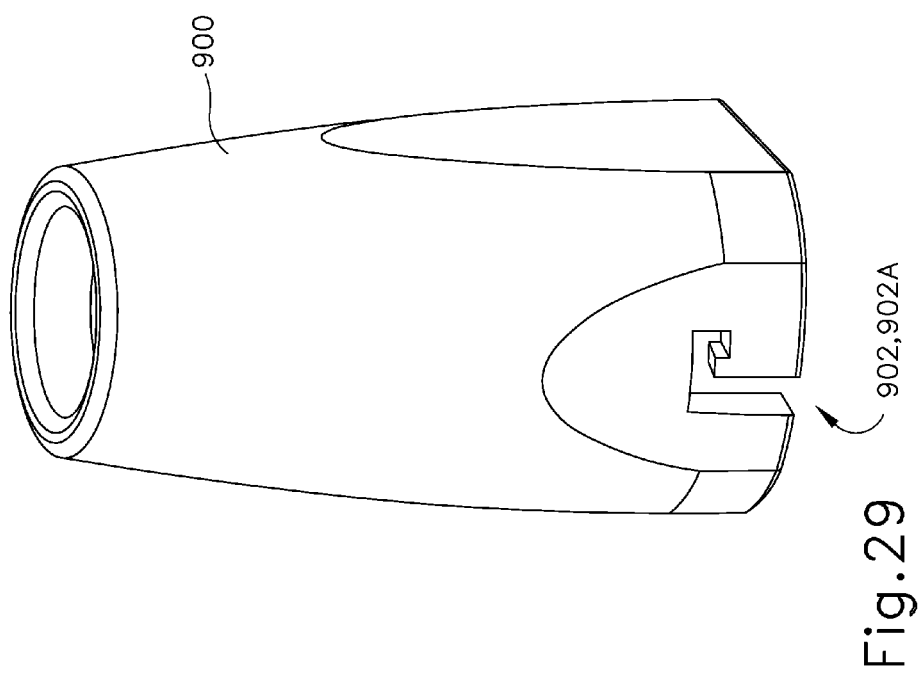
FIG. 29 depicts a perspective view of an exemplary end cap.
Figure 30B:
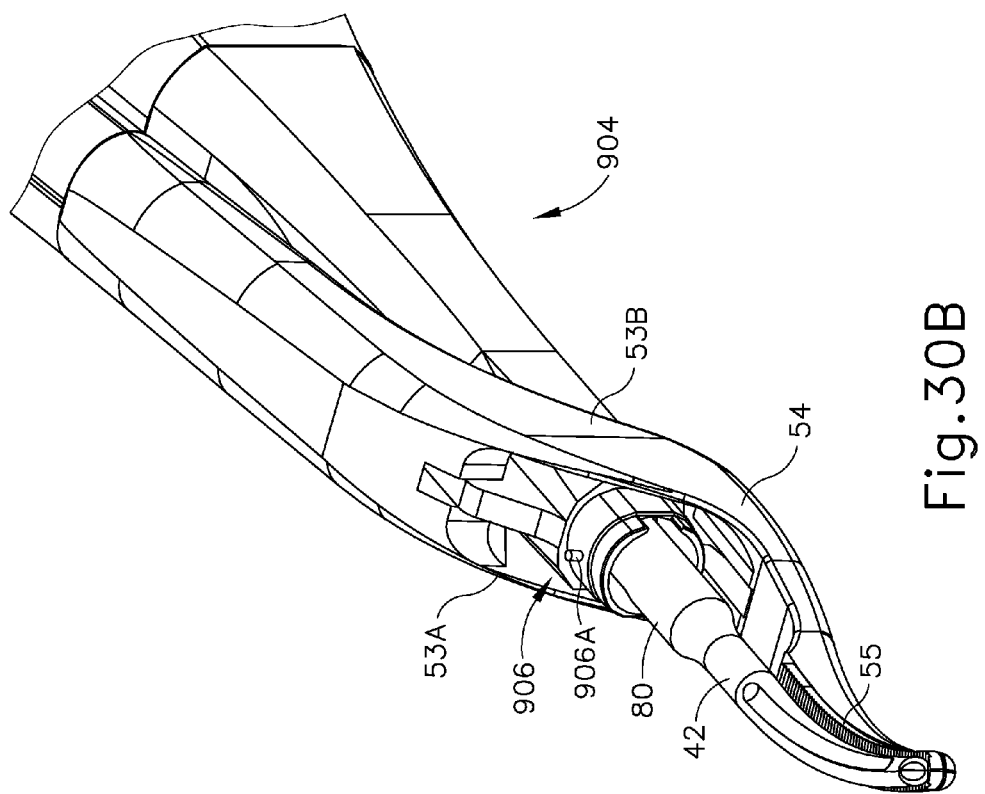
FIG. 30B depicts a perspective view of the instrument of FIG. 30A with the end cap of FIG. 29 removed.

As previously discussed, opening (33A) of cap (33) of instrument (10) provides access to an interior cavity of shaft assembly (30) of instrument (10). It may be desirable to provide cap (33) with features that allow for the interior cavity of shaft assembly (30) to be efficiently cleaned. An example of such a cap (900) is shown in FIGS. 29-30B. Cap (900) of the present example comprises a bayonet feature (902). Bayonet feature (902) comprises an L-shaped slot (902A). A distal end of an exemplary shaft assembly (904) comprises a mating bayonet feature (906). Bayonet feature (906) comprises a pin (906A) projecting from an exterior surface of the distal end of shaft assembly (904). L-shaped slot (902A) of bayonet feature (902) is configured to selectively receive the pin (906A) of bayonet feature (906) to selectively lock cap (900) to the distal end of shaft assembly (904). Bayonet features (902, 906) allow for a user to quickly remove cap (900) from the distal end of shaft assembly (904) such that the interior cavity of shaft assembly (30), waveguide (80), and/or ultrasonic blade (42) may be cleaned. Furthermore, bayonet features (902, 906) allow for a user to quickly reattach cap (900) to the distal end of shaft assembly (30). It should be understood that cap (900) may comprise any of the features of caps (33, 233, 333, 433, 533,633, 733) discussed above.

Figure 31:
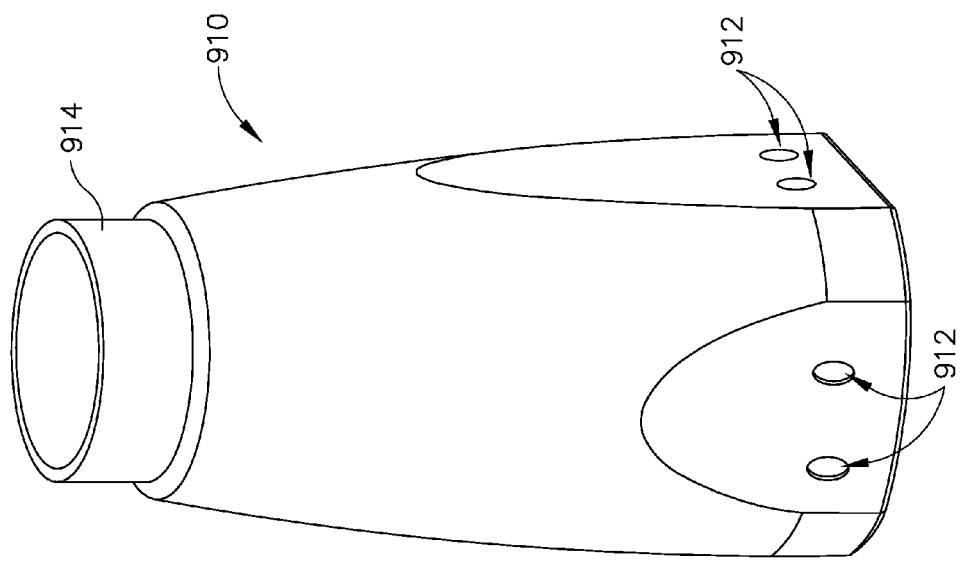
FIG. 31 depicts a perspective view of an exemplary alternative end cap.
Figure 32:
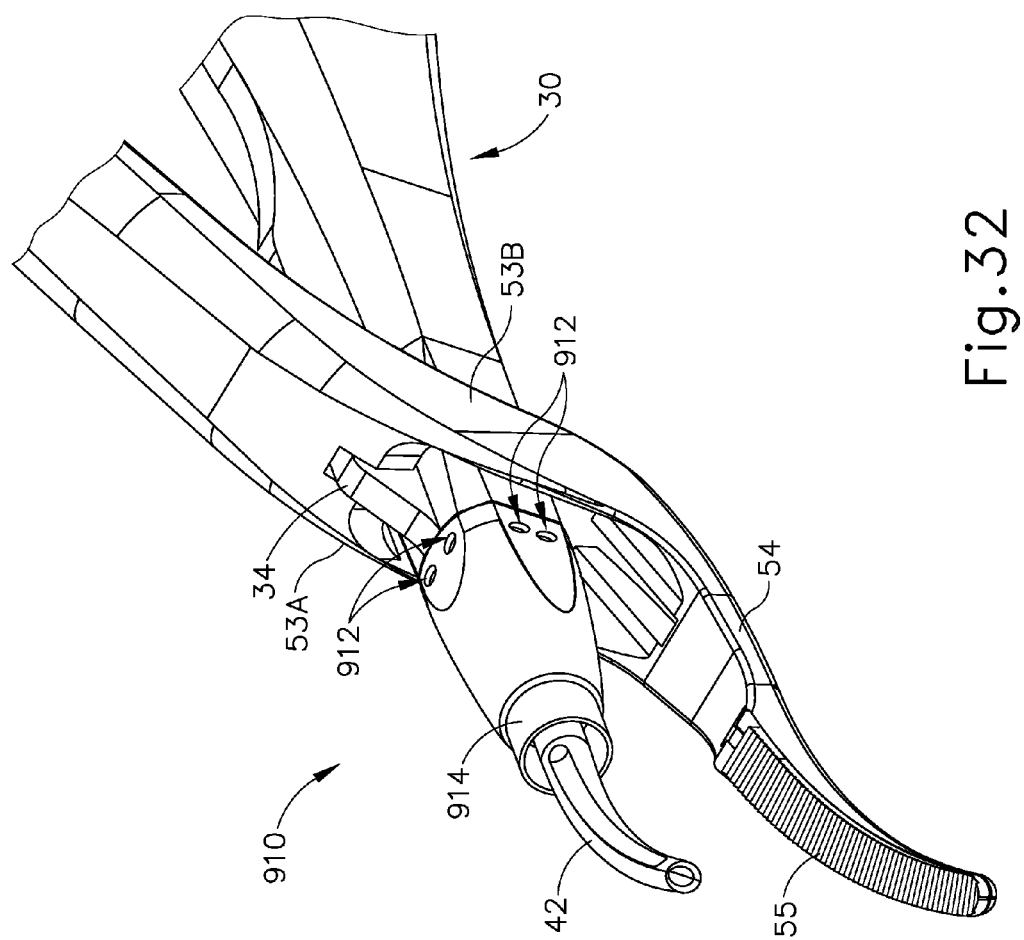
FIG. 32 depicts a perspective view of the end cap of FIG. 31 positioned on the end of yet another exemplary alternative instrument.
Figure 33:
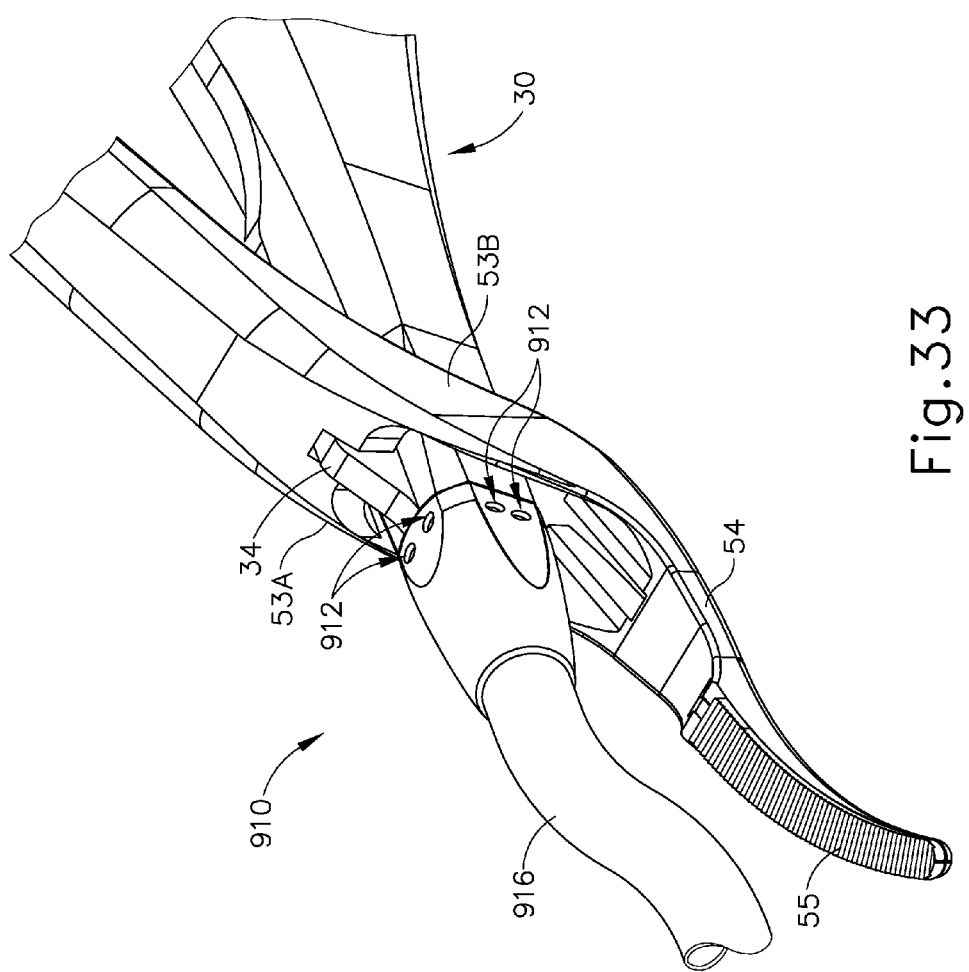
FIG. 33 depicts a perspective view of the end cap of FIG. 31 positioned on the end of yet another exemplary alternative instrument with a vacuum conduit positioned about a distal end of the end cap.

FIGS. 31-33 show an exemplary alternative cap (910) configured to provide for efficient cleaning of the interior cavity of shaft assembly (30). Cap (910) is secured to a distal end of shaft assembly (30). Cap (910) of the present example includes a plurality of openings (912). Openings (912) pass completely through cap (910). Openings (912) are formed in a proximal portion of cap (910). A distal end of cap (910) presents a coupling feature (914). Coupling feature (914) is configured to be selectively secured to a vacuum conduit (916). With vacuum conduit (916) secured to coupling feature (914) of cap (910), as shown in FIG. 33, surgical debris, body fluid, etc. may be removed from the interior cavity of shaft assembly (30). Openings (912) allow for fluid (e.g. air, saline, etc.) to pass through into the interior cavity of shaft assembly (30) to thereby provide for flushing of surgical debris, body fluid, etc. from the interior cavity of shaft assembly (30) when vacuum is applied via vacuum conduit (916). It should be understood that cap (910) may comprise any of the features of caps (33, 233, 333, 433, 533,633, 733, 900) discussed above.

VI. Exemplary Translatable Acoustic Assembly

Figure 34A:
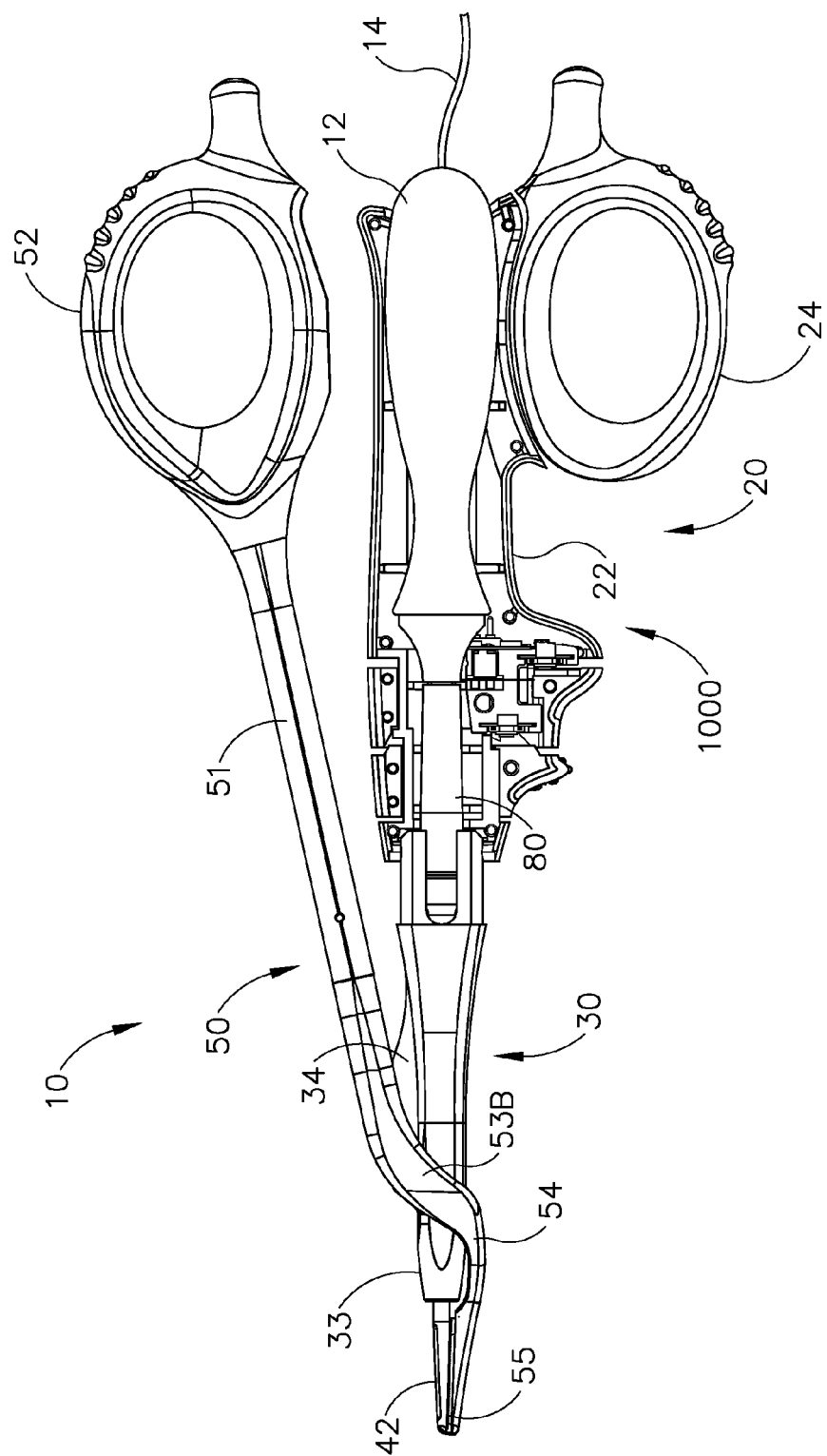
FIG. 34A depicts a side elevational view of yet another exemplary alternative instrument with an acoustic assembly in a first longitudinal position.
Figure 34B:
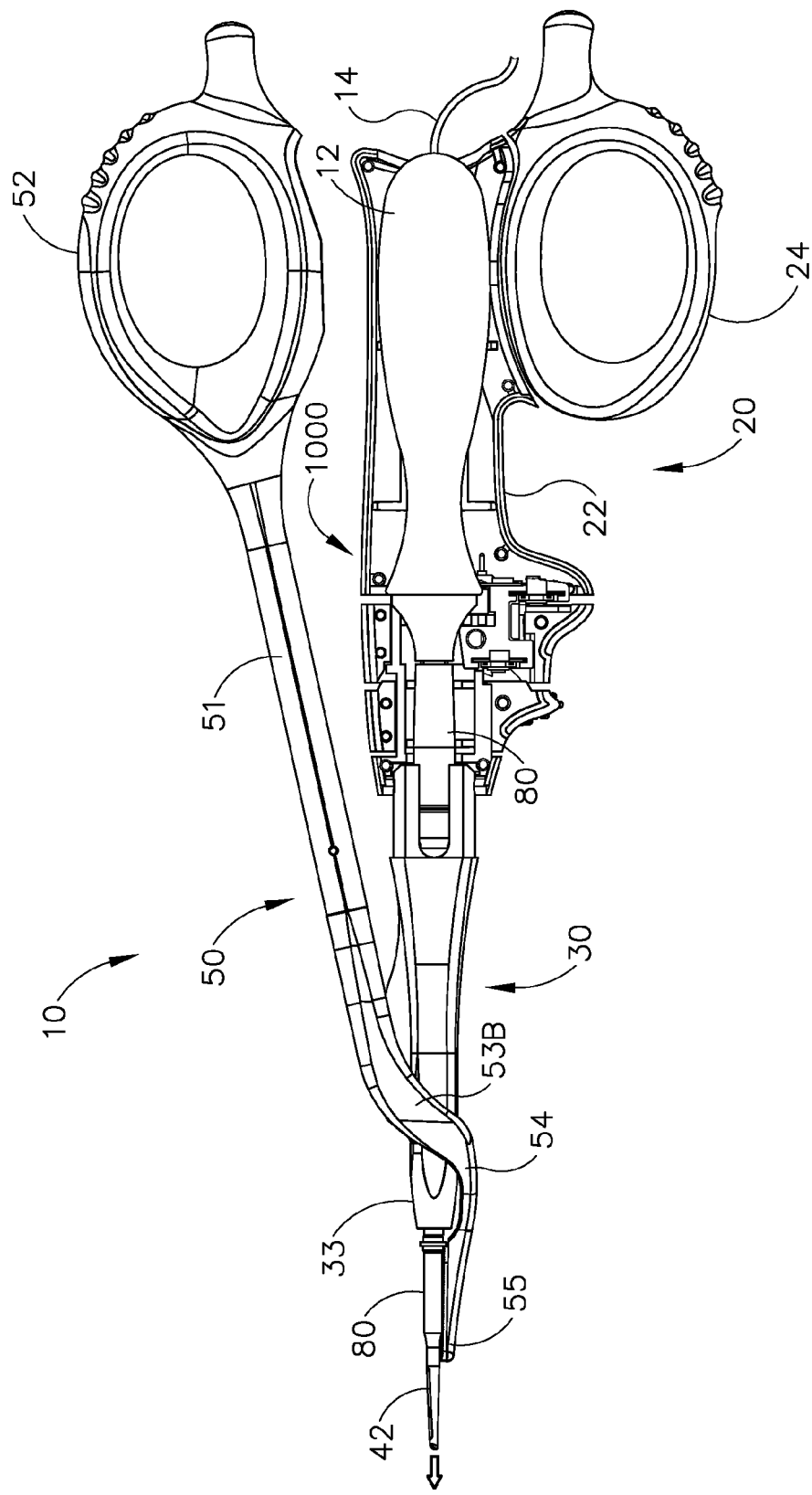
FIG. 34B depicts a side elevational view of the instrument of FIG. 34A with the acoustic assembly moved to a second longitudinal position.

As previously discussed, opening (33A) of cap (33) of instrument (10) provides access to an interior cavity of shaft assembly (30) of instrument (10). Surgical debris, body fluid, etc. may pass through opening (33A) and become stuck on the exterior surface of ultrasonic blade (42) and/or acoustic waveguide (80). It may be desirable to provide ultrasonic blade (42) and/or acoustic waveguide (80) with features that allow for the exterior of both to be efficiently cleaned. An example of such an acoustic assembly (1000) is shown in FIGS. 34A and 34B. Acoustic assembly (1000) comprises ultrasonic blade (42), waveguide (80), and ultrasonic transducer assembly (12). As previously discussed, waveguide (80) is secured within shaft assembly (30) via pin (32), which passes through waveguide (80) and shaft assembly (30). A feature may be provided which allows a user to disengage pin (32) from waveguide (80). It should be understood that disengaging of pin (32) from waveguide (80) will cause acoustic assembly to be disengaged from shaft assembly (30). Once disengaged, acoustic assembly (1000) may be moved longitudinally distally to thereby expose ultrasonic blade (42) and a distal portion of waveguide (80) as shown in FIG. 34B. With ultrasonic blade (42) and the distal portion of waveguide (80) exposed, ultrasonic blade (42) and the distal portion of waveguide (80) may be cleaned to thereby remove surgical debris, body fluid, etc. stuck to the exterior surface of both. Once ultrasonic blade (42) and waveguide (80) are substantially cleaned, ultrasonic blade (42) and waveguide (80) may be retracted back proximally to the position shown in FIG. 34A, and pin (32) may be re-engaged with waveguide (80).

It should be understood that a wiper may project outwardly from an exterior surface of one or both of ultrasonic blade (42) or waveguide (80) such that as acoustic assembly (1000) is moved longitudinally distally, the wiper may drive surgical debris, body fluid, etc. from the interior cavity of shaft assembly (30) and/or clean an interior surface of shaft assembly (30). Body (22) or shaft assembly (30) may include a button or other feature to selectively disengage/re-engage pin (32) with waveguide (80).

VII. Exemplary Cleaning Tools

As discussed above, surgical debris, body fluid, etc. may become disposed within the interior cavity of shaft assembly (30) and may become stuck to surfaces therein, including the exterior surface of waveguide (80) and/or ultrasonic blade (42). It may be desirable to provide tools which provide for effective cleaning of the interior cavity of shaft assembly (30) and the surfaces therein. Several merely illustrative examples of cleaning tools will be discussed in greater detail below, while still other suitable examples will be apparent to those of ordinary skill in the art in view of the teachings herein.

A. First Exemplary Cleaning Tool

FIGS. 35-36 show one merely illustrative example of a cleaning tool (1100). Tool (1100) comprises a shaft (1102) having a proximal end and a distal end. A hook member (1110) extends laterally from the distal end of shaft (1102). Hook member (1110) defines an interior gap (1104) sized to fit about waveguide (80) and/or ultrasonic blade (42). Furthermore, an exterior surface of hook member (1110) is sized to fit within the interior cavity of shaft assembly (30). A plurality of bristles (1106) extend inwardly and outwardly from hook member (1110) such that as hook member (1110) is positioned about ultrasonic blade (42) within the interior cavity of shaft assembly (30), bristles (1106) contact the surfaces of shaft assembly (30), waveguide (80), and ultrasonic blade (42) to thereby clean them. It should be understood that shaft (1102) and/or hook member (1110) of tool (1100) may be flexible. Similarly, hook member (1110) may be resiliently biased to assume the configuration shown in FIGS. 35 and 36; yet still be deformable to some degree.

B. Second Exemplary Cleaning Tool

FIGS. 37 and 38 show an exemplary alternative tool (1120). Tool (1120) comprises a hollow shaft (1122) having a proximal end and a distal end. Hollow shaft (1122) defines an interior bore (1124) sized to fit about waveguide (80) and ultrasonic blade (42). Furthermore, an exterior surface of hollow shaft (1122) is sized to fit within the interior cavity of shaft assembly (30). A plurality of bristles (1126) extend inwardly and outwardly from the distal end of hollow shaft (1122) such that as hollow shaft (1122) is positioned about waveguide (80) and ultrasonic blade (42) within the interior cavity of shaft assembly (30), bristles (1126) contact the surfaces of shaft assembly (30), waveguide (80), and ultrasonic blade (42) to thereby clean them. It should be understood that hollow shaft (1122) may be flexible or resilient.

C. Third Exemplary Cleaning Tool

Figure 39:
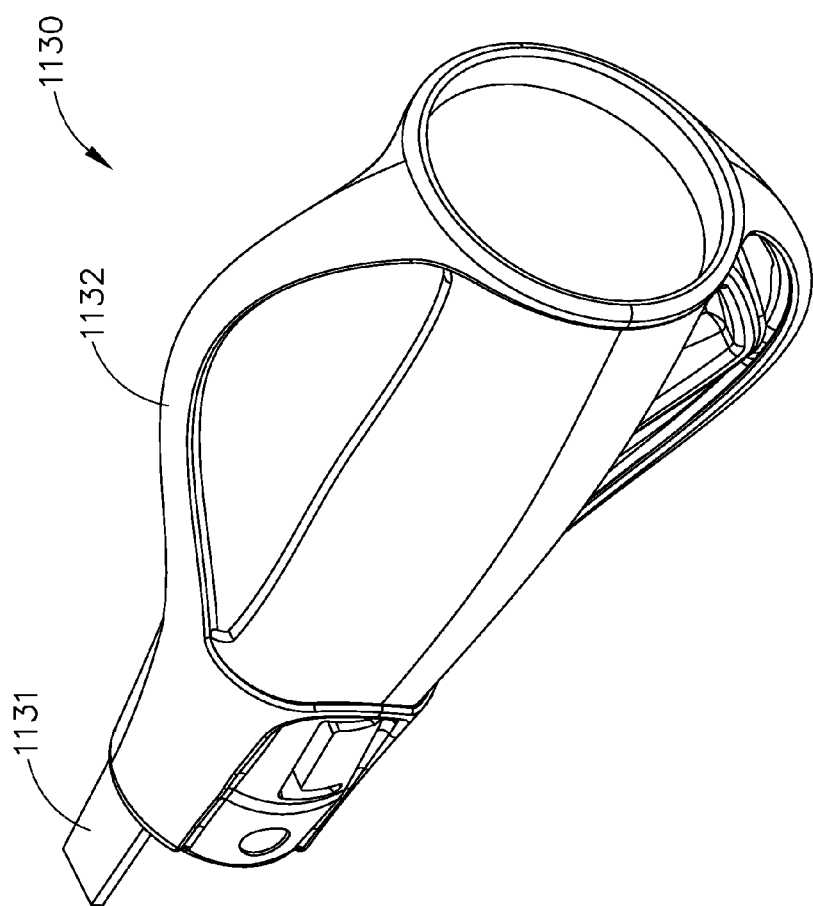
FIG. 39 depicts a perspective view of a torquing device having yet another exemplary cleaning element.
Figure 40:
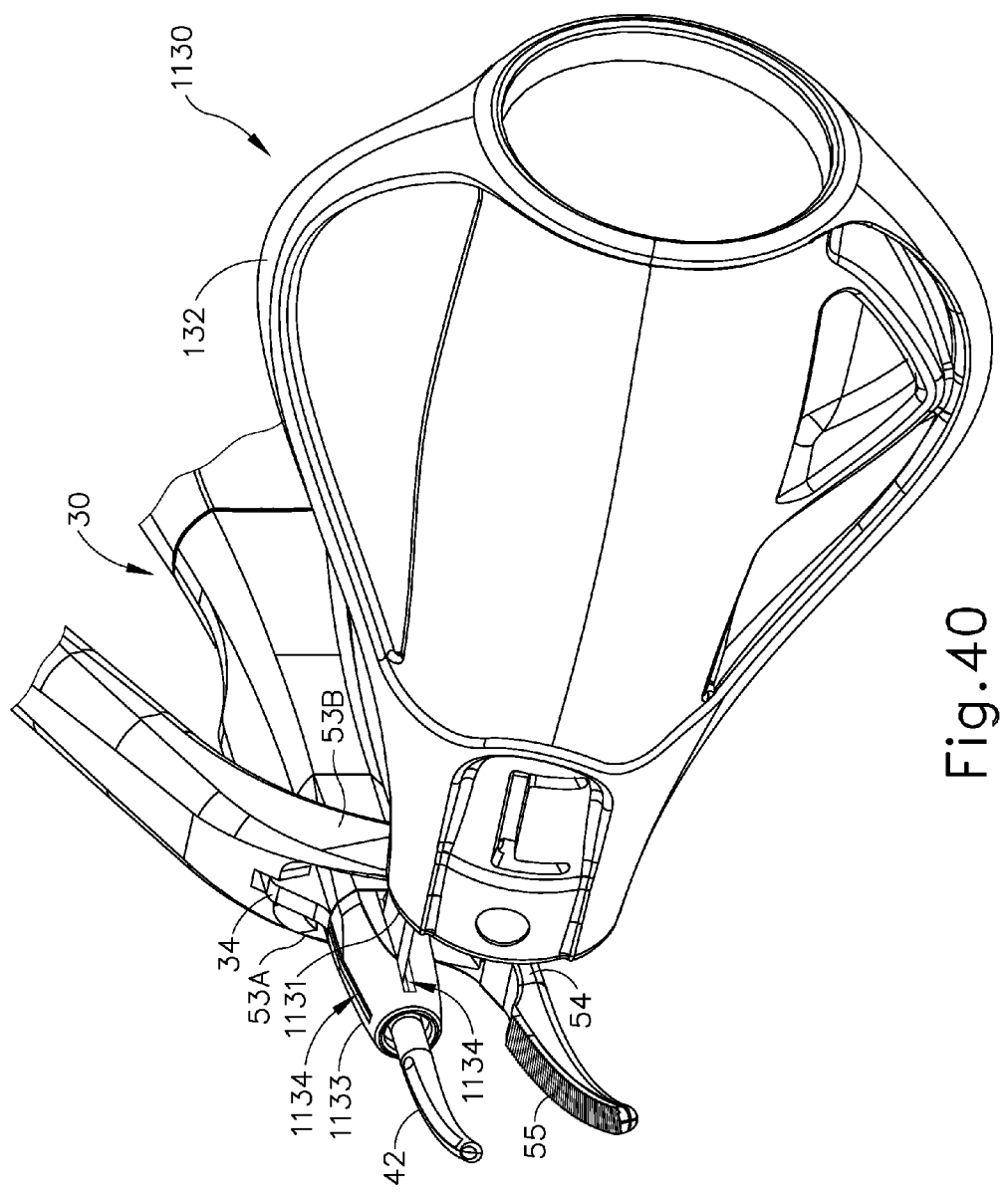
FIG. 40 depicts a perspective view of the torquing device of FIG. 39 with the cleaning element positioned within an end effector of yet another exemplary alternative surgical instrument.

FIGS. 39 and 40 show an exemplary alternative tool (1130). Tool (1130) comprises a torque device (1132) having a tab (1131) extending from a distal end of torque device (1132). Torque device (1132) may be configured and operable in accordance with at least some of the teachings of U.S. Pub. No. 2007/0191713, entitled "Ultrasonic Device for Cutting and Coagulating," published Aug. 16, 2007, the disclosure of which is incorporated by reference herein. As shown in FIG. 40, longitudinal slots (1134) may be formed in an exemplary cap (1133) of instrument (10). Longitudinal slots (1134) pass completely through cap (1133). Longitudinal slots (1134) allow for tab (1131) of tool (1130) to pass through into the interior cavity of shaft assembly (30) to thereby scrape and/or otherwise clean any surgical debris and/or body fluid (2) from the interior cavity of shaft assembly (30). Tab (1131) may be moved longitudinally within longitudinal slots (1134). It should be understood that tab (1131) may comprise bristles, a wiper, and/or any other suitable feature(s) to provide for cleaning of surgical debris, body fluid, etc. from the interior cavity of shaft assembly (30).

VIII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
(a) a body;
(b) a shaft assembly extending distally from the body;
(c) an acoustic assembly, wherein the acoustic assembly comprises:
   (i) an ultrasonic blade, and
   (ii) a waveguide acoustically coupled with the ultrasonic blade, wherein at least a first portion of the waveguide is positioned in the shaft assembly,
   wherein a cavity is defined between a portion of the shaft assembly and corresponding exterior surfaces of the waveguide and the ultrasonic blade;
(d) a clamp arm assembly comprising a clamp pad, wherein the clamp arm assembly is pivotable relative to the body and shaft assembly, wherein the clamp pad is configured to pivot relative to the ultrasonic blade from an open position to a closed position; and
(e) a cleaning feature comprising a cap rotatably coupled with a distal portion of the shaft assembly, wherein the cavity is further defined between an interior surface of the cap and corresponding exterior surfaces of the waveguide and the ultrasonic blade, wherein where the clamp arm assembly is configured to drive rotation of the cap by pivoting the clamp pad from the open position to the closed position, thereby removing surgical debris from the cavity and one or both of:
   (i) the exterior surface of one or both of the waveguide or the ultrasonic blade, or
   (ii) an interior surface of the shaft assembly,
   wherein at least a portion of the cleaning feature is positioned in the cavity.

2. The surgical instrument of claim 1, wherein the cleaning feature is positioned to bear against one or both of:
   (i) the exterior surface of one or both of the waveguide or the ultrasonic blade, or
   (ii) the interior surface of the shaft assembly.

3. The surgical instrument of claim 1, wherein the cleaning feature comprises at least one flexible tab.

4. The surgical instrument of claim 1, wherein the cleaning feature comprises a plurality of projections extending inwardly from the interior surface of the rotatable cap into the cavity.

5. The surgical instrument of claim 1, wherein the cleaning feature comprises a sleeve configured to fit about one or both of the waveguide or the ultrasonic blade.

6. The surgical instrument of claim 5, wherein the sleeve comprises a plurality of cleaning elements configured to scrape surgical debris from one or both of the waveguide or the ultrasonic blade.

7. A surgical instrument comprising:
(a) a body;
(b) a shaft assembly extending distally from the body;
(c) an acoustic assembly, wherein the acoustic assembly comprises:
   (i) an ultrasonic blade, and
   (ii) a waveguide acoustically coupled with the ultrasonic blade, wherein at least a portion of the waveguide is positioned in the shaft assembly,
   wherein a cavity is defined between a portion of the shaft assembly and corresponding exterior surfaces of the waveguide and the ultrasonic blade;
(d) a clamp arm pivotally coupled to either the shaft or the body, wherein the clamp arm further comprises a clamp pad configured to pivot from an open position to a closed position; and
(e) a cleaning feature comprising a cap rotatably coupled with a distal portion of the shaft assembly, wherein the cavity is further defined between an interior surface of the cap and corresponding exterior surfaces of the waveguide and the ultrasonic blade, wherein the cleaning feature is operable to rotate to remove debris from the cavity, wherein the clamp arm is configured to drive rotation of the cap in response to pivoting of the clamp pad from the open position to the closed position.

8. A surgical instrument comprising:
(a) a body;
(b) a shaft assembly extending distally from the body;
(c) an acoustic assembly, wherein the acoustic assembly comprises:
   (i) an ultrasonic blade, and
   (ii) a waveguide acoustically coupled with the ultrasonic blade, wherein at least a portion of the waveguide is positioned in the shaft assembly,
   wherein a cavity is defined between a portion of the shaft assembly and corresponding exterior surfaces of the waveguide and the ultrasonic blade; and
(d) a protective feature comprising a sleeve configured to prevent surgical debris from contacting an exterior surface of one or both of the waveguide or the ultrasonic blade, wherein the sleeve comprises a tapered section and a plurality of scrubbing elements located within an interior surface of the sleeve and extending along the length of the tapered section, wherein the protective feature is positioned within the cavity, wherein the interior surface of the sleeve is configured to scrub surgical debris from corresponding portions of the exterior surface of one or both of the waveguide or the ultrasonic blade in response to activation of the acoustic assembly.

* * * * *